United States Patent [19]
Girard et al.

[11] Patent Number: 5,314,900
[45] Date of Patent: May 24, 1994

[54] ARYL THIOPYRANO[2,3,4-C,D]INDOLES AS INHIBITORS OF LEUKOTRIENE BIOSYNTHESIS

[75] Inventors: Yves Girard, Bizard; John H. Hutchinson, Montreal; Michel Therien, Laval; Daniel Delorme, St-Lazare, all of Canada

[73] Assignee: Merck Frosst Canada, Inc., Kirkland, Canada

[21] Appl. No.: 978,834

[22] Filed: Nov. 19, 1992

[51] Int. Cl.$^5$ .................... A61K 31/40; A61K 31/44; C07D 401/12
[52] U.S. Cl. ..................................... 514/339; 546/270
[58] Field of Search ............... 546/270; 514/339, 826, 514/914

[56] References Cited

FOREIGN PATENT DOCUMENTS

| 0275667 | 7/1988 | European Pat. Off. |
| 0419049 | 3/1991 | European Pat. Off. |
| 56-30979 | 3/1981 | Japan |
| 63-216890 | 9/1988 | Japan |
| 63-277683 | 11/1988 | Japan |

OTHER PUBLICATIONS

Su et al., Abstract; Synthesis of Chuangxinmycin Derivatives, Shanghai Inst. Pharm. Ind.
Kozikowski, et al. J. Am. Chem. Soc., 104, pp. 7622–7626 (1982).
Unangst et al. J. Med Chem, 32, pp. 1360–1366 (1989).

Primary Examiner—Jerome D. Goldberg
Assistant Examiner—Phyllis G. Spivack
Attorney, Agent, or Firm—Mark R. Daniel; Joseph F. DiPrima

[57] ABSTRACT

Compounds having the formula I:

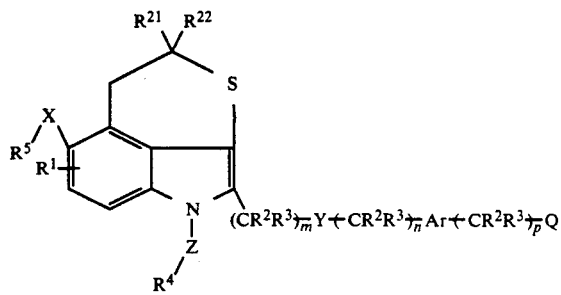

are inhibitors of 5-lipoxygenase and inhibitors of leukotriene biosynthesis. These compounds are useful as anti-asthmatic, anti-allergic, anti-inflammatory, and cytoprotective agents. They are also useful in treating angina, cerebral spasm, glomerular nephritis, hepatitis, endotoxemia, psoriasis, uveitis, and allograft rejection and in preventing the formation of atherosclerotic plaques.

9 Claims, No Drawings

ARYL THIOPYRANO[2,3,4-c,d]INDOLES AS INHIBITORS OF LEUKOTRIENE BIOSYNTHESIS

BACKGROUND OF THE INVENTION

The leukotrienes constitute a group of locally acting hormones, produced in living systems from arachidonic acid. The major leukotrienes are Leukotriene $B_4$ (abbreviated as $LTB_4$), $LTC_4$, $LTD_4$, and $LTE_4$. The biosynthesis of these leukotrienes begins with the action of the enzyme 5-lipoxygenase on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

The thiopyrano[2,3,4-c,d]indole ring system of the compounds of the present invention is novel. A few derivatives of the natural product chuangxinmycin, which contains the thiopyrano[4,3,2-c,d]indole ring system, have been described as showing antibiotic and anticancer utilities. However, in addition to being isomeric with the present ring system, the substitution pattern is very different. The compounds of the present invention have complex substituents at positions 2 and 6, whereas such substitution is for the most part absent or very simple in the thiopyrano[4,3,2-c,d]indoles described. The following structures and references are illustrative of the compounds in the prior art.

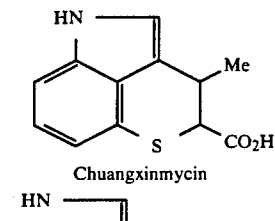

Chuangxinmycin

Kozikowski et al., J. Am. Chem. Soc. 104, 7622-26, 1982.
Matsumoto et al. Japan Kokai Tokkyo Koho 63-216890

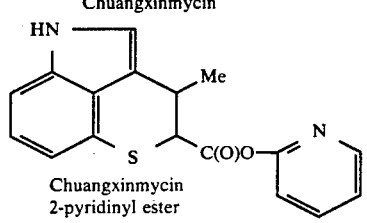

Chuangxinmycin 2-pyridinyl ester

Su et al., Yiyao Gougye, pp. 17-21, 1984 [(Chem. Abst. 101, no. 72492]

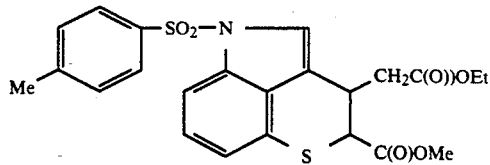

Matsumoto et al., Japan Kokai Tokkyo Koho, 63-277683

SUMMARY OF THE INVENTION

The present invention relates to certain aryl thiopyrano[2,3,4-c,d]indoles having activity as 5-lipoxygenase (5-LO) inhibitors and leukotriene biosynthesis inhibitors, to methods for their preparation, and to methods and pharmaceutical formulations for using these compounds in mammals (especially humans).

Because of their activity as 5-LO inhibitors and as leukotriene biosynthesis inhibitors, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, psoriasis, uveitis, and allograft rejection and in preventing the formation of atherosclerotic plaques.

DETAILED DESCRIPTION OF THE INVENTION

The present invention provides novel compounds of the Formula I:

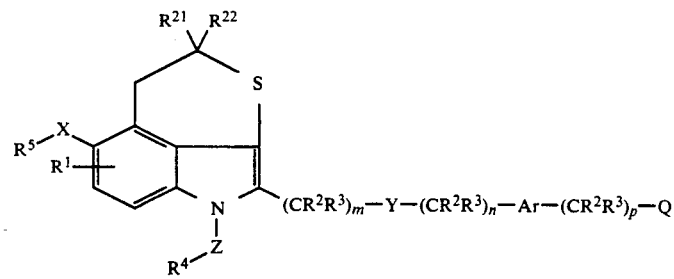

wherein:

$R^1$ is H, lower alkyl, cycloalkyl, lower alkoxy, perhalo lower alkenyl, CN, $NO_2$, $CF_3$, $N_3$, $N(R^6)_2$, $NR^6COR^7$, $NR^6CON(R^6)_2$, $OR^6$, $SR^8$, $S(O)R^8$, $S(O)_2R^8$, $S(O)_2N(R^6)_2$, $COR^7$, $CON(R^6)_2$, $CO_2R^9$, or halogen;

$R^2$ is H, lower alkyl, hydroxy, or lower alkoxy, or two $R^2$ groups on adjacent carbon atoms may be a bond;

$R^3$ is H or lower alkyl;

$R^4$ is H, $[aryl(R^{10})_2]_t$, alkyl, cycloalkyl, lower alkenyl, phenyl lower alkenyl, perhalophenyl, or substituted lower alkyl wherein the substituent is $[aryl(R^{10})_2]_t$, phenoxy, or N-morpholino;

$R^5$ is $[aryl(R^{10})_2]_t$, or substituted lower alkyl wherein the substituent is $[aryl(R^{10})_2]_t$;

$R^6$ is H or lower alkyl, or two $R^6$ groups attached to the same nitrogen may form a saturated ring of 5 or 6 members, optionally containing a second heteroatom chosen from O, S, or $NR^2$;

$R^7$ is H, lower alkyl, phenyl, p-tolyl, or $CF_3$;

$R^8$ is lower alkyl, phenyl, p-tolyl, or $CF_3$;

$R^9$ is H, lower alkyl, or benzyl;

$R^{10}$ is H, lower alkyl, cycloalkyl, lower alkoxy, benzyl, benzyloxy, perhalo lower alkenyl, CN, $NO_2$, $CF_3$, N$_3$, N(R$^6$)$_2$, NR$^6$COR$^7$, NR$^6$CON(R$^6$)$_2$, OR$^6$, SR$^8$, S(O)R$^8$, S(O)$_2$R$^8$, S(O)$_2$N(R$^6$)$_2$, COR$^7$, CON(R$^6$)$_2$, CO$_2$R$^9$, halogen, hydroxy- or lower alkoxy-tetrahydropyranyl, or 1-hydroxy- or 1-lower alkoxy-1-thiazol-2,4, or 5-yl lower alkyl;

R$^{11}$ is H, lower alkyl, lower alkoxy, lower alkylthio, halogen, CN, or CF$_3$;

R$^{12}$ is lower alkyl, phenyl(R$^{10}$)$_2$, CF$_3$, or N(R$^6$)$_2$;

R$^{13}$ is CO$_2$H, N(R$^6$)$_2$, or NHCOR$^7$;

R$^{14}$ is —(CH$_2$)$_s$—C(R$^{15}$)$_2$—(CH$_2$)$_s$—R$^{16}$ or —CH$_2$CON(R$^{18}$)$_2$;

R$^{15}$ is H or lower alkyl;

R$^{16}$ is
 a) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or
 b) the radical V—R$^{17}$;

R$^{17}$ contains up to 20 carbon atoms and is (1) an alkyl group or (2) an alkyl carbonyl group of an organic acyclic or monocyclic carboxylic acid containing not more than 1 heteroatom in the ring;

R$^{18}$ is H or lower alkyl, or two R$^{18}$ groups attached to the same nitrogen may form a saturated ring of 5 or 6 members, optionally containing a second heteroatom chosen from O, S, or NR$^2$;

R$^{19}$ is H, lower alkyl, lower alkylcarbonyl, or lower alkylsulfonyl;

R$^{20}$, R$^{21}$, and R$^{22}$ is each independently H or lower alkyl;

Q is CO$_2$R$^9$, CO$_2$R$^{14}$, CN$_4$H, —OH, —CH$_2$OH, —CHO, —CON(R$^6$)$_2$, —CON(OH)R$^6$, —CONHS(O)$_2$R$^{12}$, —COCN$_4$H, —CONR$^6$(CH$_2$)$_r$R$^{13}$, —N(R$^6$)$_2$, —NHCOR$^7$, S(O)$_2$N(R$^6$)$_2$, S(O)$_2$NHCOR$^{12}$, —NHS(O)$_2$R$^{12}$, —NHCOCO$_2$R$^9$, —CONHCN, or —CONHCN$_4$H;

U is C(R$^{20}$)$_2$, O, S, S(O), S(O)$_2$, or NR$^{19}$;

V is O, S, or NR$^9$;

X is (C(R$^{20}$)$_2$)$_q$U—, —CR$^{20}$=CR$^{20}$—, or —C(R$^{20}$)$_2$OC(R$^{20}$)$_2$—;

Y is a bond, O, S, S(O), S(O)$_2$, NR$^{19}$, or CONR$^9$;

Z is C(R$^{20}$)$_2$, CO, S(O)$_2$, or a bond, with the proviso that when Z is S(O)$_2$ or a bond, then R$^4$ is not H;

m is 0 to 3;
n is 0 to 3;
p is 0 to 3;
q is 0 to 3;
r is 1 to 3;
s is 0 or 1;
t is 1 or 2;

Ar is arylene (R$^{11}$)$_2$, wherein arylene is phenylene, furandiyl, thiendiyl, pyridindiyl, naphthalendiyl, pyrroldiyl, or 1,2,5-thiadiazoldiyl;

aryl is phenyl, pyridinyl, quinolinyl, isoquinolinyl, thiazolyl, thienyl, oxazolyl, pyrimidinyl, pyrazinyl, furopyridinyl, naphthyl, 1,8-naphthyridinyl, or methylenedioxyphenyl, or the N-oxides thereof;

or a pharmaceutically acceptable salt thereof.

A preferred embodiment of the present invention is represented by Formula Ia:

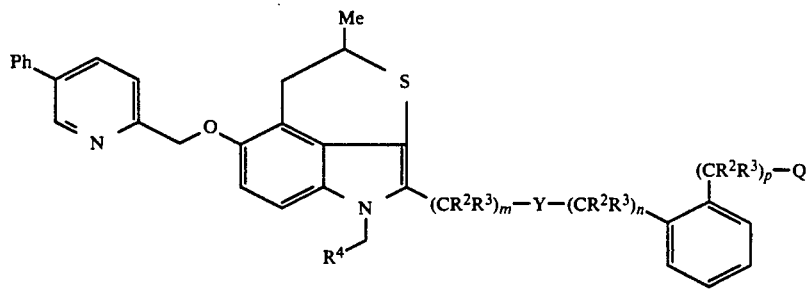

wherein:

R$^4$ is alkyl, cycloalkyl, [aryl(R$^{10}$)$_2$]$_t$, or substituted lower alkyl wherein the substituent is [aryl(R$^{10}$)$_2$]$_t$;

R$^{10}$ is H, lower alkyl, or halogen;

Q is —CO$_2$H, CN$_4$H, or —CONHS(O)$_2$R$^{12}$;

and the remaining substituents are as defined for Formula I.

Definitions

The following abbreviations have the indicated meanings:

Ac=acetyl
Ada=adamantyl
BF$_3$•OEt$_2$=boron trifluoride etherate
c-Bu=cyclobutyl
c-Pen=cyclopentyl
c-Pr=cyclopropyl
c-Hex=cyclohexyl
DEAD=diethyl azidodicarboxylate
DMAP=4-(dimethylamino)pyridine
DMF=dimethylformamide
DMSO=dimethyl sulfoxide
Et=ethyl
Et$_3$N=triethylamine
Fur=furandiyl
HMPA=hexamethylphosphorictriamide
i-Bu=isobutyl
i-Pr=isopropyl
KHMDS=potassium hexamethyldisilazide
LDA=lithium diisopropylamide
m-CPBA=m-chloroperbenzoic acid
Me=methyl
MsCl=methanesulfonyl chloride
n-Bu=normal butyl
n-Pr=normal propyl
p-TSA=p-toluenesulfonic acid
Ph=phenyl
Phe=benzenediyl
psi=pounds per square inch
Pye=pyridinediyl
r.t.=room temperature
t-Bu, t-butyl=tertiary butyl
Tf$_2$O=trifluoromethanesulfonicanhydride
Th=2- or 3-thienyl
TFA=trifluoroacetic acid
TFAA=trifluoroacetic anhydride
THF=tetrahydrofuran Thi=thienediyl
TLC=thin layer chromatography
Triton B=benzyltrimethylammoniumhydroxide
$CN_4H$=1H (or 2H)-tetrazol-5-yl
$C_3H_5$=allyl The term "alkyl" includes "lower alkyl" and extends to cover carbon fragments having up to 20 carbon atoms, and includes linear and branched structures and combinations thereof. Examples of alkyl groups include octyl, nonyl, undecyl, dodecyl, tridecyl, tetradecyl, pentadecyl, eicosyl, 3,7-diethyl-2,2-dimethyl-4-propyl-nonyl, and the like.

The term "lower alkyl" means alkyl groups of from 1 to 7 carbon atoms. Examples of lower alkyl groups include methyl, ethyl, propyl, isopropyl, butyl, sec- and tert-butyl, pentyl, hexyl, heptyl, and the like.

The term "cycloalkyl" means a hydrocarbon containing one or more rings having from 3 to 12 carbon atoms, with the hydrocarbon having up to a total of 20 carbon atoms. Examples of cycloalkyl groups are cylopropyl, cyclopentyl, cycloheptyl, adamantyl, cyclododecylmethyl, 2-ethyl-1-bicyclo[4.4.0]decyl, and the like.

"Lower alkenyl" means alkenyl groups of 2 to 7 carbon atoms. Examples of lower alkenyl groups include vinyl, allyl, isopropenyl, pentenyl, hexenyl, heptenyl, 1-propenyl, 2-butenyl, 2-methyl-2-butenyl, and the like.

The term "lower alkoxy" means alkoxy groups of 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

"Alkylcarbonyl" means alkylcarbonyl groups of 1 to 20 carbon atoms of a straight, branched or cyclic configuration. Examples of alkylcarbonyl groups are 2-methylbutanoyl, octadecanoyl, 11-cyclohexylundecanoyl, and the like. Thus, the 11-cyclohexylundecanoyl, group is c-Hex-$(CH_2)_{10}$—C(O)—.

Halogen includes F, Cl, Br, and I.

It is intended that the definitions of any substituent (e.g., $R^1$, $R^2$, $R^6$, etc.) in a particular molecule be independent of its definitions elsewhere in the molecule. Thus, $N(R^6)_2$ represents —NHH, —NHMe, —N(Me)(Et), etc.

The heterocycles formed when two $R^6$ (or $R^{18}$) groups join through N include pyrrolidine, piperidine, morpholine, thiamorpholine, piperazine, and N-methylpiperazine.

The prodrug esters of Q (i.e., when Q=$CO_2R^{14}$) are intended to include the esters such as are described by Saari et al., J. Med. Chem., 21, No. 8, 746–753 (1978), Sakamoto et al., Chem. Pharm. Bull., 32, No. 6, 2241-2248 (1984) and Bundgaard et al., J. Med. Chem., 30, No. 3, 451–454 (1987). Within the definition of $R^{16}$, some representative monocyclic or bicyclic heterocyclic radicals are:
2,5-dioxo-1-pyrrolidinyl,
(3-pyridinylcarbonyl)amino,
1,3-dihydro-1,3-dioxo-2H-isoindol-2-yl,
1,3-dihydro-2H-isoindol-2-yl,
2,4-imidazolinedion-1-yl,
2,6-piperidinedion-1-yl,
2-imidazolyl,
2-oxo-1,3-dioxolen-4-yl,
piperidin-1-yl,
morpholin-1-yl, and
piperazin-1-yl.

Optical Isomers—Diastereomers—Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. Mixed salts may at times be advantageous.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

It will be understood that in the discussion of methods of treatment which follows, references to the compounds of Formula I are meant to also include the pharmaceutically acceptable salts.

Utilities

The ability of the compounds of Formula I to inhibit 5-lipoxygenase and to inhibit biosynthesis of the leukotrienes makes them useful for preventing or reversing the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as psoriasis, atopic eczema, and the like, 6) cardiovascular disorders such as angina, formation of atherosclerotic plaques, myocardial ischemia, hypertension, platelet aggregation and the like, 7) renal insufficiency arising from ischaemia induced by immunological or chemical (cyclosporin) etiology and 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) cholecystitis, and 16) metastasis of tumors.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP 140,684.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, opthalmic preparations for ocular administration comprising 0.001-1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be coadiminstration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Pharmaceutical Compositions

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/mL |
| --- | --- |
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of | 1 mL |

| Tablet | mg/tablet |
| --- | --- |
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
| --- | --- |
| Compound of Formula I | 25 |
| Lactose Powder | 573.5 |
| Magnesium Stearate | 1.5 |
| | 600 |

| Aerosol | Per canister |
| --- | --- |
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

Combinations with other drugs

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the oxicams; and
(5) the biphenylcarboxylic acid derivatives;
or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH₃)COOH or —CH₂CH₂COOH group (which optionally can be in the form of a pharmaceutically acceptable salt group, e.g., —CH(CH₃)COO⁻Na⁺ or —CH₂CH₂COO⁻Na⁺), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g. —CH₂COO⁻Na⁺), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

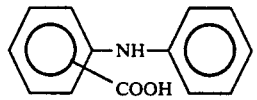

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

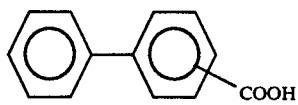

which can bear a variety of substituents and in which the free —COOH group can be in the form of a pharmaceutically acceptable salt group, e.g., —COO⁻Na⁺.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

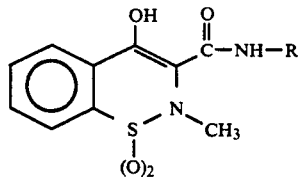

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid and ufenamate.

The following NSAIDs, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDS are acetyl salicylic acid, diclofenac, fenbufen, fenoprofen, flurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885

(Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an $H_1$- or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in Nature, Vol. 316, pages 126-131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Representative Compounds

Tables 1-4 illustrate compounds representative of the present invention.

TABLE 1

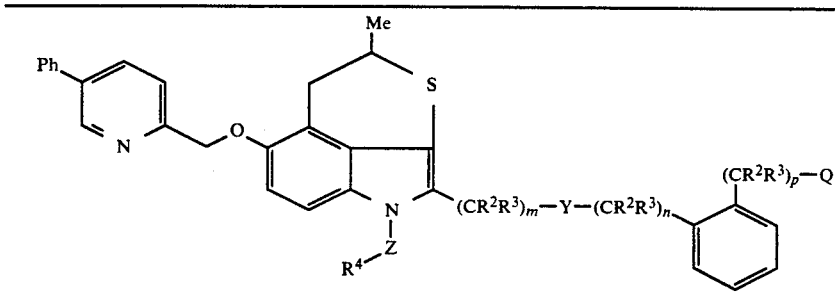

Ib

| EX. NO. | $R^4Z$ | $(CR^2R^3)_m Y(CR^2R^3)_n$ | $(CR^2R^3)_p$ | Q |
|---|---|---|---|---|
| 1 | 4-ClC$_6$H$_4$CH$_2$ | CH$_2$S | — | CO$_2$H |
| 2 | 3-ClC$_6$H$_4$CH$_2$ | CH$_2$S | — | CO$_2$H |
| 3 | 4-FC$_6$H$_4$CH$_2$ | CH$_2$S | — | CO$_2$H |
| 4 | 4-ClC$_6$H$_4$CH$_2$ | CH$_2$S | — | CONHS(O)$_2$Me |
| 5 | 4-ClC$_6$H$_4$CH$_2$ | CH$_2$O | CH$_2$ | CO$_2$H |
| 6 | 4-ClC$_6$H$_4$CH$_2$ | CH$_2$O | CH$_2$ | CONHS(O)$_2$Me |
| 7 | 4-ClC$_6$H$_4$CH$_2$ | CH$_2$O | CH(Me) | CO$_2$H |
| 8 | 4-ClC$_6$H$_4$CH$_2$ | CH$_2$O | CH(Me) | CONHS(O)$_2$Me |
| 9 | 4-ClC$_6$H$_4$CH$_2$ | CH$_2$O | CH(Et) | CO$_2$H |
| 10 | 4-ClC$_6$H$_4$CH$_2$ | CH$_2$S | CH$_2$ | CO$_2$H |
| 11 | 3-ClC$_6$H$_4$CH$_2$ | CH$_2$O | CH$_2$ | CO$_2$H |
| 12 | 3-ClC$_6$H$_4$CH$_2$ | CH$_2$O | CH(Me) | CO$_2$H |
| 13 | 4-FC$_6$H$_4$CH$_2$ | CH$_2$O | CH$_2$ | CO$_2$H |
| 14 | 4-FC$_6$H$_4$CH$_2$ | CH$_2$O | CH(Me) | CO$_2$H |
| 15 | 3-Cl-4FC$_6$H$_3$CH$_2$ | CH$_2$O | CH$_2$ | CO$_2$H |
| 16 | C$_6$H$_5$ | CH$_2$O | CH$_2$ | CO$_2$H |
| 17* | 3-(C$_5$H$_7$O)C$_6$H$_4$CH$_2$ | CH$_2$O | CH$_2$ | CO$_2$H |
| 18 | 4-ClC$_6$H$_4$CH$_2$ | CH$_2$OCH$_2$ | — | CO$_2$H |
| 19 | 4-ClC$_6$H$_4$CH$_2$ | CH$_2$OCH$_2$ | — | CN$_4$H |
| 20 | 4-ClC$_6$H$_4$CH$_2$ | (CH$_2$)$_2$OCH$_2$ | — | CN$_4$H |
| 21 | 4-ClC$_6$H$_4$CH$_2$ | (CH$_2$)$_2$S | — | CO$_2$H |
| 22 | 4-ClC$_6$H$_4$CH$_2$ | (CH$_2$)$_2$O | — | CO$_2$H |
| 23 | 4-ClC$_6$H$_4$CH$_2$ | (CH$_2$)$_2$O | — | CONHS(O)$_2$Me |
| 24 | 4-ClC$_6$H$_4$CH$_2$ | (CH$_2$)$_2$O | — | CN$_4$H |
| 25 | 4-ClC$_6$H$_4$CH$_2$ | (CH$_2$)$_2$O | — | S(O)$_2$NHCOMe |
| 26 | 4-ClC$_6$H$_4$CH$_2$ | (CH$_2$)$_2$O | — | S(O)$_2$NHCOPh |
| 27 | 3-ClC$_6$H$_4$CH$_2$ | (CH$_2$)$_2$O | — | CO$_2$H |
| 28 | 4-ClC$_6$H$_4$CH$_2$ | (CH$_2$)$_2$S | CH$_2$ | CO$_2$H |
| 29 | 4-ClC$_6$H$_4$CH$_2$ | (CH$_2$)$_2$O | CH$_2$ | CO$_2$H |
| 30 | 4-ClC$_6$H$_4$CH$_2$ | (CH$_2$)$_2$O | CH(Me) | CO$_2$H |
| 31 | 4-ClC$_6$H$_4$CH$_2$ | (CH$_2$)$_2$O | CH(Et) | CO$_2$H |
| 32 | 3-ClC$_6$H$_4$CH$_2$ | (CH$_2$)$_2$O | CH$_2$ | CO$_2$H |
| 33 | 3-ClC$_6$H$_4$CH$_2$ | (CH$_2$)$_2$O | CH$_2$ | CO$_2$H |
| (−) enantiomer | | | | |
| 34 | 3-ClC$_6$H$_4$CH$_2$ | (CH$_2$)$_2$O | CH$_2$ | CO$_2$H |

TABLE 1-continued

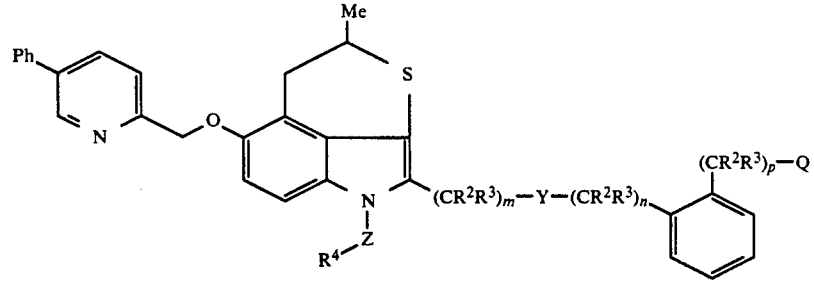

Ib

| EX. NO. | R⁴Z | (CR²R³)ₘY(CR²R³)ₙ | (CR²R³)ₚ | Q |
|---|---|---|---|---|
| (+) enantiomer 35 | 4-FC₆H₄CH₂ | (CH₂)₂O | CH₂ | CO₂H |
| 36 | 4-FC₆H₄CH₂ | (CH₂)₂O | CH₂ | CO₂H |
| (−) enantiomer 37 | 4-FC₆H₄CH₂ | (CH₂)₂O | CH₂ | CO₂H |
| (+) enantiomer 38 | 4-FC₆H₄CH₂ | (CH₂)₂O | CH(Me) | CO₂H |
| 39 | 3-FC₆H₄CH₂ | (CH₂)₂O | CH₂ | CO₂H |
| 40 | 4-ClC₆H₄CH₂ | S | — | CO₂H |
| 41 | 4-ClC₆H₄CH₂ | S | CH₂ | CO₂H |
| 42 | 4-ClC₆H₄CH₂ | CH=CH (E&Z isomers) | — | CN₄H |
| 43 | 4-ClC₆H₄CH₂ | (CH₂)₂ | — | CO₂H |
| 44 | 4-ClC₆H₄CH₂ | (CH₂)₂ | — | CN₄H |
| 58 | 4-ClC₆H₄CH₂ | CH₂O | CH₂ | CO₂H |
| (+) enantiomer 59 | 4-ClC₆H₄CH₂ | CH₂O | CH₂ | CO₂H |
| (−) enantiomer 60 | 4-ClC₆H₄CH₂ | CH₂O | CH(Me) | CO₂H |
| (−) enantiomer 61 | 4-FC₆H₄CH₂ | CH₂O | CH(Me) | CO₂H |
| (+) enantiomer 62 | 4-FC₆H₄CH₂ | CH₂O | CH(Me) | CO₂H |
| (−) enantiomer 63 | 3-I-4-N₃C₆H₃S(O)₂ | CH₂S | — | CO₂H |
| 64 | 3-ClC₆H₄CH₂ | CH₂O | CH₂ | CO₂H |
| (−) enantiomer 65 | 3-ClC₆H₄CH₂ | CH₂O | CH₂ | CO₂H |
| (+) enantiomer | | | | |

*EX 17: C₅H₇O is 2H-5,6-dihydropyran-4-yl

TABLE 2

Ic

| EX. NO. | (CR²R³)ₘY(CR²R³)ₙ | Q |
|---|---|---|
| 45 | (CH₂)₂ | CO₂H |
| 46 | CH₂OCH₂ | CO₂H |
| 47 | CH₂OCH₂ | CN₄H |
| 48 | (CH₂)₂OCH₂ | CO₂H |
| 49 | (CH₂)₂OCH₂ | CN₄H |
| 50 | (CH₂)₂O | CO₂H |

TABLE 3

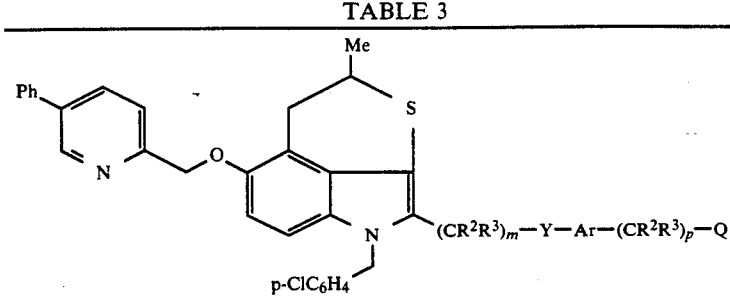

| EX. NO. | $(CR^2R^3)_m Y$ | Ar | $(CR^2R^3)_p$ | Q |
|---|---|---|---|---|
| 51 | CH(OH) | 2,5-furandiyl | — | $CO_2H$ |
| 52 | $CH_2$ | 2,5-furandiyl | — | $CO_2H$ |
| 53 | CH(OMe) | 2,5-furandiyl | — | $CO_2H$ |
| 54 | $CH_2$ | 2,5-furandiyl | $CH_2$ | $CO_2H$ |
| 55 | $CH_2$ | 2,5-furandiyl | — | $CONHS(O)_2Me$ |
| 56 | $CH_2$ | 2,5-furandiyl | — | $CONHS(O)_2Ph$ |
| 57 | $(CH_2)_2O$ | $C_6H_3Cl$ | — | $CO_2H$ |
| 72 | $CH_2O$ | $C_{10}H_6$ | — | $CO_2H$ |

TABLE 4

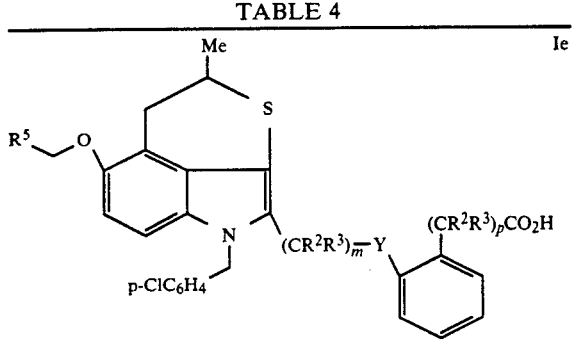

| EX. NO. | $R^5$ | $(CR_2^2)_m Y$ | $(CR^2R^3)_p$ |
|---|---|---|---|
| 66 | 2-quinolinyl | $CH_2S$ | — |
| 67 | 2-quinolinyl | $CH_2O$ | $CH_2$ |
| 68 | 3-isoquinolinyl | $CH_2S$ | $CH_2$ |
| 69 | 2-pyridinyl | $CH_2S$ | — |
| 70 | 5-methoxy-2-pyridinyl | $CH_2S$ | — |
| 71 | 2-methylthiazol-4-yl | $CH_2O$ | $CH_2$ |

Methods of Synthesis

Compounds of the formula I of the present invention may be prepared according to the synthetic routes outlined in the Schemes I to VIII and by following the methods described herein. Exemplary alkylating agents $R^4CH_2X^1$ and $R^5CH_2X^1$ are given in Table A.

TABLE A

| COMPOUNDS | $X^1$ | $R^4/R^5$ | NAME |
|---|---|---|---|
| 1 | Cl | $4-ClC_6H_4$ | 4-chlorobenzyl chloride (Aldrich)* |
| 2 | Cl | $C_6H_5$ | Benzyl chloride (Aldrich) |
| 3 | Cl | $4-MeOC_6H_4$ | 4-methoxybenzyl chloride (Aldrich) |
| 4 | Cl | $3-MeOC_6H_4$ | 3-methoxybenzyl chloride (Aldrich) |
| 5 | Cl | $4-MeS(O)_2C_6H_4$ | 4-methylsulfonyl-benzyl chloride (C.A.: 78:111325q (1973)) |
| 6 | Cl | $4-MeSC_6H_4$ | 4-methylthiobenzyl chloride (C.A.: 56:4773g (1962)) |
| 7 | Cl | $4-C_6H_5C_6H_4$ | 4-phenylbenzyl chloride (Aldrich) |
| 8 | Br | $4-NCC_6H_4$ | 4-cyanobenzyl bromide (Aldrich) |
| 9 | Br | $3-C_6H_5(CH_2)_2$ | 3-phenylpropyl bromide (Aldrich) |
| 10 | Cl | $CH_2O_2C_6H_3$ | 3,4-methylenedioxybenzyl chloride (Tet. Lett. 47, 4789–4792 (1972)) |
| 11 | I | $C_6H_5OCH_2$ | 2-phenoxyethyl iodide (C.A.: 77: 15624v (1972)) |
| 12 | Br | $C_6H_5CH=CH$ | Cinnamyl bromide (Aldrich) |
| 13 | Br | c-Hex | Cyclohexylmethyl bromide (Aldrich) |
| 14 | I | H | Methyl iodide (Aldrich) |
| 15 | Br | $CH_2=CH$ | Allyl bromide (Aldrich) |
| 16 | Br | $CH_3(CH_2)_2$ | n-butyl bromide (Aldrich) |
| 17 | Br | $CH_3(CH_2)_8$ | n-decyl bromide (Aldrich) |
| 18 | $OS(O)_2C_6H_4Me$ | $C_6H_5CH_2$ | 2-phenethyl p-toluenesulfonate (C.A.: 72:47966w (1970)) |
| 19 | I | $c-Hex(CH_2)_2$ | 3-cyclohexylpropyl iodide** |
| 20 | $OS(O)_2CH_3$ | $C_4H_3S$ | 2-thienylmethyl methanesulfonate** |
| 21 | Cl | $2-C_5H_4N.HCl$ | 2-picolyl chloride hydrochloride (Aldrich) |
| 22 | Cl | $2-C_9H_6N.HCl$ | 2-chloromethyl-quinoline hydrochloride (Aldrich) |
| 23 | Cl | $5-C_6H_5-2-C_5H_3N$ | 5-phenyl-2-picolyl chloride** |
| 24 | Br | $1-AdaCH_2$ | 2-(1-adamantyl)ethyl bromide** |

TABLE A-continued

Alkylating Agents R⁴CH₂X¹/R⁵CH₂X¹

| COMPOUNDS | $X^1$ | $R^4/R^5$ | NAME |
|---|---|---|---|
| 25 | Cl | 4-FC₆H₄ | 4-fluorobenzyl chloride (PCR Inc.)* |
| 26 | Cl | 3-ClC₆H₄ | 3-chlorobenzyl chloride (Aldrich) |
| 27 | Cl | 3-FC₆H₄ | 3-fluorobenzyl chloride (Aldrich) |
| 28 | Cl | 5-C₆H₅-2-C₅H₃N(O) | 2-chloromethyl-5-phenylpyridine N-oxide** |
| 29 | Cl | 2-C₉H₆N(O) | 2-chloromethyl-quinoline N-oxide (Chem. Pharm. Bull. 28, 2436–2442 (1980)) |
| 30 | Cl | 6-C₆H₅-2-C₅H₃N | 6-phenyl-2-picolyl chloride (C.A.: 103:215289g (1985)) |
| 31 | Cl | 4-C₆H₅-2-C₅H₃N | 4-phenyl-2-picolyl chloride (C.A.: 105:42802e (1986)) |
| 32 | Cl | 2-C₆H₅-3-C₅H₃N | 2-phenyl-3-picolyl chloride** |
| 33 | Cl | 3-C₅H₄N.HCl | 3-picolyl chloride hydrochloride (Aldrich) |
| 34 | Cl | 4-C₅H₄N.HCl | 4-picolyl chloride hydrochloride (Aldrich) |
| 35 | Cl | 2-C₆H₅-4-C₅H₃N | 2-phenyl-4-picolyl chloride (C.A.: 64:690h (1966)) |
| 36 | Cl | 5-NC-2-C₅H₃N | 5-cyano-2-picolyl chloride (Aust. J. Chem. 35, 1451–1468 (1982)) |
| 37 | Cl | 5-n-Bu-2-C₅H₃N | 5-butyl-2-picolyl chloride (C.A.: 78:29778f (1973)) |
| 38 | Cl | 6-Cl-2-C₅H₃N | 6-chloro-2-picolyl chloride (Tetrahedron 38, 3277–3280 (1982)) |
| 39 | Cl | 6-Cl-5-C₆H₅-2-C₅H₂N | 6-chloro-5-phenyl-2-picolyl chloride** |
| 40 | Cl | 4-Cl-5-C₆H₅-2-C₅H₂N | 4-chloro-5-phenyl-2-picolyl chloride** |
| 41 | Cl | t-Bu(C₆H₅)₂SiO-2-C₅H₃N | 5-(t-butyldiphenylsilyloxy)-2-picolyl chloride** |
| 42 | Cl | 5-C₆H₅CH₂-2-C₅H₃N | 5-benzyl-2-picolyl chloride** |
| 43 | Cl | 5-(4-ClC₆H₄)-2-C₅H₃N | 5-(4-chlorophenyl)-2-picolyl chloride** |
| 44 | Cl | 3-C₉H₆N | 3-chloromethyl-isoquinoline (C.A.: 94, 121512t (1981) |
| 45 | Br | 4-C₉H₆N | 4-bromomethyl-quinoline (Indian J. Chem. 11, 1051 (1973)) |
| 46 | Cl | 2-C₈H₆N₂ | 2-chloromethyl-1,8-naphthyridine** |
| 47 | Cl | 4-(2-C₅H₄N)C₆H₄ | 4-(2-pyridinyl)benzyl chloride** |
| 48 | Cl | 3,5-Me₂-4-C₃NO | 4-chloromethyl-3,5-dimethylisoxazole (Aldrich) |
| 49 | Cl | 2-(4-ClC₆H₄)-4-C₃HNS | 4-chloromethyl-2-(4-chlorophenyl)thiazole (Maybridge)* |
| 50 | Cl | 5-C₆H₅-2-C₃HNO | 2-chloromethyl-5-phenyloxazole (J.O.C. 45, 3657–3664 (1980)) |
| 51 | Cl | 5-C₆H₅-2-C₄H₂N₂ | 2-chloromethyl-5-phenylpyrimidine (Chem. Ber. 104, 2975-1983 (1971)) |
| 52 | Cl | 5-C₆H₅-2-C₄H₂N₂ | 2-chloromethyl-5-phenyl pyrazine (Chem. Pharm. Bull. 27, 2027–2041 (1979)) |
| 53 | Br | 2-C₁₀H₇ | 2-bromomethyl-naphthalene (Aldrich) |
| 54 | Cl | 5-(1-C₁₀H₇)-2-C₅H₃N | 5-(1-naphthyl)-2-picolyl chloride** |
| 55 | Cl | 5-(4-MeOC₆H₄)-2-C₅H₃N | 5-(4-methoxyphenyl)-2-picolyl chloride** |
| 56 | Cl | 5-CO₂Me-2-C₅H₃N | 5-carbomethoxy-2-picolyl chloride (C.A.: 79:105075n (1973)) |
| 57 | Cl | 2-C₆H₅-5-C₇H₃NO | 5-chloromethyl-2-phenylfuro[3,2-b]pyridine** |
| 58 | Cl | 3-CF₃C₆H₄ | 3-trifluoromethyl-benzyl chloride (Aldrich) |
| 59 | Cl | 3-(MeOC₅H₈O)C₆H₄ | 3-(4-methoxytetrahydropyran-4-yl)benzyl chloride |

*Aldrich Chemical Co., Milwaukee, Wisc.
Maybridge Chemical Co., Cornwall, U.K.
PCR Inc., Gainsville, Fla.
**Preparation described infra.

Methods of Synthesis

Compounds of the present invention can be prepared according to the following methods. The substituents are the same as in Formula I except where defined otherwise.

Scheme I

The 4-allyloxyphenyl hydrazine II may be prepared from the acetamido phenol IIa by the following chemical transformations: 1) Allylation with allyl bromide in an organic solvent such as DMF and in the presence of a base such as $K_2CO_3$ or $Cs_2CO_3$; 2) Saponification using standard conditions; 3) Diazotisation and reduction of the diazonium salt using standard conditions; and 4) Alkylation using the appropriate halide in an organic solvent such as toluene and in the presence of an organic base such as triethylamine or diisopropyl ethylamine. The indole intermediate IV of Scheme I may be prepared by a Fischer-Indole condensation between ketone III (EP 419,049, p. 27) and the 4-allyl-oxyphenyl hydrazine II in an organic solvent such as toluene with an organic acid such as acetic acid buffered with sodium acetate. Preparation of the thiopyranoindole V may be achieved by heating the indole IV in a high boiling solvent, e.g. 1,2-dichlorobenzene, to effect a Claisen rearrangement resulting in a 4-allyl-5-hydroxy substituted indole. Addition of an organic acid such as p-toluenesulfonic acid to the reaction mixture promotes the cyclisation and thus yields the thiopyranoindole V. Coupling of the phenol V with an alkylating agent $R^5CH_2X$, typified by 5-phenyl-2-picolyl chloride, in an organic solvent (e.g., DMF) using an inorganic base (e.g., $Cs_2CO_3$) provides the thiopyranoindole intermediate VI where $R^5$ corresponds to 5-phenylpyridin-2-yl. Reduction of the ester of compound VI using, for example, lithium aluminum hydride in THF affords the alcohol VII. Reversing the order of reactions, i.e. reduction of the ester V to give the alcohol VIII followed by coupling with an appropriate alkylating agent (using similar reaction conditions as previously described), also provides access to compounds of formula VII.

An alternative route to thiopyranoindoles of formula VII is accomplished by debenzylation of the thiopyranoindole V (where $R^4$ is phenyl $(R^{10})_2$) using a Lewis acid such as boron tribromide in an appropriate organic solvent (e.g., dichloromethane) to provide compound IX. The phenol of compound IX may be coupled with an alkylating agent as described previously to give the thiopyranoindole X which, on reduction of the ester (as before) gives the intermediate XI. Deprotonation of the indolic nitrogen of compound XI, using, e.g., KHMDS as a base in an organic solvent such as DMF and reaction with an alkylating agent $R^4CH_2X^1$, results in the preparation of compounds of formula VII.

Scheme II

Scheme II describes the synthesis of compounds of formula I starting with the thiopyranoindole VII (from Scheme I). In the case where $m > 1$ the alcohol of compound VII may be transformed to the bromo derivative XII by reaction with triphenylphosphine and carbon tetrabromide in an organic solvent such as chloroform. Displacement of the bromine of compound XII with an appropriate nucleophile, $HSAr(CR^2R^3)_pCO_2R^9$, using sodium hydride in DMF, followed by hydrolysis if necessary, provides compounds of formula IA. For the alcohol VII where $m = 1$, brief treatment of this alcohol in an organic solvent (e.g., 1,2-dichloroethane) with boron trifluoride etherate and the above thiol acid derivative leads to compounds corresponding to formula IB.

Treatment of the alcohol of compound VII with a phosphine such as triphenylphosphine, a coupling reagent (e.g., DEAD) and a phenolic ester, $HOAr(CR^2R^3)_pCO_2R^9$, in an organic solvent like THF gives rise to the ester XIII. Saponification of ester XIII using an inorganic base (e.g., lithium hydroxide) in aqueous methanol/THF yields IC. The alcohol of compound VII may be converted to the nitrile derivative XIV by sequential treatment with an inorganic base (e.g., sodium hydride) and an alkylating agent $(Br(CR^2R^3)_nArCN)$ in an organic solvent such as DMF. The nitrile XIV may then be hydrolysed using an inorganic base such as potassium hydroxide in a high boiling organic solvent (e.g., ethylene glycol and 2-(ethoxyethoxy) ethanol) to provide the acid of formula ID. Alternatively, the nitrile XIV on heating in a high boiling organic solvent (for example, 1,2-dichlorobenzene) with tri-n-butyltin azide affords the tetrazole derivative IE.

Scheme III

Scheme III shows further methods used to prepare compounds of formula I. The ester V (from Scheme I) may be hydrolysed to the acid XV using previously described conditions. Decarboxylation of the acid of intermediate XV may be achieved by heating in an organic solvent such as toluene in the presence of an organic acid (e.g., p-toluenesulfonic acid) to afford the thiopyranoindole XVI. Introduction of a sulfur substituent at the C-2 position of the thiopyranoindole XVI is achieved by stirring the compound XVI in an organic solvent such as DMF and adding a solution of an arylsulfenyl chloride, $ClSAr(CR^2R^3)_pCO_2R^9$ (prepared from a bis-(carboalkoxyphenyl)disulfide and sulfuryl chloride) in 1,2-dichloroethane. This procedure leads to intermediate XVII which can be coupled with an alkylating reagent $R^5CH_2X^1$ as before to give compound XVIII. Hydrolysis of compound XVIII the using standard conditions then affords the acid IF. The acid group of compound IF may be homologated to provide compound IG using the following procedure: first, the acid IF is transformed into the corresponding acid chloride using, for example, oxalylchloride and a catalytic amount of DMF in a solvent such as dichloromethane. Ethereal diazomethane is then added followed by methanol, triethylamine, and silver benzoate. This provides the intermediate ester XIX which can be hydrolysed as before to provide acid IG.

Scheme IV

As shown in Scheme IV, the alcohol VII (from Scheme I, where $m = 1$) may be oxidised to the aldehyde XX by treatment with an inorganic oxidising reagent such as manganese dioxide in an organic solvent (e.g., THF). A Wittig reaction between aldehyde XX and a suitable ylid, $Ph_3PCHArCN$, in an organic solvent such as THF affords the intermediate XXI. Such an ylid may be prepared by first reacting triphenylphosphine with an benzyl halide ($HalCH_2ArCN$) in acetonitrile to provide a triphenylphosphonium salt. This salt on treatment with a strong base such as n-BuLi in a solvent such as THF yields the ylid in solution which is then reacted with aldehyde XX. The nitrile XXI may then be hydrolysed to the acid IH or, alternatively, transformed to the tetrazole IK both reactions using conditions previously described. The saturated analogues acid IJ and tetrazole IL can be prepared in a similar fashion from the saturated derivative XXII. This compound is, in turn, derived from the nitrile XXI by reacting it in an organic solvent (e.g., dichloromethane) with triethylsilane in the presence of a Lewis acid such as boron trifluoride etherate.

Scheme V

Alternative ways of preparing derivatives of formula I starting with the aldehyde XX are presented in Scheme V. Carbanions of aromatic carboxylic acids and derivatives can be generated in a variety of ways, as described in textbooks such as *Comprehensive Organic Transformations* by R. C. Larock, VCH Publishers Inc., New York, 1989, pages 54–55. The dianion $LiArCO_2Li$ is an example of a suitable carbanion, which on reaction with the aldehyde XX followed by treatment of the product with ethereal diazomethane yields the hydroxy-ester XXIII. Hydrolysis of this ester gives access to compounds corresponding to formula IM. The hydroxyl group of the hydroxy-ester XXIII may be methylated using an inorganic base such as sodium hydride in an organic solvent (e.g., DMF) followed by the addition of methyl iodide to provide the methyl ether XXVI. Subsequent hydrolysis gives the acid IQ. To remove the hydroxyl group from intermediate XXIII the compound is dissolved in an organic solvent (e.g., dichloromethane) and treated sequentially with triethylsilane and trifluoroacetic acid. This provides the ester XXIV the hydrolysis of which affords the acid of formula IN. The acid IN can be homologated to give the ester XXV and then hydrolysed to the acid IP by using the procedure described in Scheme III for homologation of acid IF.

Scheme VI

Compounds corresponding to formula I where X=—CH=CH— or —CH$_2$CH$_2$— can be prepared using the reaction pathways outlined in Scheme VI. The phenol ester V (from Scheme 1) may be converted to the triflate XXVII by stirring with trifluoromethanesulfonic anhydride, and an organic base (e.g., pyridine) in a solvent such as dichloromethane. The ester of intermediate XXVII may be reduced to the alcohol XXVIII using, for example, diisobutylaluminum hydride in an organic solvent such as THF. A solution of the alcohol XXVIII in an organic solvent such as DMF with a base (e.g., imidazole) and t-butyldimethylsilyl chloride provides intermediate XXIX. Reaction of the triflate XXIX in DMSO/methanol as solvent with an organic base such as triethylamine, a phosphine such as diphenylphosphinoethane, a palladium II salt (e.g., palladium (II) acetate) and an atmosphere of carbon monoxide gives the ester XXX. This ester may be reduced to the corresponding alcohol XXXI (as before) then oxidised using, for example, manganese dioxide in an organic solvent (e.g., dichloromethane) to provide the aldehyde XXXII. A Wittig reaction between the aldehyde XXXII and an ylid derived from deprotonation of a phosphonium salt, R$^5$CH$_2$P(C$_6$H$_5$)$_3$X$^1$, using a strong base (e.g., n-BuLi) in an organic solvent such as THF affords the unsaturated intermediate XXXIII. Deprotection of the alcohol of XXXIII may be achieved by using a solution of tetrabutylammonium fluoride in THF to afford the alcohol XXXIV. Following the methodology described in Scheme II, the alcohol XXXIV can be transformed into compounds corresponding to formula IR.

The unsaturated intermediate XXXIII may be hydrogenated in an alcoholic solvent (e.g., methanol) using a catalyst such as 10% palladium on carbon and a hydrogen atmosphere to yield the saturated species XXXV. Deprotection of the alcohol of XXXV can be carried out as before to give the alcohol XXXVI. This alcohol XXXVI can be converted to compounds corresponding to formula IS using the procedures outlined for Scheme II.

Scheme VII

In Scheme VII the routes to prepare compounds of formula I where X=—CH$_2$S— are described. As the first step, the thiopyranoindole V (from Scheme I) can be dissolved in an organic solvent (e.g., DMF) and treated with an inorganic base such as NaH followed by the addition of dimethylthiocarbamoyl chloride to provide the intermediate XXXVII. Heating the intermediate XXXVII neat causes the compound to rearrange to give the thiophenol derivative XXXVIII. This compound when refluxed in a solution of sodium methoxide in methanol followed by subsequent reaction of the acid with thionyl chloride in methanol and then reduction of the disulfide bond (triphenylphosphine, 6N HCl in an organic solvent such as dioxane) gives the thiophenol XXXIX. The thiol group of intermediate XXXIX can be alkylated by stirring a solution of the thiophenol, an organic base such as triethylamine and an appropriate alkylating agent, R$^5$CH$_2$X$^1$, in a solvent such as THF. This procedure affords the ester XL which can be reduced (as before) to the alcohol XLI and then, using the procedures described for Scheme II, this can be converted to compounds corresponding to formula IT.

Scheme VIII

Scheme VIII describes the preparation of compounds of formula I by modification of compound I where Q=—CO$_2$H. For example, the acid of compound I (Q=CO$_2$H) can be treated with oxalyl chloride and a catalytic amount of DMF, in a suitable organic solvent (e.g., dichloromethane) and then, after addition of a hydroxylamine, HN(R$^6$)OH, this gives the hydroxamic acid XLII.

Stirring a solution of the acid of formula I (Q=—CO$_2$H), an appropriate carbodiimide such as 1-cyclohexyl-3-(2-morpholinoethyl)carbodiimide metho-p-toluenesulfonate, an organic base such as DMAP and a sulfonamide (R$^{12}$S(O)$_2$NH$_2$) in an organic solvent (e.g., dichloromethane) gives the acylsulfonamide XLIII. Alternatively the acid I (Q=—CO$_2$H) can be reacted with a chloroformate such as isobutylchloroformate in the presence of an organic base (e.g., triethylamine) and an appropriate organic solvent (e.g., THF). If a primary or secondary amine (HN(R$^6$)$_2$) is added (for example, ammonia gas) the product is an amide corresponding to formula LI. The amido-acid LII can result from the acid chloride derived from I (Q=—CO$_2$H), as prepared above, being treated with an amino ester in an organic solvent such as THF, followed by hydrolysis.

The aminoalkylamide LIII can be prepared using conditions similar to those used to prepare the acylsulfonamide XLIII except in the reaction the sulfonamide can be replaced with a diamine such as 1,3-diaminopropane. The aminoalkylamide LIII can then be further reacted with an acyl chloride (R$^7$COCl) to afford the compound LIV.

If the acid I (Q=—CO$_2$H) is dissolved in an organic solvent, for example THF, and treated sequentially with a chloroformate such as isobutylchloroformate, an organic base (e.g., triethylamine) and an aqueous solution of a tetraalkylammonium salt (e.g., tetrabutylammonium bromide) and sodium azide, the product (the acylazide XLIV) can be isolated. This compound upon heating in a suitable solvent such as chloroform can rearrange to yield the isocyanate XLV. The isocyanate XLV when heated with an organic acid such as acetic acid and an inorganic acid such as 6N HCl can give the amine XLVI. The amide XLVIII can be prepared from the amine XLVI using the method used to prepare the diamide LIV. Similarly, the compound XLIX can be prepared by reaction of the amine XLVI with ethyl oxalyl chloride. Hydrolysis of the ester of XLIX using standard conditions (previously described) then affords the acid L. Alternatively, stirring a solution of the amine XLVI and a sulfonyl chloride, R$^{12}$S(O)$_2$Cl, in an organic solvent (e.g., THF) can allow the preparation of compounds of structure XLVII.

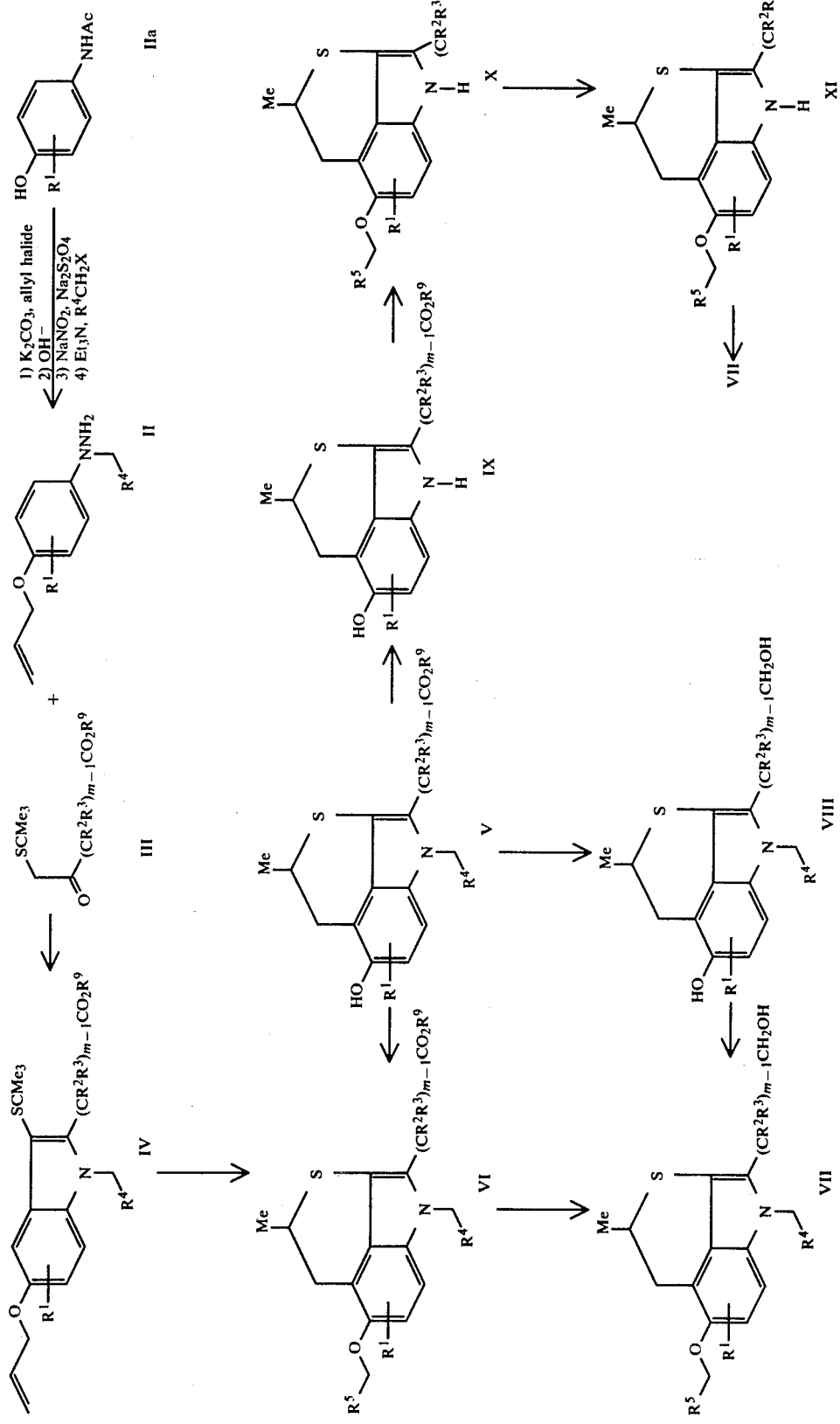

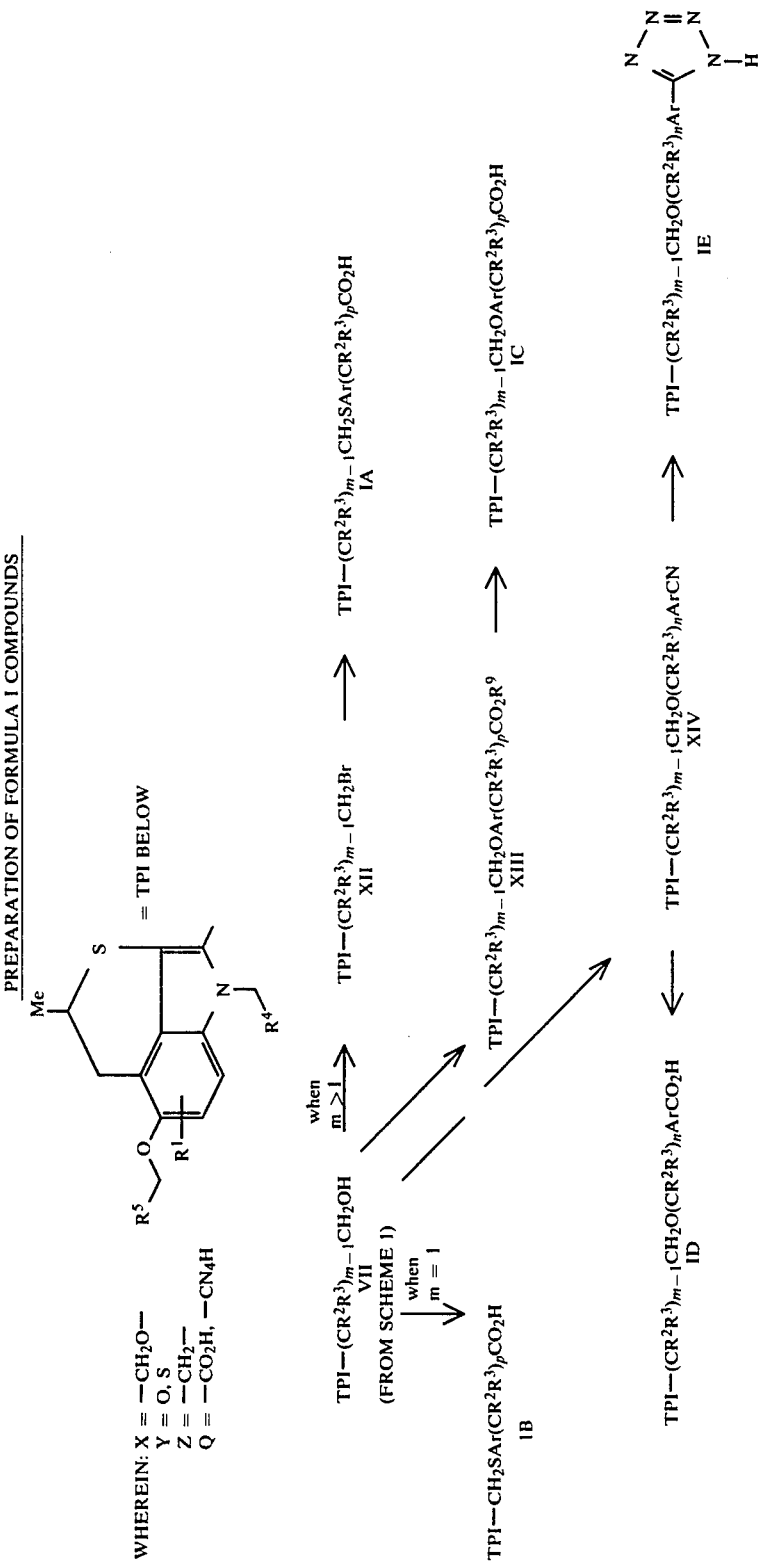

29 30
SCHEME III
PREPARATION OF FORMULA I COMPOUNDS
WHEREIN: X = —CH$_2$O—
Y = S
Z = —CH$_2$—
Q = —CO$_2$H, —CN$_4$H
n = 0
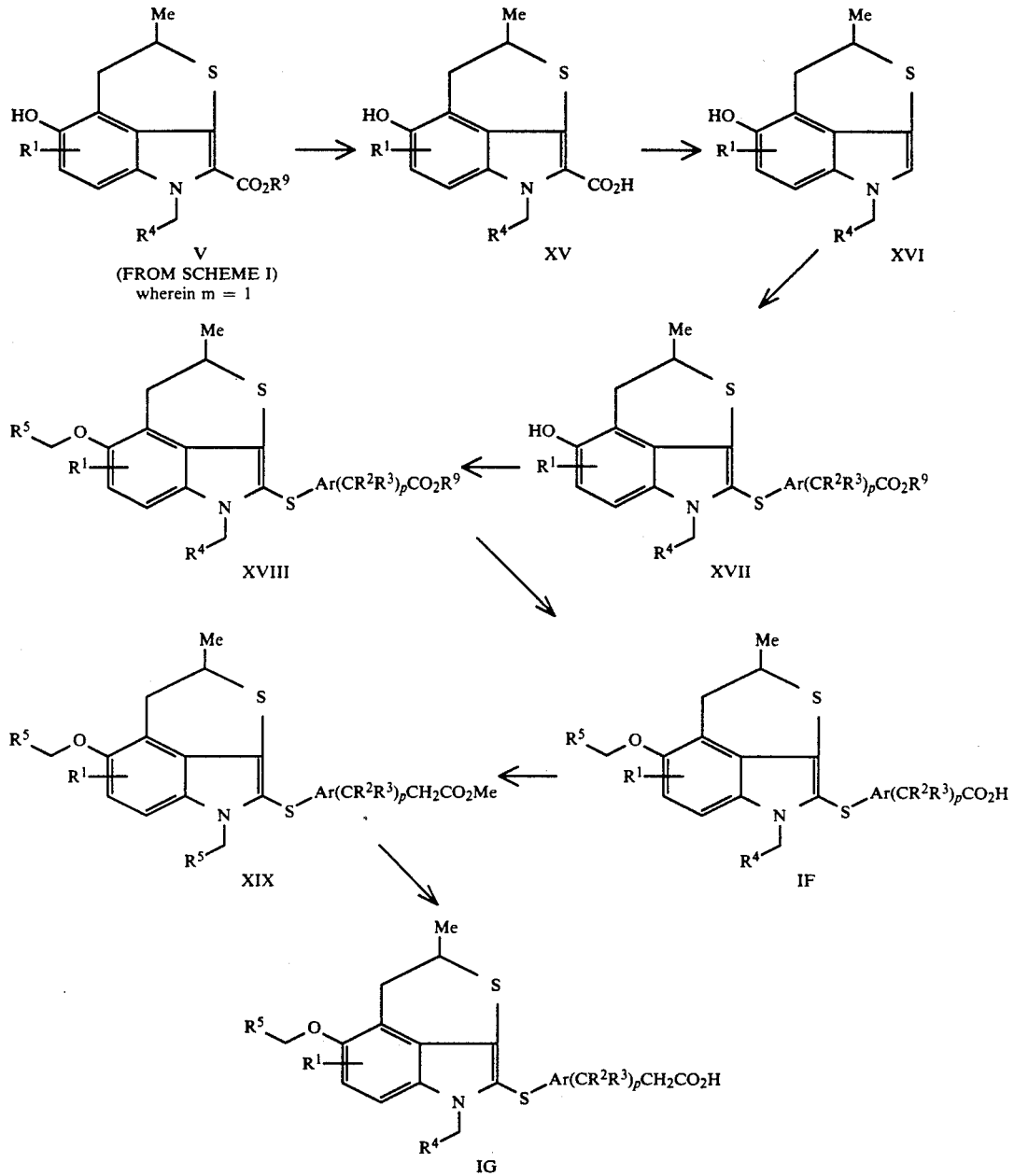
SCHEME IV
PREPARATION OF FORMULA I COMPOUNDS
WHEREIN: X = —CH$_2$O—
Y = a bond
Z = —CH$_2$—
Q = —CO$_2$H, —CN$_4$H -continued
SCHEME IV
PREPARATION OF FORMULA I COMPOUNDS
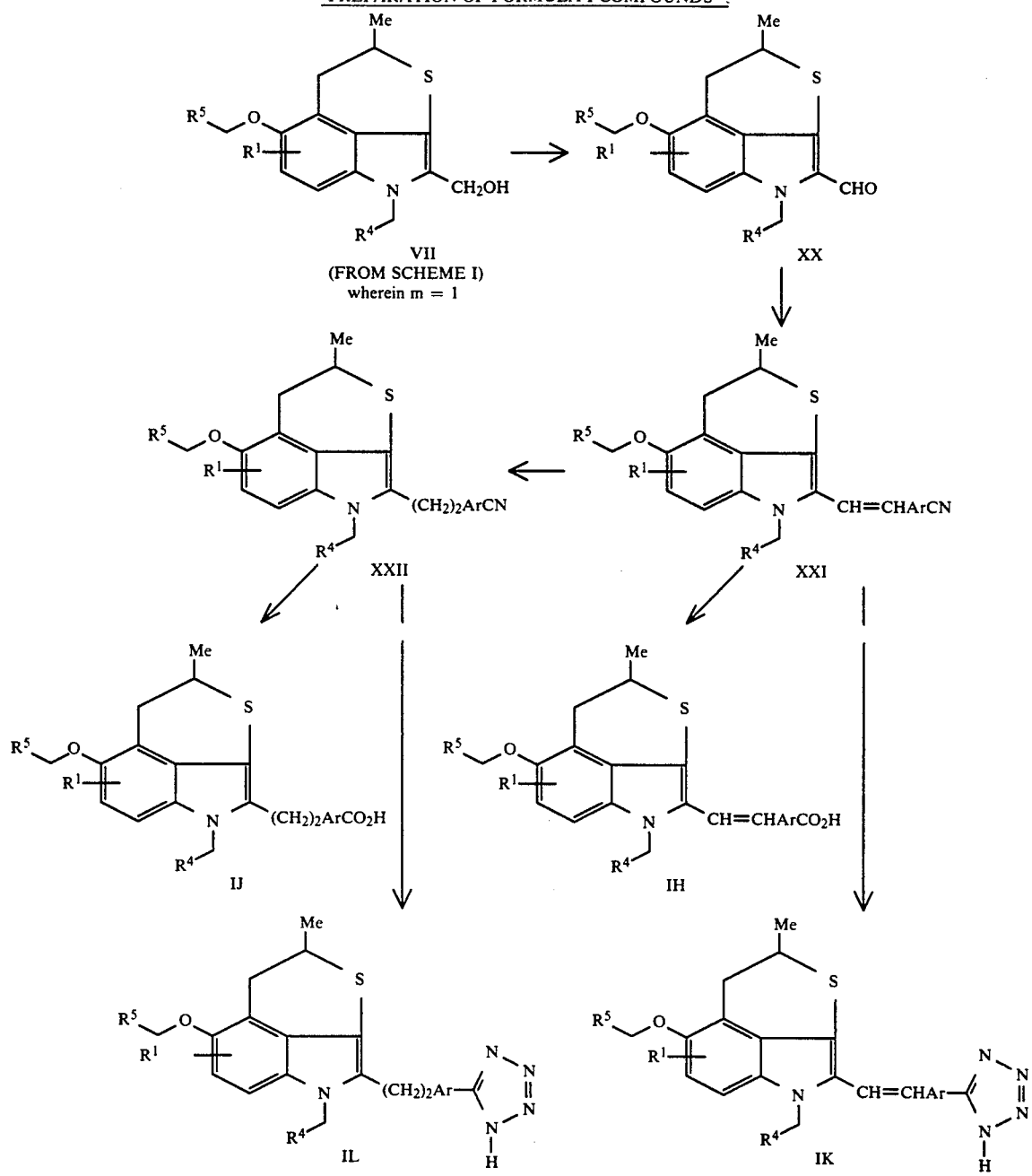

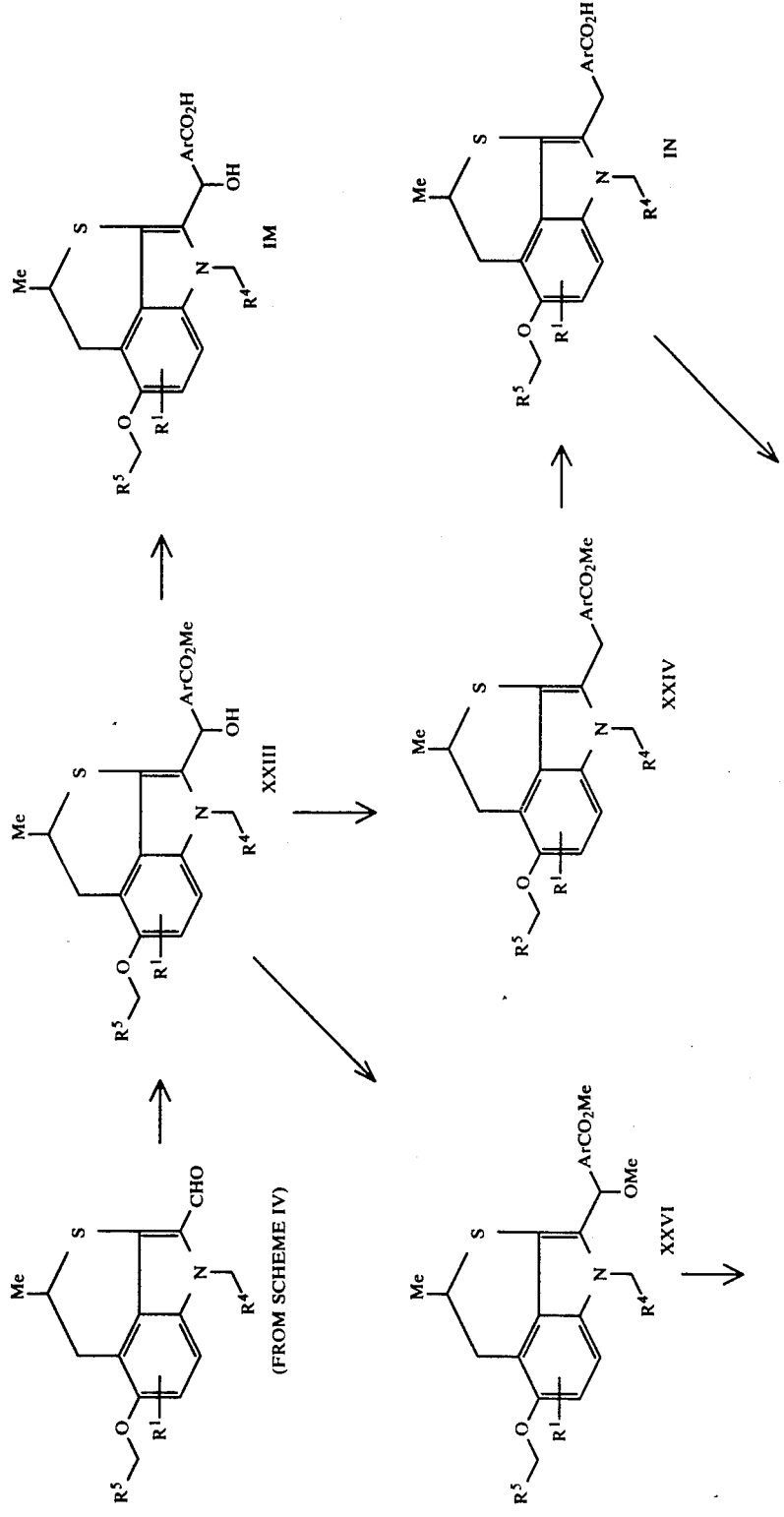

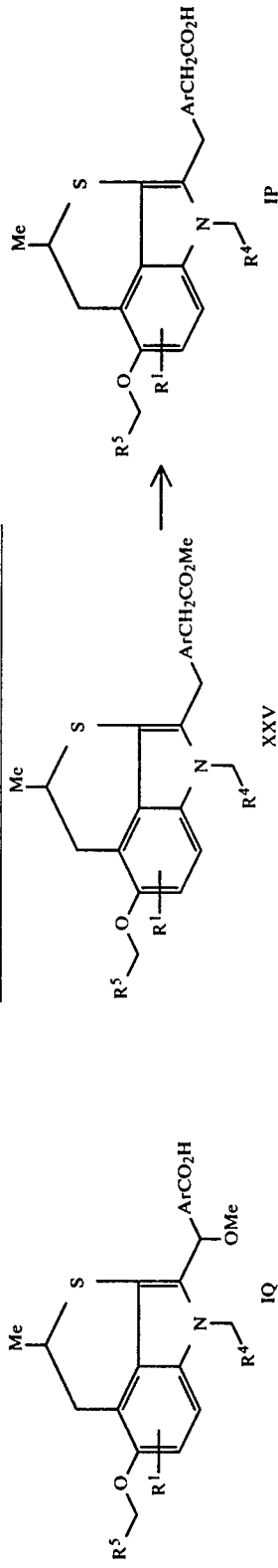

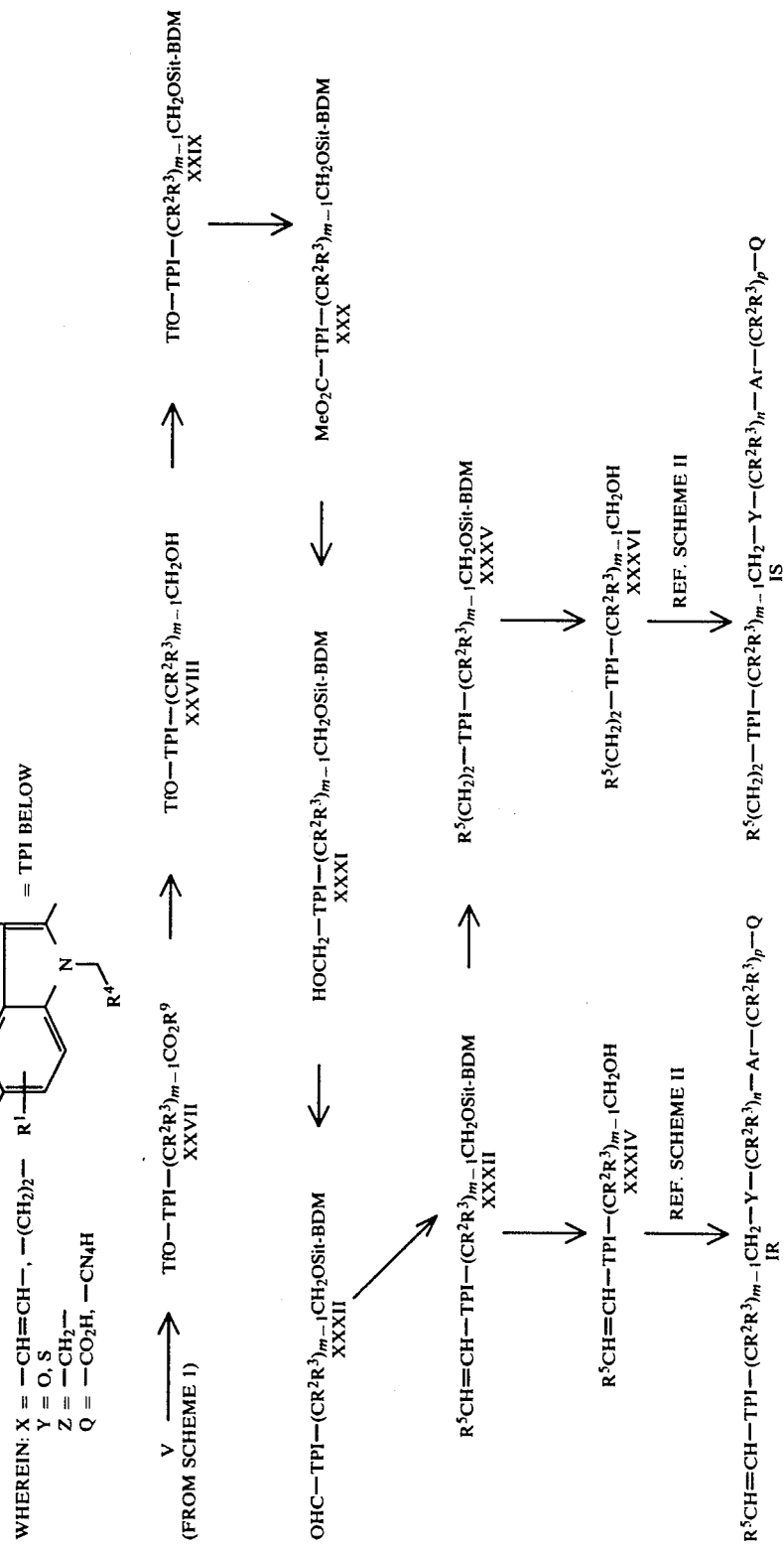

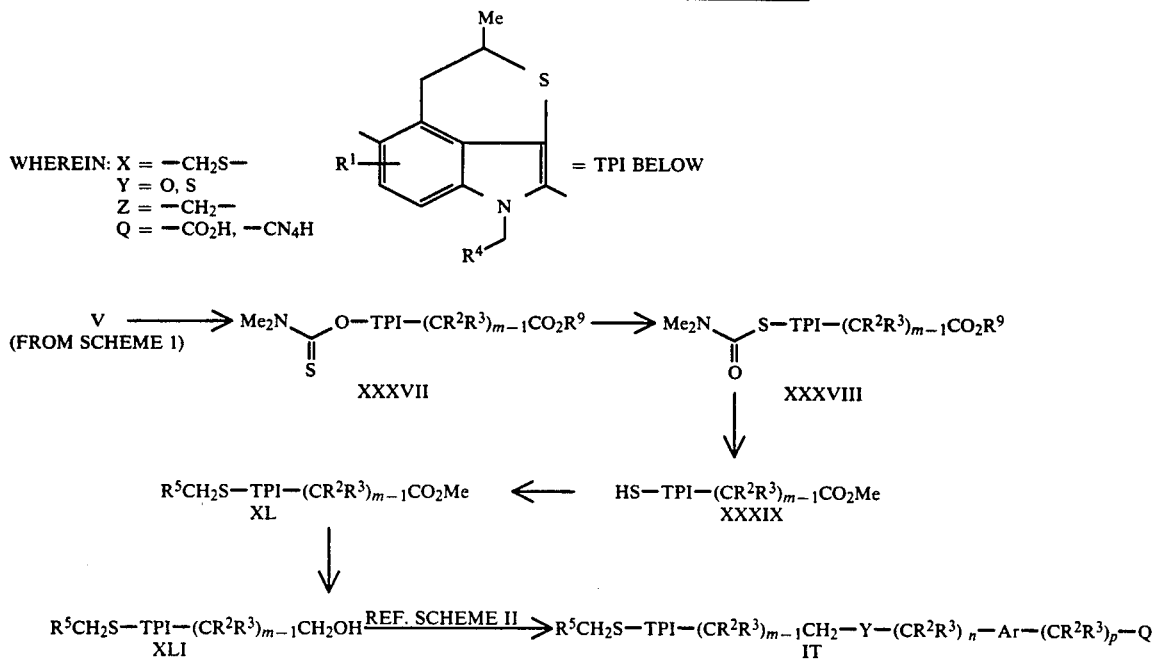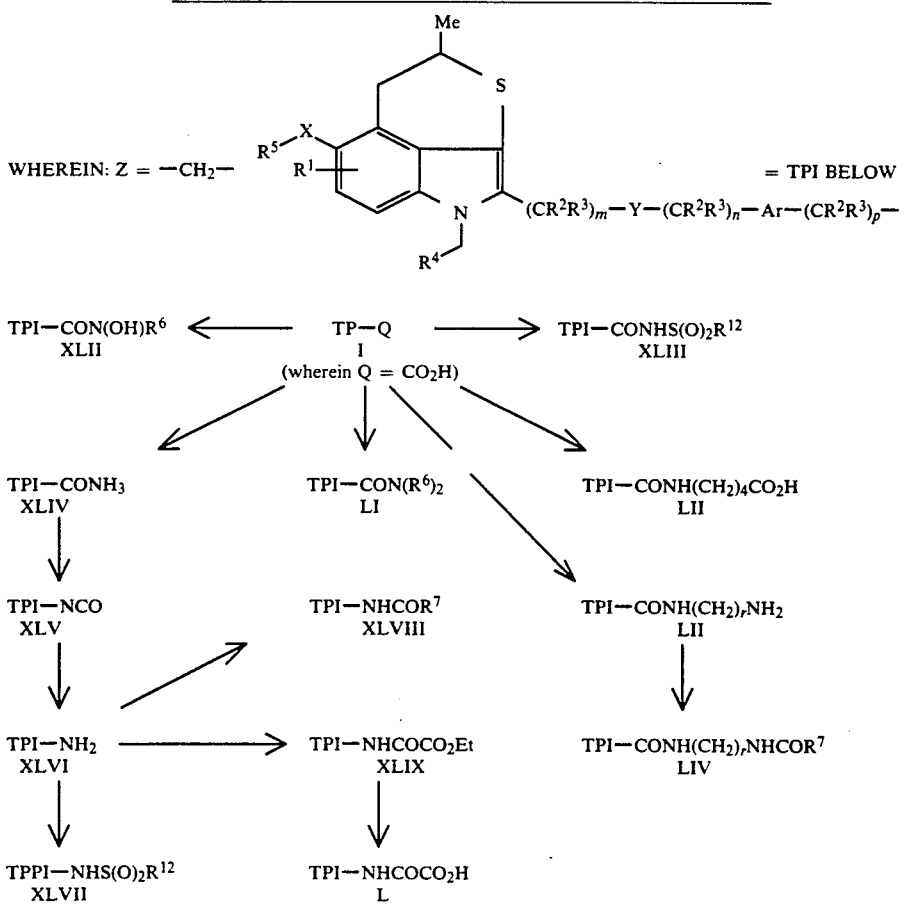

Assays for Determining Biological Activity

Compounds of Formula I can be tested using the following assays to determine their mammalian leukotriene biosynthesis inhibiting activity.

Human 5-Lipoxygenase Inhibitor Screen

Objective of the Assay: The objective of the assay is to select agents which specifically inhibit the activity of human 5-lipoxygenase using a $100,000 \times g$ supernatant fraction prepared from insect cells infected with recombinant baculovirus containing the coding sequence for human 5-lipoxygenase. Enzyme activity is measured spectrophotometrically from the optimal rate of conjugated diene formation ($A_{234}$) measured after the incubation of the enzyme with arachidonic acid in the presence of ATP, calcium ions and phosphatidylcholine.

Description of Procedure: The activity of 5-lipoxygenase is measured using a spectrophotometric assay and recombinant human 5-lipoxygenase as a source of enzyme. The $100,000 \times g$ fraction from S19 cells infected with the recombinant baculovirus rvH5LO(8-1) containing the coding region sequence for human 5-lipoxygenase is prepared as described by Denis et al. (J. Biol. Chem., 266, 5072-5079 (1991)). The enzymatic activity is measured, using a spectrophotometric assay from the optimal rate of conjugated diene formation ($A_{234}$) using the procedure described by Riendeau et al. (Biochem. Pharmacol. 38, 2323-2321, (1989)) with minor modifications. The incubation mixture contains 50 mM sodium phosphate pH 7.4, 0.2 mM ATP, 0.2 mM $CaCl_2$, 20 $\mu M$ arachidonic acid (5 $\mu L$ from a 100-fold concentrated solution in ethanol), 12 $\mu g/mL$ phosphatidylcholine, an aliquot of the $100,000 \times g$ fraction (2-10 $\mu L$) and inhibitor (0.5 mL final volume). Inhibitors are added as 500-fold concentrated solutions in DMSO. Reactions are initiated by the addition of an aliquot of the enzyme preparation and the rate of congugated diene formation is followed for 2 minutes at room temperature. The reactions are performed in semi-micro cuvettes (0.7 mL capacity, 10 mm path length and 4 mm internal width) and the absorbance changes are recorded with a Hewlett-Packard diode array spectrophotometer (HP 8452A) connected to the ChemStation using UV/VIS Kinetics Software (Hewlett-Packard). Enzymatic activity is calculated from the optimal rate of the reaction by a linear fit of the variation of $A_{234}$ during the first twenty seconds using the least square method for the equation $A_{234} = V_o t + A_o$ where $V_o$ is the rate, t is the time, and $A_o$ is the absorbance at zero time. The results are expressed as percentages of inhibition of the reaction rate relative to controls (typically between 0.15–0.21 AU/min) containing the DMSO vehicle.

Human Polymorphonuclear (PMN) Leukocyte LTB4 Assay

A. Preparation of Human PMN. Human blood is obtained by antecubital venepuncture from consenting volunteers who have not taken medication within the previous 7 days. The blood is immediately added to 10% (v/v) trisodium citrate (0.13M) or 5% (v/v) sodium heparin (1000 IU/mL). PMNs are isolated from anticoagulated blood by dextran sedimentation of erythrocytes followed by centrifugation through Ficoll-Hypaque (specific gravity 1.077), as described in Boyum, A. *Scand. J. Clin. Lab. Invest.*, 21 (Supp 97), 77 (1968). Contaminating erythrocytes are removed by lysis following exposure to ammonium chloride (0.16M) in Tris buffer (pH 7.65), and the PMNs resuspended at $5 \times 10^5$ cells/mL in HEPES (15 mM)-buffered Hanks balanced salt solution containing $Ca^{2+}$ (1.4 mM) and $Mg^{2+}$ (0.7 mM), pH 7.4. Viability is assessed by Trypan blue exclusion.

B. Generation and Radioimmunoassay of LTB4. PMNs (0.5 mL; $2.5 \times 10^5$ cells) are placed in plastic tubes and incubated (37° C., 2 min) with test compounds at the desired concentration or vehicle (DMSO, final concentration 0.2%) as control. The synthesis of LTB4 is initiated by the addition of calcium ionophore A23187 (final concentration 10 mM) or vehicle in control samples and allowed to proceed for 5 minutes at 37° C. The reactions are then terminated by the addition of cold methanol (0.25 mL) and samples of the entire PMN reaction mixture removed for radioimmunoassay of LTB4.

Samples (50 $\mu L$) of authentic LTB4 of known concentration in radioimmunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer are added to reaction tubes. Thereafter [$^3$H]-LTB4 (10 nCi in 100 $\mu L$ RIA buffer) and LTB4-antiserum (100 $\mu L$ of a 1:3000 dilution in RIA buffer) are added and the tubes vortexed. Reactants are allowed to equilibrate by incubation overnight at 4° C. To separate antibody-bound from free LTB4, aliquots (50 $\mu L$) of activated charcoal (3% activated charcoal in RIA buffer containing 0.25% Dextran T-70) are added, the tubes vortexed, and allowed to stand at room temperature for 10 minutes prior to centrifugation ($1500 \times g$; 10 min; 4° C.). The supernatants containing antibody-bound LTB4 are decanted into vials and Aquasol 2 (4 mL) added. Radioactivity is quantified by liquid scintillation spectrometry. The specificity of the antiserum and the sensitivity of the procedure have been described by Rokach et al., *Prostaglandins Leukotrienes and Medicine*, 13, 21 (1984). The amount of LTB4 produced in test and control (approx. 20 ng/$10^6$ cells) samples are calculated and inhibitory dose-response curves constructed using a four-parameter algorithm, from which these $IC_{50}$ values are determined.

Human Whole Blood Assay in Vitro for LTB4 Production

Fresh blood is collected in heparinized tubes by venipuncture from human volunteers. A 500 $\mu L$ aliquot is incubated with one of the test compounds at final concentrations varying from 3 nM to 3 mM at 37° C. for 15 min. Drug stock solutions are made up in DMSO and 1 $\mu L$ of the stock solution is added to each assay tube. The blood is then incubated with A23187 (in 5 $\mu L$ autologous plasma, 25 $\mu M$ final concentration) at 37° C. for 30 min. At the end of incubation, plasma is obtained ($12,000 \times g$, 15 min) and a 100 $\mu L$ aliquot is added to 400 $\mu L$ methanol for protein precipitation. The mixture is vortexed, centrifuged and the supernatant stored at −70° C. until assayed for LTB4 by standard RIA.

Asthmatic Rat Assay

Rats are obtained from an inbred line of asthmatic rats. Both female (190-250 g) and male (260-400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carried out in a clear plastic box with internal dimensions $10\times 6\times 4$ inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 mg/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1-4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65 HG, 400 cps) and given in a volume of 1 mL/kg body weight. For aerosol administration of compounds, a DeVilbiss ultrasonic nebulizer is utilized. Pretreatment periods vary from 5 minutes to 4 hours before the monkeys are challenged with aerosol doses of either leukotriene $D_4$ ($LTD_4$) or Ascaris antigen.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of $LTD_4$ or Ascaris antigen response by the test compound. For statistical analysis, paired t-test is used. (References: McFarlane, C. S. et al., Prostaglandins, 28: 173–182, 1984, McFarlane, C. S. et al., Agents Actions 22: 63–68, 1987.)

Prevention of Induced Bronchoconstriction in Allergic Sheep

A. Rationale. Certain allergic sheep with known sensitivity to a specific antigen (*Ascaris suum*) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods.

Animal Preparation: Adult sheep with a mean weight of 35 kg (range, 18 to 50 kg) are used. All animals used meet two criteria: a) they have a natural cutaneous reaction to 1:1,000 or 1:10,000 dilutions of *Ascaris suum* extract (Greer Diagnostics, Lenois, N.C.), and b) they have previously responded to inhalation challenge with *Ascaris suum* with both an acute bronchoconstriction and a late bronchial obstruction (Abraham, et. al., Am. Rev. Resp. Dis., 128, 839–44, 1983).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one mL of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). Testing of the pressure transcuder catheter system reveals no phase shift between pressure and flow to a frequency of 9 Hz. For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems: Aerosols of *Ascaris suum* extract (1:20) are generated using a disposable medical-nebulizer (Raindrop ®, Puritan Bennett), which produces an aerosol with a mass median aerodynamic diameter of 6.2 μM (geometric standard deviation, 2.1) as determined by an electric size analyzer (Model 3030; Thermal Systems, St. Paul, Minn.). The output from the nebulizer is directed into a plastic t-piece, one end of which is attached to the nasotracheal tube, the other end of which is conected to the inspiratory part of a Harvard respirator. The aerosol is delivered at a tidal volume of 500 mL of a rate of 20 per minute. Thus, each sheep receives an equivalent dose of antigen in both placebo and drug trials.

Experimental Protocol: Prior to antigen challenge baseline measurements of $SR_L$ are obtained, infusion of the test compound is started 1 hr prior to challenge, the measurement of $SR_L$ repeated and then the sheep undergoes inhalation challenge with *Ascaris suum* antigen. Measurements of $SR_L$ are obtained immediately after antigen challenge and at 1, 2, 3, 4, 5, 6, 6.5, 7, 7.5, and 8 hrs after antigen challenge. Placebo and drug tests are separated by at least 14 days. In a further study, sheep are given a bolus dose of the test compound followed by an infusion of the test compound for 0.5-1 br prior to Ascaris challenge and for 8 hrs after Ascaris as described above.

Statistical Analysis: A Kruskal-Wallis one way ANOVA test is used to compare the acute immediate responses to antigen and the peak late response in the controls and the drug-treated animals.

PREPARATION OF HYDRAZINES

Hydrazine 1: 1-(4-Chlorobenzyl)-1-(4-allyloxyphenyl)hydrazine

Step 1: 4-Allyloxyphenylhydrazine Hydrochloride

To a suspension of 4-allyloxyaniline hydrochloride (100 g) (Bull. Soc. Chim, France 2154-2157 (1962)) in $H_2O$ (1.4 L), cooled to 0° C., was added dropwise a solution of $NaNO_2$ in $H_2O$ (40 g/100 mL) and stirred for 15 minutes. The resulting cold diazonium salt was then cannulated into a stirred cold solution of $Na_2S_2O_4$ in $H_2O$ (516 g/3 L) and $Et_2O$ (3 L). The addition completed, the reaction mixture was stirred for 30 minutes and basified with 10N NaOH (540 mL). The $Et_2O$ layer was decanted, washed with brine, dried over $Na_2SO_4$, and HCl gas was passed through the ether solution to form the hydrochloride salt, which precipitated out. After filtration, the pure final product was obtained.

Step 2: 1-(4-Chlorobenzyl)-1-(4-allyloxyphenyl)hydrazine

To a suspension of the hydrazine hydrochloride of Step 1 (70 g) in toluene (1.2 L) was added $Et_3N$ (107 mL) followed by 4-chlorobenzyl chloride (61 g). The resulting mixture was heated at reflux for 2 hours. The reaction mixture was cooled and $Et_2O$ (1.2 L) was added. The triethylammonium hydrochloride salt was filtered off, and the filtrate concentrated under vacuum. The crude residue was purified by chromatography on a bed of silica gel eluting with hexane-EtOAc (6:4) to afford the pure title product as an oil.

Hydrazine 2: 1-(3-Chlorobenzyl)-1-(4-allyloxyphenyl)hydrazine

Following the procedure described for Hydrazine 1, Step 2, but substituting 3-chlorobenzyl chloride for 4-chlorobenzyl chloride as starting material, the title compound was obtained as an oil.

Hydrazine 3: 1-(4-Fluorobenzyl)-1-(4-allyloxyphenyl)hydrazine

Following the procedure described for Hydrazine 1, Step 2, but substituting 4-fluorobenzyl chloride for 4-chlorobenzyl chloride as starting material, the title compound was obtained as an oil.

Hydrazine 4: 1-(3-Fluorobenzyl)-1-(allyloxyphenyl)hydrazine

Following the procedure described for Hydrazine 1, Step 2, but substituting 3-fluorobenzyl chloride for 4-chlorobenzyl chloride as starting material, the title compound was obtained as an oil.

PREPARATION OF KETONES

Ketone 1: Ethyl 3-(t-butylthio)-2-oxopropanoate

To a solution of ethyl bromopyruvate (1 eq) and 2-methyl-2-propanethiol (1.2 eq) was added dropwise $Et_3N$ (1.5 eq) in THF at 0° C. under nitrogen and the mixture was stirred for 4 hours. The mixture was filtered and the solvent removed in vacuo. The crude oily residue was used as such for the next step.

Ketone 2: Ethyl 4-(t-butylthio)-3-oxobutanoate

Following the procedure described for Ketone 1, but substituting ethyl 4-chloroacetoacetate for ethyl bromopyruvate as starting material the title compound was obtained as an oil.

PREPARATION OF PHENOLS

Phenol 1: Methyl 2-hydroxyphenylacetate

A suspension of 2-hydroxyphenylacetate acid (1.2 g) (Aldrich) in EtOAc (50 mL) was treated with excess ethereal diazomethane until the acid was consumed (TLC). The resulting solution was filtered through celite, the solvent removed, and the residue triturated with hexane/ether 10:1 to provide the title compound as a solid.

Phenol 2: Methyl 2-hydroxybenzoate

Available from Lancaster Synthesis.

Phenol 3: Methyl 3-hydroxybenzoate

Available from Aldrich Chemical Company.

Phenol 4: 2-hydroxybenzonitrile

Available from Aldrich Chemical Company.

Phenol 5: Methyl 5-chloro-2-hydroxybenzoate

Following the procedure described for Phenol 1 but substituting 5-chloro-2-hydroxybenzoic acid (Aldrich) for 2-hydroxyphenylacetic acid as starting material, the title compound was obtained as a solid.

Phenol 6: Methyl 2-(2-hydroxyphenyl)propanoate

This compound was prepared as described in CA: 87, 68074d (1977).

Phenol 7: Methyl 2-(2-hydroxyphenyl)butanoate

Step 1: Methyl (2-trimethylsilyloxyphenyl)acetate

To a solution of methyl (2-hydroxyphenyl)acetate (1.5 g) in $CH_2Cl_2$ (10 mL) and pyridine (10 mL) was added slowly chlorotrimethylsilane (1.26 mL). The mixture was stirred for 18 hours, then most of the solvent was evaporated under reduced pressure and the residue was chromatographed on silica gel using 15% of EtOAc in hexane to afford 1.3 g of methyl (2-trimethylsilyloxyphenyl)acetate.

Step 2: Methyl 2-(2-hydroxyphenyl)butanoate

To a solution of diisopropylamine (0.46 mL) in THF (3 mL) at 0° C. was added 1.6M BuLi in hexane (2.01 mL). After stirring for 30 minutes at 0° C., 2.74 mL of this solution was added to a solution of methyl (2-trimethylsilyloxyphenyl)acetate from Step 1, (357 mg) in THF (5 mL) at 0° C. After 20 minutes, ethyl iodide (0.144 mL) was added and the mixture was stirred for 18 hours at r.t. Then, 2 mL of 1N HCl was added and the resulting mixture was stirred for 30 minutes, extracted with EtOAc, washed twice with brine, dried over $MgSO_4$, filtered, and evaporated to dryness, giving the title compound.

Phenol 8: Methyl 3-hydroxy-2-naphthoate

Following the procedure described for Phenol 1 but substituting 3-hydroxy-2-naphthoic acid (Aldrich) for 2-hydroxyphenyl acetic acid as starting material, the title compound was obtained as a solid.

PREPARATION OF ALKYLATING REAGENTS

Halide 19: 3-Cyclohexylpropyl iodide

Using the procedure described in J. Am. Chem. Soc., 90, 6225 (1968), this halide was obtained from 3-cyclohexylpropyl chloride (Aldrich) by displacement of the chloride by NaI.

Halide 20: 2-Thienylmethyl methanesulfonate

Using the procedure described in J. Org. Chem., 35, 3195 (1970), this sulfonate was obtained from 2-thiophene methanol (Aldrich) by mesylation with MsCl.

Halide 23: 5-Phenyl-2-picolyl chloride

Step 1: 5-Phenyl-2-picoline

A suspension of 100 g of wet Raney Nickel in 1.5 L of dodecanol in a three-neck round bottom flask equipped with a Dean Stark apparatus was heated until the temperature reached 130° C., then 3-phenylpyridine (Aldrich) was added and the reaction was heated at 190°-200° C. for 6 hours. During the reaction, $H_2O$ was constantly eliminated. When the reaction was over, half of the dodecanol was removed by distillation. After cooling the reaction mixture to room temperature, 200 mL of $H_2O$ and 400 mL of hexane were added, the mixture was shaken, and the hexane layer decanted. This process was repeated several times. The combined hexane fractions were washed with 1N HCl until the disappearance of 5-phenyl-2-picoline from the organic phase. The combined aqueous layers were filtered, washed with hexane, basified with 10N NaOH, and extracted with $CH_2Cl_2$. The organic layer was washed with $NH_4OAc$ (25%), dried over $MgSO_4$, and evaporated to dryness. The crude residue was then distilled under vacuum (100° C. at 0.1 mm of Hg) to afford the pure title product.

Step 2: 5-Phenyl-2-picolyl chloride

Method A

To a solution of 6.2 g 5-phenyl-2-picoline in 250 mL of $CCl_4$ were added 5.85 g of N-chlorosuccinimide and 100 mg of benzoylperoxide. The reaction was then heated to reflux and irradiated with a 225 watt lamp for 5 hours. After cooling, $Et_2O$ was added, the solid filtered, and the filtrate was evaporated to dryness. The crude residue was chromatographed on silica gel (hexane/EtOAc 9:1) to give the pure title product.

Method B

Step 1: 5-Phenyl-2-picoline N-oxide

To a solution of 100 g 5-phenyl-2-picoline in 170 mL of glacial HOAc was added 30% $H_2O_2$ and the resulting solution was heated at 70° C. overnight. After the reaction mixture was cooled to room temperature, 1 g of 10% Pd/C was added to destroy any excess of $H_2O_2$. The reaction mixture was then filtered on celite, washed with toluene, and the filtrate was evaporated to dryness affording a yellow solid residue. The crude material was swished with a mixture of $Et_2O$/EtOAc (10:1) and filtered to afford the pure title product as a white solid, m.p.: 91° C.

Step 2: 5-Phenyl-2-picolyl chloride

To a solution of 75 g 5-phenyl-2-picoline N-oxide from Step 1 in 375 mL of $CH_2Cl_2$ were added simultaneously a solution of 41.5 mL phosphoryl chloride in 150 mL of $CH_2Cl_2$ and a solution of 62 mL $Et_3N$ in 150 mL of $CH_2Cl_2$. The rate of addition was adjusted so that the reaction reached reflux temperature. The addition completed, the reaction was poured into a solution of $NH_4OAc$ (25%), stirred 30 minutes, and extracted with EtOAc. The organic layer was dried over $MgSO_4$, filtered on a silica gel bed, and evaporated to dryness. The resulting solid was recrystallised from petroleum ether (30°-60° C.) to afford pure title product, m.p.: 73° C. The filtrate was chromatographed on silica gel (hexane/EtOAc 9:1) to give the title product along with 4-chloro-5-phenyl-2-picoline and 6-chloro-5-phenyl-2-picoline.

Halide 24: 2-(1-Adamantyl)ethyl bromide

Using the procedure described in Can. J. Chem., 46, 86 (1968), this bromide was obtained from 2-(1-adamantyl)ethanol (Aldrich) by the conversion of the hydroxyl group to the bromide by $CBr_4$ and triphenylphosphine.

Halide 28: 2-Chloromethyl-5-phenylpyridine N-oxide

Following the procedure described in Halide 23, Step 2, Method B, Step 1, but substituting 5-phenyl-2-picolyl chloride (Halide 23) for 5-phenyl-2-picoline as starting material, the title compound was obtained as a solid.

Halide 32: 2-Phenyl-3-picolyl chloride

Following the procedure described in Halide 23, Step 2, Method A, but substituting 2-phenyl-3-picoline (Aldrich) for 5-phenyl-2-picoline as starting material the title compound was obtained as a solid.

Halide 39: 6-Chloro-5-phenyl-2-picolyl chloride

Following the procedure described in Halide 23, Step 2, Method B, but substituting 6-chloro-5-phenyl-2-picoline (from Halide 23, Step 2, Method B, Step 2) for 5-phenyl-2-picoline as starting material, the title compound was obtained as a solid.

Halide 40: 4-Chloro-5-phenyl-2-picolyl chloride

Following the procedure described in Halide 23, Step 2, Method B, but substituting 4-chloro-5-phenyl-2-picoline (from Halide 23, Step 2, Method B, Step 2) for 5-phenyl-2-picoline as starting material, the title compound was obtained as a solid.

Halide 41: 5-(t-Butyldiphenylsilyloxy)-2-picolyl chloride

Step 1: 5-(t-Butyldiphenylsilyloxy)-2-picoline

A solution of 10.9 g 5-hydroxypicoline, 8.85 g imidazole, and 29.9 mL t-butyldiphenylsilylchloride in 500 mL of $CH_2Cl_2$ was stirred for 4 days at 25° C. The mixture was washed with $H_2O$, brine, dried over $MgSO_4$, and concentrated under vacuum. The crude product was purified by silica gel chromatography (EtOAc/Hexane 10:90) to afford the pure title compound as an oil.

Step 2: 5-(t-Butyldiphenylsilyloxy)-2-picolyl chloride

Following the procedure described in Halide 23, Step 2, Method A, but substituting 5-(t-butyldiphenylsilyloxy)-2-picoline (from Step 1) for 5-phenyl-2-picoline as starting material, the title compound was obtained.

Halide 42: 5-Benzyl-2-picolyl chloride

Following the procedure described in Halide 23, Steps 1 and 2, Method B, but substituting 3-benzylpyridine (Aldrich) for 3-phenylpyridine as starting material the title compound was obtained.

Halide 43: 5-(4-Chlorophenyl)-2-picolyl chloride

Step 1: 5-Trifluoromethanesulfonyloxy-2-picoline

To a solution of 5 g of 3-hydroxy-6-methylpyridine in 100 mL of $CH_2Cl_2$ at 0° C. was added successively 7.7 mL of $Et_3N$ and 8.1 mL of $Tf_2O$. The reaction was stirred at room temperature for 30 minutes, then diluted with more $CH_2Cl_2$ (220 mL). The organic phase was washed successively with 1N HCl, brine, dried over $MgSO_4$, filtered, and concentrated to give after purification using flash chromatography on silica gel (hexane:EtOAc 65:35) the title compound.

Step 2: 5-(4-Chlorophenyl)-2-picoline

The trifluoromethane sulfonate from Step 1 (500 mg) was dissolved in 10 mL of toluene, 5 mL of EtOH, and 1.6 mL of 2M aqueous $Na_2CO_3$. Then 203 mg LiCl, 411 mg of 4-chlorobenzeneboronic acid (Lancaster) and 832 mg of tetrakis (triphenylphosphine) palladium were added successively. The resulting reaction mixture was heated up to 90°–95° C. for 1 hour. The reaction mixture was cooled down to room temperature, EtOAc was added, and the organic phase was washed with 1N NaOH, brine, dried over $MgSO_4$, filtered, and concentrated. Purification by flash chromatography using hexane: EtOAc 3:2 gave the title compound.

Step 3: 5-(4-Chlorophenyl)-2-picolyl chloride

Following the procedure described in Halide 23, Step 2, Method B, but substituting 5-(4-chlorophenyl)-2-picoline (from Step 2) for 5-phenyl-2-picoline as starting material, the title compound was obtained.

Halide 46: 2-Chloromethyl-1,8-naphthyridine

Following the procedure described in Halide 23, Step 2, Method A, but substituting 2-methyl-1,8-naphthyridine (Chem. Pharm. Bull., 19, 1857 (1971)) for 5-phenyl-2-picoline as starting material, the title compound was obtained.

Halide 47: 4-(2-Pyridyl)benzyl chloride

Following the procedure described in Halide 23, Step 2, Method A, but substituting 2-(4-tolyl)pyridine (Aldrich) for 5-phenyl-2-picoline as starting material, the title compound was obtained as a solid.

Halide 54: 5-(1-Naphthyl)-2-picolyl chloride

Step 1: 5-(1-Naphthyl)-2-picoline

Following the procedure described in Halide 43, Step 2, but substituting 1-naphthaleneboronic acid (Lancaster) for 4-chlorobenzeneboronic acid as starting material, the title compound was obtained.

Step 2: 5-(1-Naphthyl)-2-picolyl chloride

Following the procedure described in Halide 23, Step 2, Method B, but substituting 5-(1-naphthyl)-2-picoline (from Step 1) for 5-phenyl-2-picoline as starting material, the title compound was obtained.

Halide 55: 5-(4-Methoxyphenyl)-2-picolyl chloride

Step 1: 5-(4-Methoxyphenyl)-2-picoline

Following the procedure described in Halide 43, Step 2, but substituting 4-methoxybenzene boronic acid (Lancaster) for 4-chlorobenzeneboronic acid as starting material, the title compound was obtained.

Step 2: 5-(4-Methoxyphenyl)-2-picolyl chloride

Following the procedure described in Halide 23, Step 2, Method B, but substituting 5-(4-methoxyphenyl)-2-picoline (from Step 1) for 5-phenyl-2-picoline as starting material, the title compound was obtained.

Halide 57: 5-Chloromethyl-2-phenylfuro[3,2b]pyridine

Following the procedure described in Halide 23, Step 2, Method B, but substituting 5-methyl-2-phenylfuro[3,2-b]pyridine (Synthesis, 749–751 (1986)) for 5-phenyl-2-picoline as starting material, the title compound was obtained.

Halide 59: 3-(4-Methoxytetrahydropyran-4-yl)benzyl chloride

Step 1: 3-Bromobenzyl alcohol-THP ether

A solution of 3-bromobenzyl alcohol (85 g, 436 mmol), 3,4-dihydro-2H-pyran (44 g, 520 mmol), and anhydrous p-TSA (1.0 g, 6 mmol) in $CH_2Cl_2$ (800 mL) was stirred at r.t. for 18 hours. The mixture was concentrated and the residue chromatographed on silica gel using 5% EtOAc in hexane as eluent to obtain 107 g (90%) of the title compound as an oil.

Step 2: 3-(4-Hydroxytetrahydropyran-4-yl)benzyl alcohol-THP ether

To a mechanically stirred solution of 3-bromobenzyl alcohol-THP ether from Step 1 (107 g, 394 mmol) in THF (1 L) at −78° C. and under a nitrogen atmosphere was added at a rapid dropwise rate 2.5M nBuLi in hexane (190 mL, 472 mmol). The mixture was stirred at −78° C. for 1.5 hours and then was added rapidly dropwise to tetrahydro-4H-pyrano-4-one (50 g, 500 mmol). The mixture was allowed to gradually rise to −30° C. and then excess saturated $NH_4Cl$ solution was added slowly. $Et_2O$ and brine were then added. The organic layer was separated, dried ($MgSO_4$), filtered, and concentrated in vacuum. The residue was chromatographed on silica gel using 50% EtOAc in hexane to obtain 82 g (71%) of the title compound as an oil.

Step 3: 3-(4-Methoxytetrahydropyran-4-yl)benzyl alcohol-THP ether

To a solution of 3-(4-hydroxytetrahydropyran-4-yl)benzyl alcohol-THP ether from Step 2 (61 g, 208 mmol) in DMF (400 mL) at r.t. under a nitrogen atmosphere was added in portions NaH (7.2 g, 300 mmol). After stirring for 1 hour, the mixture was cooled to 0° C. and MeI (42.5 g, 300 mmol) was added. The mixture was gradually allowed to warm up to r.t. over 18 hours. Excess $H_2O$ and $Et_2O$ were added. The organic layer was separated, dried ($MgSO_4$), filtered, and concentrated. The residue was chromatographed on silica gel using 50% EtOAc in hexane as eluent to obtain 48.6 g (76%) of the title compound as an oil.

Step 4: 3-(4-Methoxytetrahydropyran-4-yl)benzyl alcohol

To a solution of 3-(4-methoxytetrahydropyran-4-yl)benzyl alcohol-THP ether from step 3 (48 g, 156 mmol) in MeOH (150 mL) was added 3N HCl (50 mL) in one portion. The mixture was left standing at r.t. for 2 hours and then concentrated in vacuo. The residue was partitioned between $Et_2O$ and brine. The organic layer was separated, dried ($MgSO_4$), filtered, and concentrated in vacuo to obtain 28.7 g (82%) of the title compound as an oil which was used as such in the next reaction.

Step 5: 3-(4-Methoxytetrahydropyran-4-yl)benzyl chloride

Carbon tetrachloride (30.3 g, 198 mmol) was added dropwise over 20 minutes to a solution of 3-(4-methxytetrahydropyran-4-yl)benzyl alcohol from Step 4 (29.3 g, 132 mmol) and HMPA (32.2 g, 198 mmol) in THF (400 mL) at 0°–5° C. The mixture was stirred for 10 minutes and then concentrated. Excess $Et_2O$ was added and the mixture filtered through a celite pad. The filtrate was concentrated and chromatographed on silica gel using 20% EtOAc in hexane as eluent to obtain 24 g (81%) of the title compound as an oil.

PREPARATION OF ESTERS

Ester 1: Ethyl [1-(4-chlorobenzyl)-4-methyl-6-hydroxy-4,5-dihydro-1H-thiopyrano-[2,3,4-c,d]indol-2-yl]carboxylate

Step 1: Ethyl [1-(4-chlorobenzyl)-3-t-butylthio-5-allyloxyindol-2-yl]carboxylate A solution of ethyl 3-(t-butylthio)-2-oxopropanoate (18.6 g), 1-(4-chlorobenzyl)-1-(4-allyloxyphenyl)hydrazine hydrochloride (26.3 g), and NaOAc (15 g) in 300 mL toluene and 150 mL HOAc was stirred at room temperature under nitrogen for 16 hours then at 70° C. for 2 hours. The mixture was cooled, poured onto $H_2O$, extracted (3×) with EtOAc and, the organic layers then washed successively with sat'd. $NaHCO_3$ and brine. After drying over $MgSO_4$, the solution was filtered and evaporated, and the residue chromatographed (silica gel; hexane/EtOAc 4:1) to afford the title compound.

Step 2: Ethyl [1-(4-chlorobenzyl)-4-methyl-6-hydroxy-4,5-dihydro-1H-thiopyrano[2,3,4-c,d]indol-2-yl]carboxylate The allyl ether (34 g) from Step 1 in 250 mL 1,2-dichlorobenzene was heated to 200° C. under $N_2$ for 7 hours. After cooling the solution to 150° C., p-TSA (900 mg) was added and the reaction stirred for 30 minutes before being allowed to cool to room temperature. The solution was purified directly by chromatography (silica gel; hexane/EtOAc 19:1 then 2:1) to give the title compound as a solid.

Ester 2: Ethyl [1-(3-chlorobenzyl)-4-methyl-6-hydroxy-4,5-dihydro-1H-thiopyrano[2,3,4-c,d]indol-2-yl]carboxylate Following the procedures described for Ester 1, Steps 1 and 2, but substituting 1-(3-chlorobenzyl)-1-(4-allyloxyphenyl)hydrazine hydrochloride for 1-(4-chlorobenzyl)-1-(4-allyloxyphenyl)hydrazine hydrochloride in Step 1, the title compound was obtained.

Ester 3: Ethyl [1-(4-fluorobenzyl)-4-methyl-6-hydroxy-4,5-dihydro-1H-thiopyrano[2,3,4-c,d]indol-2-yl]carboxylate Following the procedures described for Ester 1, Steps 1 and 2, but substituting 1-(4-fluorobenzyl)-1-(4-allyloxyphenyl)hydrazine hydrochloride for 1-(4-chlorobenzyl)-1-(4-allyloxyphenyl)hydrazine hydrochloride in Step 1, the title compound was obtained.

Ester 4: Ethyl [1-(4-chlorobenzyl)-4-methyl-6-hydroxy-4,5-dihydro-1H-thiopyrano-[2,3,4-c,d]indol-2-yl]acetate Following the procedures described for Ester 1, Steps 1 and 2, but substituting ethyl 4-(t-butylthio)-3-oxobutanoate for ethyl 3-(t-butylthio)-2-oxopropanoate in Step 1, the title compound was obtained.

Ester 5: Ethyl [1-(3-chlorobenzyl)-4-methyl-6-hydroxy-4,5-dihydro-1H-thiopyrano[2,3,4-c,d]indol-2-yl]acetate Following the procedures described for Ester 1, Steps 1 and 2, but substituting ethyl 4-(t-butylthio)-3-oxobutanoate for ethyl 3-(t-butylthio)-2-oxopropanoate and 1-(3-chlorobenzyl)-1-(4-allyloxyphenyl)hydrazine hydrochloride for 1-(4-chlorobenzyl)-1-(4-allyloxyphenyl)hydrazine hydrochloride in Step 1, the title compound was obtained.

Ester 6: Ethyl [1-(4-fluorobenzyl)-4-methyl-6-hydroxy-4,5-dihydro-1H-thiopyrano[2,3,4-c,d]indol-2-yl]acetate Following the procedures described for Ester 1, Steps 1 and 2, but substituting ethyl 4-(t-butylthio)-3-oxobutanoate for ethyl 3-(t-butylthio)-2-oxopropanoate and 1-(4-fluorobenzyl)-1-(4-allyloxyphenyl)hydrazine hydrochloride for 1-(4-chlorobenzyl)-1-(4-allyloxyphenyl)hydrazine hydrochloride in Step 1, the title compound was obtained.

Ester 7: Ethyl [1-(3-fluorobenzyl)-4-methyl-6-hydroxy-4,5-dihydro-1H-thiopyrano[2,3,4-c,d]indol-2-yl]acetate Following the procedures described for Ester 1, Steps 1 and 2, but substituting ethyl 4-(t-butylthio)-3-oxobutanoate for ethyl 3-(t-butylthio)-2-oxopropanoate and 1-(3-fluororobenzyl)-1-(4-allyloxyphenyl)hydrazine hydrochloride for 1-(4-chlorobenzyl)-1-(4-allyloxy-phenyl)hydrazine hydrochloride in Step 1, the title compound was obtained.

The invention is further defined by reference to the following examples, which are intended to be illustrative and not limiting. All temperatures are in degrees Celsius.

EXAMPLE 1

2-[1-(4-Chlorobenzyl)-4-methyl-6-(5-phenylpyridin-2-ylmethoxy)-4,5-dihydro-1H-thiopyrano[2,3,4-c,d]indol-2-ylmethylthio]benzoic acid

Step 1: Ethyl [1-(4-chlorobenzyl)-4-methyl-6-(5-phenylpyridin-2-ylmethoxy)-4,5-dihydro-1H-thiopyrano[2,3,4-c,d]indol-2-yl]carboxylate A solution of the Ester 1 (22 g), 5-phenyl-2-picolylchloride (12.2 g), and $Cs_2CO_3$ (21.4 g) in 250 mL $CH_3CN$ was stirred overnight at r.t. then heated to 70° C. for 3 hours. The solution was cooled, THF added, followed by 1N HCl and EtOAc. After two further extractions using 1:1 THF/EtOAc, the combined organic layers were washed (2× brine), dried ($MgSO_4$), and concentrated. The residue was swished with $Et_2O$ and filtered to give the title compound as a solid.

Step 2: [1-(4-Chlorobenzyl)-4-methyl-6-(5-phenylpyridin-2-ylmethoxy)-4,5-dihydro-1H-thiopyrano[2,3,4-c,d]indol-2-yl]methanol The ester (13 g) from Step 1 was dissolved in 400 mL THF at 0° C. under nitrogen and $LiAlH_4$ (1.3 g) was added in portions. After 30 minutes, the reaction was warmed to r.t. then poured onto ice, acidified with 1N HCl, and the precipitate collected by filtration. The precipitate was dissolved in THF/EtOAc and washed twice with brine, dried ($MgSO_4$), and evaporated. Trituration of the residue with $Et_2O$ provided the title compound as a solid.

Step 3: 2-[1-(4-Chlorobenzyl)-4-methyl-6-(5-phenylpyridin-2-ylmethoxy)-4,5-dihydro-1H-thiopyrano[2,3,4-c,d]indol-2-ylmethylthio]benzoic acid To a suspension of the alcohol (2.0 g) from Step 2 in 1,2-dichloroethane at r.t. under nitrogen was added thiosalicylic acid (703 mg) (Aldrich) followed by 0.7 mL $BF_3 \cdot OEt_2$. After 5 minutes, 1N HCl and THF were added to the reaction mixture which was then extracted (3× EtOAc). The organic layers were washed (2× brine), dried ($MgSO_4$), and the solvent removed in vacuo. Trituration of the residue with EtOAc, then filtration, provided the title compound as a solid; m.p. 246°-247° C.

EXAMPLE 2

2-[1-(3-Chlorobenzyl)-4-methyl-6-(5-phenylpyridin-2-ylmethoxy)-4,5-dihydro-1H-thiopyrano[2,3,4-c,d]indol-2-ylmethylthio]benzoic acid

Step 1: [1-(3-Chlorobenzyl)-4-methyl-6-(5-phenylpyridin-2-ylmethoxy)-4,5-dihydro-1H-thiopyrano[2,3,4-c,d]indol-2-yl]methanol Following the procedure described in Example 1, Steps 1–2, but substituting Ester 2 for Ester 1 in Step 1, the title compound was obtained.

Step 2: 2-[1-(3-Chlorobenzyl)-4-methyl-6-(5-phenylpyridin-2-ylmethoxy)-4,5-dihydro-1H-thiopyrano[2,3,4-c,d]indol-2-ylmethylthio]benzoic acid Following the procedure described in Example 1, Step 3, but substituting the alcohol from Step 2 for [1-(4-chlorobenzyl)-4-methyl-6-(5-phenylpyridin-2-ylmethoxy)-4,5-dihydro-1H-thiopyrano[2,3,4-c,d]indol-2-yl]methanol, the title compound was obtained as a solid; m.p. 219°-220° C.

EXAMPLE 3

2-[1-(4-Fluorobenzyl)-4-methyl-6-(5-phenylpyridin-2-ylmethoxy)-4,5-dihydro-1H-thiopyrano[2,3,4-c,d]indol-2-ylmethylthio]benzoic acid

Step 1: [1-(4-Fluorobenzyl)-4-methyl-6-(5-phenylpyridin-2-ylmethoxy)-4,5-dihydro-1H-thipyrano[2,3,4-c,d]indol-2-yl]methanol Following the procedure described in Example 1, Steps 1–2, but substituting Ester 2 for Ester 1 in Step 1, the title compound was obtained.

Step 2: 2-[1-(4-Fluorobenzyl)-4-methyl-6-(5-phenylpyridin-2-ylmethoxy)-4,5-dihydro-1H-thiopyrano[2,3,4-c,d]indol-2-ylmethylthio]benzoic acid Following the procedure described in Example 1, Step 3, but substituting the alcohol from Step 2 by the alcohol of Step 1 of the present Example, the title compound was obtained as a solid; m.p. 186°-188° C.

EXAMPLE 4

2-[1-(4-Chlorobenzyl)-4-methyl-6-(5-phenylpyridin-2-ylmethoxy)-4,5-dihydro-1H-thiopyrano[2,3,4-c,d]indol-2-ylmethylthio](N-methylsulfonyl)benzamide A suspension of 2-[1-(4-chlorobenzyl)-4-methyl-6-(5-phenylpyridin-2-ylmethoxy)-4,5-dihydro-1H-thiopyrano[2,3,4-c,d]indol-2-ylmethylthio]benzoic acid (239 mg) from Example 1, Step 3, in 10 mL THF at room temperature under nitrogen was treated with NaH (13 mg) followed by 6 μL pyridine. After 10 minutes, oxalyl chloride (47 μL) was added and the mixture became homogeneous. Stirring was continued for a further 30 minutes, then methanesulfonamide (Aldrich, 178 mg), $Et_3N$ (0.26 mL) and DMAP (9 mg) were added. The reaction was then stirred for 2 hours, poured onto 1N HCl, extracted (3× EtOAc), washed (2× brine), dried ($MgSO_4$), and evaporated. The crude product was chromatographed (silica gel; 5% MeOH in $CHCl_3$) to give the title compound as a foam.

$^1$H NMR (250 MHz, DMSO): δ1.40 (3H, d, J=7.3 Hz), 2.75 (1H, dd, J=17 Hz, 10 Hz), 3.32 (3H, s), 3.3–3.5 (2H, m), 4.15 (2H, s), 5.18 (2H, quartet, J=13 Hz), 5.41 (2H, s), 6.9–7.8 (16H, m), 8.12 (1H, dd, J=8.5 Hz, 1.7 Hz), 8.88 (1H, d, J=1.7 Hz).

EXAMPLE 5

2-[1-(4-Chlorobenzyl)-4-methyl-6-(5-phenylpyridin-2-ylmethoxy)-4,5-dihydro-1H-thiopyrano[2,3,4-c,d]indol-2-ylmethoxy]phenylacetic acid

Step 1: Methyl 2-[1-(4-chlorobenzyl)-4-methyl-6-(5-phenylpyridin-2-ylmethoxy)-4,5-dihydro-1H-thiopyrano[2,3,4-c,d]indol-2-ylmethoxy]phenylacetate To a solution of [1-(4-chlorobenzyl)-4-methyl-6-(5-phenylpyridin-2-ylmethoxy)-4,5-dihydro-1H-thiopyrano[2,3,4-c,d]indol-2-yl]methanol (250 mg) from Example 1, Step 2, methyl 2-hydroxyphenylacetate (118 mg), and Ph$_3$P (137 mg) in 7 mL THF at room temperature under nitrogen was added 83 μL DEAD. After stirring for 30 minutes, the solvent was removed and the residue chromatographed on silica gel, eluting with hexane/EtOAc 3:1 to give the title compound.

Step 2: 2-[1-(4-Chlorobenzyl)-4-methyl-6-(5-phenylpyridin-2-ylmethoxy)-4,5-dihydro-1H-thiopyrano[2,3,4-c,d]indol-2-ylmethoxy]phenylacetic acid The ester (100 mg) from Step 1 was stirred at 50° C. in a solution of 2 mL THF, 2 mL MeOH, and 0.5 mL 1N LiOH for 1.5 hours. The solution was cooled, poured onto 1N HCl, extracted (3× EtOAc), and washed (2× brine). After removal of the dried (MgSO$_4$) solvent, the product was swished with ether/EtOAc 5:1 to afford the title compound as a solid; m.p. 176°–177° C.

EXAMPLE 6

2-[1-(4-Chlorobenzyl)-4-methyl-6-(5-phenylpyridin-2-ylmethoxy)-4,5-dihydro-1H-thiopyrano[2,3,4-c,d]indol-2-ylmethoxy](N-methylsulfonyl)phenylacetamide Following the procedure described in Example 4 but substituting 2-[1-(4-chlorobenzyl)-4-methyl-6-(5-phenylpyridin-2-ylmethoxy)-4,5-dihydro-1H-thiopyrano[2,3,4-c,d]indol-2-ylmethoxy]phenylacetic acid (from Example 5, Step 2) for 2-[1-(4-chlorobenzyl)-4-methyl-6-(5-phenylpyridin-2-ylmethoxy)-4,5-dihydro-1H-thiopyrano[2,3,4-c,d]indol-2-ylmethylthio]benzoic acid, the title compound was obtained as a solid; m.p. 137.5°–139.5° C.

EXAMPLE 7

2-[2-[1-(4-Chlorobenzyl)-4-methyl-6-(5-phenylpyridin-2-ylmethoxy)-4,5-dihydro-1H-thiopyrano[2,3,4-c,d]indol-2-ylmethoxy]phenyl]propanoic acid Following the procedure described in Example 5, Steps 1–2, but substituting methyl 2-(2-hydroxyphenyl)propanoate for methyl 2-hydroxyphenylacetate in Step 1, the title compound was obtained as a solid; m.p. 111°–115° C.

EXAMPLE 8

2-[2-[1-(4-Chlorobenzyl)-4-methyl-6-(5-phenylpyridin-2-ylmethoxy)-4,5-dihydro-1H-thiopyrano[2,3,4-c,d]indol-2-ylmethoxy]phenyl](N-methylsulfonyl)propanamide Following the procedure described in Example 4 but substituting 2-[2-[1-(4-chlorobenzyl)-4-methyl-6-(5-phenylpyridin-2-ylmethoxy)-4,5-dihydro-1H-thiopyrano[2,3,4-c,d]indol-2-ylmethoxy]phenyl]propanoic acid (from Example 7) for 2-[1-(4-chlorobenzyl)-4-methyl-6-(5-phenylpyridin-2-ylmethoxy)-4,5-dihydro-1H-thiopyrano[2,3,4-c,d]indol-2-ylmethylthio]benzoic acid, the title compound was obtained as a solid; m.p. 133°–136° C.

EXAMPLE 9

2-([1-(4-Chlorobenzyl)-4-methyl-6-(5-phenylpyridin-2-ylmethoxy)-4,5-dihydro-1H-thiopyrano[2,3,4-c,d]indol-2-ylmethoxy]phenyl)butanoic acid

Step 1: Methyl 2-[1-(4-chlorobenzyl)-4-methyl-6-(5-phenylpyridin-2-ylmethoxy)-4,5-dihydro-1H-thiopyrano[2,3,4-c,d]indol-2-ylmethoxy]phenylbutanoate To a cold (0° C.) solution of diisopropylamine (0.52 mL) in 7.2 mL THF was added n-BuLi (2.3 mL; 1.6M solution in hexane) and the solution stirred for 30 minutes under nitrogen. A 1.2 mL aliquot of this solution was then added to a solution of methyl 2-[1-(4-chlorobenzyl)-4-methyl-6-(5-phenylpyridin-2-ylmethoxy)-4,5-dihydro-1H-thiopyrano[2,3,4-c,d]indol-2-ylmethoxy]phenylacetate (250 mg, from Example 5, Step 1) in 10 mL THF at −78° C. under nitrogen. After stirring for 20 minutes, ethyl iodide (148 μL) was added, the reaction warmed to r.t., and stirred for a further 2 hours. The solution was poured onto 1N HCl, extracted (3× EtOAc), washed twice with brine, dried (MgSO$_4$), and evaporated. The crude product was chromatographed on silica gel (hexane/EtOAc 3:1) to give the title compound.

Step 2: Methyl 2-[1-(4-chlorobenzyl)-4-methyl-6-(5-phenylpyridin-2-ylmethoxy)-4,5-dihydro-1H-thiopyrano[2,3,4-c,d]indol-2-ylmethoxy]phenylbutanoate Following the procedure described in Example 5, Step 2, but substituting the ester from Step 1 for methyl 2-[1-(4-chlorobenzyl)-4-methyl-6-(5-phenylpyridin-2-ylmethoxy)-4,5-dihydro-1H-thiopyrano[2,3,4-c,d]indol-2-ylmethoxy]phenylacetate, the title compound was obtained as a solid.

Anal. Calc'd for C$_{41}$H$_{37}$O$_4$N$_2$SCl: C, 71.45; H, 5.41; N, 4.06. Found: C, 71.74; H, 5.45; N, 4.02.

EXAMPLE 10

2-[1-(4-Chlorobenzyl)-4-methyl-6-(5-phenylpyridin-2-ylmethoxy)-4,5-dihydro-1H-thiopyrano[2,3,4-c,d]indol-2-ylmethylthio]phenylacetic acid

Step 1: Methyl 2-methylthiobenzoate

To a solution of thiosalicylic acid (5 g) in 50 mL DMF was added K$_2$CO$_3$ (8.9 g) followed by MeI (9.96 mL) and the solution was stirred at 80° C. under nitrogen for 16 hours. The reaction mixture was poured onto NH$_4$OAc solution (pH=7), extracted (2× EtOAc), washed with brine, dried, and evaporated to yield the title compound.

Step 2: 2-Methylthiobenzoic acid

Following the procedure described in Example 5, Step 2, but substituting the ester from Step 1 for methyl 2-[1-(4-chlorobenzyl)-4-methyl-6-(5-phenylpyridin-2-ylmethoxy)-4,5-dihydro-1H-thiopyrano[2,3,4-c,d]indol-2-ylmethoxy]phenylacetate as starting material, the title compound was obtained as a solid.

Step 3: Methyl 2-methylthiophenylacetate

The acid from Step 2 (1.0 g) was dissolved in CH$_2$Cl$_2$ (10 mL) containing two drops of DMF at 0° C. under nitrogen and oxalyl chloride (620 μL) was then added dropwise. After 15 minutes, the temperature was raised to 25° C. for 30 minutes and then this solution was added slowly over 30 minutes to a solution of diazomethane (large excess) in Et$_2$O. After 1 hour, the solvent was evaporated and the residue purified by chromatography (hexane/EtOAc 1:1) to provide a yellow solid (1.07 g). This yellow solid (the diazoketone) was dissolved in MeOH (170 mL) and Et$_3$N (10.7 mL) and treated with silver benzoate (1.64 g) at r.t. for 1 hour. The mixture was filtered through celite, diluted with EtOAc, washed with 1N HCl then brine, dried (MgSO$_4$), and evaporated. The resulting yellow solid was chromatographed on silica gel (hexane/EtOAc 7:3) to provide a red oil, the title compound, which was used as such in the next step.

Step 4: Methyl 2-thiophenylacetate

The methyl 2-methylthiophenylacetate (215 mg) from Step 3 was dissolved in 5 mL CHCl$_3$ at 0° C. and m-CPBA (235 mg) added. After 1 hour, Ca(OH)$_2$ (121 mg) was added, the mixture stirred for 15 minutes at r.t. then filtered and evaporated. The residue was dissolved in TFAA (2 mL) and refluxed for 30 minutes. After evaporation, the residue was dissolved in MeOH/Et$_3$N (1:1, 44 mL) and evaporated to dryness. The product was dissolved in CH$_2$Cl$_2$, washed with NH$_4$Cl (saturated solution), dried (MgSO$_4$), and evaporated. Purification on silica gel eluting with hexane/EtOAc 9:1 gave the title compound as a red oil which was used as such in the next step.

Step 5: Methyl 2-[1-(4-chlorobenzyl)-4-methyl-6-(5-phenylpyridin-2-ylmethoxy)-4,5-dihydro-1H-thiopyrano[2,3,4-c,d]indol-2-ylmethylthio]phenylacetate Following the procedure described in Example 1, Step 3, but substituting the thiol from Step 4 for thiosalicylic acid, the title compound was obtained.

Step 6: 2-[1-(4-Chlorobenzyl)-4-methyl-6-(5-phenylpyridin-2-ylmethoxy)-4,5-dihydro-1H-thiopyrano[2,3,4-c,d]indol-2-ylmethylthio]phenylacetic acid Following the procedure described in Example 5, Step 2, but substituting the ester from Step 5 for 2-[1-(4-chlorobenzyl)-4-methyl-6-(5-phenylpyridin-2-ylmethoxy)-4,5-dihydro-1H-thiopyrano[2,3,4-c,d]indol-2-ylmethoxy]phenylacetic acid as starting material, the title compound was obtained as a solid; m.p. 100°-102° C.

EXAMPLE 11

2-[1-(3-Chlorobenzyl)-4-methyl-6-(5-phenylpyridin-2-ylmethoxy)-4,5-dihydro-1H-thiopyrano[2,3,4-c,d]indol-2-ylmethoxy]phenylacetic acid Following the procedure described in Example 5, Steps 1-2, but substituting [1-(3-chlorobenzyl)-4-methyl-6-(5-phenylpyridin-2-ylmethoxy)-4,5-dihydro-1H-thiopyrano[2,3,4-c,d]indol-2-yl]methanol (from Example 2, Step 1) for [1-(4-chlorobenzyl)-4-methyl-6-(5-phenylpyridin-2-ylmethoxy)-4,5-dihydro-1H-thiopyrano[2,3,4-c,d]indol-2-yl]methanol as starting material in Step 1, the title compound was obtained as a solid: m.p. 153°-154° C.

EXAMPLE 12

2-[2-[1-(3-Chlorobenzyl)-4-methyl-6-(5-phenylpyridin-2-ylmethoxy)-4,5-dihydro-1H-thiopyrano[2,3,4-c,d]indol-2-ylmethoxy]phenyl]propanoic acid Following the procedure described in Example 5, Steps 1-2, but substituting [1-(3-chlorobenzyl)-4-methyl-6-(5-phenylpyridin-2-ylmethoxy)-4,5-dihydro-1H-thiopyrano[2,3,4-c,d]indol-2-yl]methanol (from Example 2, Step 1) for [1-(4-chlorobenzyl)-4-methyl-6-(5-phenylpyridin-2-ylmethoxy)-4,5-dihydro-1H-thiopyrano[2,3,4-c,d]indol-2-yl]methanol and methyl 2-(2-hydroxyphenyl)propanoate for methyl 2-hydroxyphenylacetate as starting material in Step 1, the title compound was obtained as a solid; m.p. 160°-162° C.

EXAMPLE 13

2-[1-(4-Fluorobenzyl)-4-methyl-6-(5-phenylpyridin-2-ylmethoxy)-4,5-dihydro-1H-thiopyrano[2,3,4-c,d]indol-2-ylmethoxy]phenylacetic acid Following the procedure described in Example 5, Steps 1-2, but substituting [1-(4-fluorobenzyl)-4-methyl-6-(5-phenylpyridin-2-ylmethoxy)-4,5-dihydro-1H-thiopyrano[2,3,4-c,d]indol-2-yl]methanol (from Example 3, Step 1) for [1-(4-chlorobenzyl)-4-methyl-6-(5-phenylpyridin-2-ylmethoxy)-4,5-dihydro-1H-thiopyrano[2,3,4-c,d]indol-2-yl]methanol as starting material in Step 1, the title compound was obtained as a solid; m.p. 129°-132° C.

EXAMPLE 14

2-[2-[1-(4-Fluorobenzyl)-4-methyl-6-(5-phenylpyridin-2-ylmethoxy)-4,5-dihydro-1H-thiopyrano[2,3,4-c,d]indol-2-ylmethoxy]phenyl]propanoic acid Following the procedure described in Example 5, Steps 1-2, but substituting [1-(4-fluorobenzyl)-4-methyl-6-(5-phenylpyridin-2-ylmethoxy)-4,5-dihydro-1H-thiopyrano[2,3,4-c,d]indol-2-yl]methanol (from Example 3, Step 1) for [1-(4-chlorobenzyl)-4-methyl-6-(5-phenylpyridin-2-ylmethoxy)-4,5-dihydro-1H-thiopyrano[2,3,4-c,d]indol-2-yl]methanol and methyl 2-(2-hydroxyphenyl)propanoate for methyl 2-hydroxyphenylacetate as starting material in Step 1, the title compound was obtained as a solid; m.p. 163°-166° C.

EXAMPLE 15

2-[1-(3-Chloro-4-fluorobenzyl)-4-methyl-6-(5-phenylpyridin-2-ylmethoxy)-4,5-dihydro-1H-thiopyrano[2,3,4-c,d]indol-2-ylmethoxy]phenylacetic acid

Step 1: Ethyl [4-methyl-4,5-dihydro-1H-thiopyrano-[2,3,4-c,d]indol-2-yl]carboxylate To a solution of Ester 1 (5.63 g) in CH$_2$Cl$_2$ (130 mL) at 0° C. under nitrogen was added BBr$_3$ (1.0M in CH$_2$Cl$_2$; 21.0 mL). After stirring for 1.5 hours at 0° C. the reaction was poured into NaHCO$_3$ (saturated) and crushed ice. Extraction with CH$_2$Cl$_2$ was followed by drying with MgSO$_4$. Purification by flash chromatography on silica (40% EtOAc/hexane as eluant) then crystallization from Et$_2$O/hexane gave the title compound.

Step 2: Ethyl [4-methyl-6-(5-phenylpyridin-2-yl-methoxy)-4,5-dihydro-1H-thiopyrano-[2,3,4-c,d]indol-2-yl]carboxylate Following the procedure described in Example 1, Step 1, but substituting the phenol (2.5 g) from Step 1 for ethyl [1-(4-chlorobenzyl)-4-methyl-4,5-dihydro-1H-thiopyrano[2,3,4-c,d]indol-2-yl]carboxylate as starting material, the title compound was obtained as a solid.

Step 3: 3-Chloro-4-fluorobenzyl alcohol

To a solution of LiAlH₄ (2.2 g) in THF (100 mL) at 0° C. under nitrogen was added 3-chloro-4-fluorobenzoic acid (Aldrich; 10 g). After stirring for 1 hour at 0° C. the mixture was stirred for 1 hour at 25° C. followed by the addition of a further 1.0 g of LiAlH₄. Stirring was continued for a further 12 hours at 25° C. after which time the mixture was cooled to 0° C. and quenched with H₂O. The mixture was then acidified with 1N HCl (aq) and extracted with EtOAc. After washing with NaHCO₃ (aq) and drying (MgSO₄), the organic solution was evaporated to give the title compound as an oil.

Step 4: 3-Chloro-4-fluorobenzyl p-toluenesulfonate

Sodium hydride (0.33 g) was added to a solution of the alcohol from Step 3 (2.0 g) in THF (50 mL) at 0° C. under N₂. Stirring was continued for 5 minutes at 0° C. followed by 25 min at 25° C. The mixture was then cooled to 0° C. and p-toluenesulfonyl chloride (2.5 g) was added. Stirring was continued for 40 minutes at 0° C. followed by 2 hours at 25° C. The precipitated NaCl was allowed to settle and the supernatant solution (4.0 mL) of the title compound was used directly in the next step.

Step 5: Ethyl [1-(3-chloro-4-fluorobenzyl)-4-methyl-6-(5-phenylpyridin-2-ylmethoxy)-4,5-dihydro-1H-thiopyrano[2,3,4-c,d]indol-2-yl]carboxylate To a solution of the indole from Step 2 (400 mg) in DMF (10 mL) at −60° C. under nitrogen was added KHMDS (0.5M in toluene; 2.2 mL). After stirring 20 minutes at −78° C., 3-chloro-4-fluorobenzyl-p-toluenesulfonate (1.0 mmol from Step 4) in THF (4 mL) was added. The reaction was then stirred at 25° C. for 18 hr followed by quenching with 1N HCl and extraction with EtOAc. After drying (MgSO₄) and evaporation of the solvent, flash chromatography on silica (30% EtOAc/hexane as eluent) gave the title compound as a solid.

Step 6: 2-[1-(3-Chloro-4-fluorobenzyl)-4-methyl-6-(5-phenyl-pyridin-2-ylmethoxy)-4,5-dihydro-1H-thiopyrano[2,3,4-c,d]indol-2-ylmethoxy]phenylacetic acid Following the procedure described in Example 1, Step 2, then Example 5, Steps 1 and 2, but substituting the ester from Step 5 for ethyl [1-(4-chlorobenzyl)-4-methyl-6-(5-phenylpyridin-2-yl-methoxy)-4,5-dihydro-1H-thiopyrano[2,3,4-c,d]indol-2-yl]carboxylate as starting material, the title compound was obtained as a solid; m.p. 154°–157° C.

EXAMPLE 16

2-[1-Phenyl-4-methyl-6-(5-pyridin-2-ylmethoxy)-4,5-dihydro-1H-thiopyrano[2,3,4-c,d]indol-2-ylmethoxy]-phenylacetic acid

Step 1: Ethyl [1-phenyl-4-methyl-6-(5-pyridin-2-ylmethoxy)-4,5-dihydro-1H-thiopyrano[2,3,4-c,d]indol-2-yl]carboxylate A solution of ethyl [4-methyl-6-(5-phenylpyridin-2-ylmethoxy)-4,5-dihydro-1H-thiopyrano[2,3,4-c,d]indol-2-yl]carboxylate from Example 15, Step 2 (300 mg), K₂CO₃ (500 mg), Cu₂Br₂ (130 mg) and pyridine (2 mL) in iodobenzene (10 mL) was heated to 250° C. for 1 hr. The reaction was cooled to 25° C., diluted with EtOAc and decanted. The organic layer was washed with dilute HCl (aq) and brine, then dried (MgSO₄), and the solvent evaporated. Purification by flash chromatography (silica gel, 40% then 50% EtOAc/hexane) followed by a swish with hexane afforded the title compound.

Step 2: 2-[1-Phenyl-4-methyl-6-(5-pyridin-2-ylmethoxy)-4,5-dihydro-1H-thiopyrano[2,3,4-c,d]indol-2-ylmethoxy]-phenylacetic acid Following the procedure described in Example 1, Step 2, then Example 5, Steps 1 and 2, but substituting the ester from Step 1 for ethyl [1-(4-chlorobenzyl)-4-methyl-6-(5-phenylpyridin-2-ylmethoxy)-4,5-dihydro-1H-thiopyrano[2,3,4-c,d]indol-2-yl]carboxylate as starting material, the title compound was obtained as a solid; m.p. 135°–140° C.

EXAMPLE 17

2-[1-(3-(2H-5,6-Dihydropyran-4-yl)benzyl)-6-(5-phenylpyridin-2-ylmethoxy)-4,5-dihydro-1H-thiopyrano[2,3,4-c,d]-indol-2-ylmethoxy]phenylacetic acid

Step 1: 1-[3-(4-Methoxytetrahydropyran-4-yl)benzyl]-1-(allyloxyphenyl)hydrazine To a suspension of 4-allyloxyphenylhydrazine hydrochloride (2.0 g) in 60 mL CH₂Cl₂ was added diisopropylethylamine (4.6 mL), tetrabutylammonium bromide (1.0 g), and 3-(4-methoxytetrahydropyran-4-yl)benzyl chloride (2.5 g) and the mixture was then stirred at r.t. under nitrogen for 24 hours. The mixture was concentration in vacuo, Et₂O added, and the solution washed twice with brine, dried (MgSO₄), and evaporated. Purification of the residue by chromatography (silica gel: hexane/EtOAc 1:1 then 1:3) afforded the title compound.

Step 2: Ethyl [1-[3-(4-methoxytetrahydropyran-4-yl)benzyl]-3-t-butylthio-5-allyloxyindol-2-yl]carboxylate A solution of the hydrazine from Step 1 (1.45 g), Ketone 1 (2.5 g), and NaOAc (750 mg) in 16 mL toluene and 8 mL HOAc was heated to 75° C. under nitrogen for 2 hours. The mixture was cooled, poured onto brine, extracted with EtOAc, and the organic layer washed with 3N HCl, then with water. After removal of the dried (MgSO₄) solvent, the crude product was subjected to silica gel chromatography (hexane/EtOAc 2:1) to provide the title compound as an oil.

Step 3: Ethyl [1-[3-(4-methoxytetrahydropyran-4-yl)benzyl)]-3-t-butylthio-4-allyl-5-hydroxyindol-2-yl]carboxylate The indole from Step 2 (1.3 g) and D₂CO₃ (100 mg) were added to 5 mL 1,2-dichlorobenzene and heated to 175° C. under nitrogen for 10 hours. The solution was cooled and chromatographed (silica gel; hexane/EtOAc 2:1 then 1:1) to provide the title compound.

Step 4: Ethyl [1-[3-(2-H-5,6-dihydropyran-4-yl)benzyl]6-hydroxy-4,5-dihydro-1H-thiopyrano[2,3,4-c,d]indol-2-yl]carboxylate The indole from Step 3 (1.0 g) and p-TSA (320 mg) were dissolved in 25 mL CH₂Cl₂ and stirred at room temperature for 16 hours. After removal of the solvent, the residue was chromatographed (silica gel; hexane/EtOAc 2:1) to afford the title compound as a solid; m.p. 184°–187° C.

Step 5: [1-[3-(2H-5,6-dihydropyran-4-yl)benzyl]-6-(5-phenyl-pyridin-2-ylmethoxy)-4,5-dihydro-1H-thiopyrano[2,3,4-c,d]indol-2-yl]methanol Following the procedure described in Example 1, Steps 1–2, but substituting Ester 1 with the ester from Step 4, the title compound was obtained as a solid.

Step 6: 2-[1-(3-(2H-5,6-dihydropyran-4-yl)benzyl)-6-(5-phenyl-pyridin-2-ylmethoxy)-4,5-dihydro-1H-thiopyrano[2,3,4-c,d]indol-2-ylmethoxy]phenylacetic acid Following the procedure described in Example 5, Steps 1–2, but substituting the alcohol from Step 5 for [1-(4-chlorobenzyl)-6-(5-phenylpyridin-2-ylmethoxy)-4,5-dihydro-1H-thiopyrano[2,3,4-c,d]indol-2-yl]methanol as starting material, the title compound was obtained as a solid; m.p. 146°–149° C.

EXAMPLE 18

2-[[1-(4-Chlorobenzyl)-4-methyl-6-(5-phenylpyridin-2-ylmethoxy)-4,5-dihydro-1H-thiopyrano[2,3,4-c,d]indol-2-yl]methoxymethyl]benzoic acid

Step 1: 2-[[1-(4-chlorobenzyl)-4-methyl-6-(5-phenylpyridin-2-ylmethoxy)-4,5-dihydro-1H-thiopyrano[2,3,4-c,d]indol-2-yl]methoxymethyl]benzonitrile A suspension of [1-(4-chlorobenzyl)-4-methyl-6-(5-phenylpyridin-2-ylmethoxy)-4,5-dihydro-1H-thiopyrano[2,3,4-c,d]indol-2-yl]methanol (425 mg) from Example 1, Step 2, in 15 mL DMF was treated sequentially with NaH (24 mg) and 2-cyanobenzyl bromide (Aldrich; 198 mg) at r.t. nitrogen for 2 hours. the mixture was poured onto 1N HCl, extracted (3× EtOAc), washed (2× brine), dried (MgSO₄), and evaporated. The product was triturated with Et₂O to provide the title compound as a solid.

Step 2: 2-[[1-(4-Chlorobenzyl)-4-methyl-6-(5-phenylpyridin-2-ylmethoxy)-4,5-dihydro-1H-thiopyrano[2,3,4-c,d]indol-2-yl]methoxymethyl]benzoic acid The nitrile (230 mg) from Step 1, 8N KOH (1 mL), ethylene glycol (7.5 mL), and 2-(ethoxyethoxy)ethanol (2.5 mL) were heated to 150° C. under nitrogen for 8 hours. The mixture was then cooled, EtOAc added, followed by 1N HCl. Filtration afforded a solid which was purified by chromatography (silica gel; hexane/EtOAc 1:2 then EtOAc/HOAc 10:1) to give the title compound as a solid; m.p. 164°–167° C.

EXAMPLE 19

5-[[1-(4-Chlorobenzyl)-4-methyl-6-(5-phenylpyridin-2-ylmethoxy)-4,5-dihydro-1H-thiopyrano[2,3,4-c,d]indol-2-yl]methoxymethylphen-2-yl]-1H-tetrazole A solution of 2-[[1-(4-chlorobenzyl)-4-methyl-6-(5-phenylpyridin-2-ylmethoxy)-4,5-dihydro-1H-thiopyrano[2,3,4-c,d]indol-2-yl]methoxymethyl]benzonitrile (200 mg) from Example 18, Step 1 and n-Bu₃SnN₃ (0.6 mL) in 1,2-dichlorobenzene (2 mL) was heated to 135° C. under nitrogen. After 6 hours, 1 mL HOAc was added, the solution was cooled and then chromatographed (silica gel; hexane/EtOAc 4:1 then hexane/EtOAc/HOAc 10:10:1) to provide the title compound as a solid; m.p. 161°–162° C.

EXAMPLE 20

5-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxymethylphen-2-yl]-1H-tetrazole

Step 1: 2-[1-(4-Chlorobenzyl)-4-methyl-6-hydroxy-4,5-dihydro-1H-thiopyrano[2,3,4-c,d]indol-2-yl]ethanol To a solution of Ester 4 (19.6 g) in THF (800 mL) at 0° C. under nitrogen was added LiALH₄ (4.4 g) in portions over 30 minutes. During this time a precipitate formed. After 1 hour, the mixture was poured onto 1N HCl, extracted (3× EtOAc), washed (2× brine), dried (MgSO₄), and evaporated. The residue was swished with Et₂O/hexane and filtered to provide the title compound as a solid.

Step 2: 2-[1-(4-Chlorobenzyl)-4-methyl-6-(5-phenylpyridin-2-ylmethoxy)-4,5-dihydro-1H-thiopyrano[2,3,4-c,d]indol-2-yl]ethanol Following the procedure described in Example 1, Step 1, but substituting the alcohol from Step 1 for the Ester 1, the title compound was obtained as a solid.

Step 3: 5-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxymethylphen-2-yl]-1H-tetrazole Using the procedures described in Example 18, Step 1 followed by Example 19 but substituting the alcohol from Step 2 for [1-(4-chlorobenzyl)-4-methyl-6-(5-phenylpyridin-2-ylmethoxy)-4,5-dihydro-1H-thiopyrano[2,3,4-c,d]indol-2-yl]methanol as starting material, the title compound was obtained as a solid; m.p. 160° C. (dec).

EXAMPLE 21

2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethylthio]benzoic acid

Step 1: 2-[1-(4-Chlorobenzyl)-4-methyl-6-(5-phenylpyridin-2-ylmethoxy)-4,5-dihydro-1H-thiopyrano[2,3,4-c,d]indol-2-yl]ethyl bromide To a solution of 2-[1-(4-chlorobenzyl)-4-methyl-6-(5-phenylpyridin-2-ylmethoxy)-4,5-dihydro-1H-thiopyrano[2,3,4-c,d]indol-2-yl]ethanol (400 mg), from Example 20, Step 2, in CH$_2$Cl$_2$ (12 ml) was added Ph$_3$P (408 mg) and CBr$_4$ (491 mg). The mixture was stirred for 20 minutes at r.t., then chromatographed on a silica gel column using 5% Et$_2$O in CH$_2$Cl$_2$ as eluent, to give 341 mg of the title compound.

Step 2:

2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethylthio]benzoic acid To a solution of thiosalicylic acid (38 mg) in DMF (2 mL) at 0° C. was added NaH (12 mg). After 10 minutes the alcohol (100 mg) from Step 1 was added and the mixture was stirred for 2 hours at r.t. The mixture was acidified with 1N HCl, extracted with EtOAc, the organic layer was washed with brine (2×), dried over MgSO$_4$, filtered, and evaporated to dryness. The residue was purified by silica gel chromatography (hexane/EtOAc 1:1, then 5% HOAc added to this solvent mixture) giving the title compound; m.p. 210°–213° C.

EXAMPLE 22

2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]benzoic acid Following the procedure described in Example 5, Steps 1–2, but substituting methyl 2-hydroxybenzoate (Lancaster) for methyl 2-hydroxyphenylacetate and 2-[1-(4-chlorobenzyl)-4-methyl-6-(5-phenylpyridin-2-ylmethoxy)-4,5-dihydro-1H-thiopyrano[2,3,4-c,d]indol-2-yl]ethanol from Example 20, Step 2, for [1-(4-chlorobenzyl)4-methyl-6-(5-phenylpyridin-2-ylmethoxy)-4,5-dihydro-1H-thiopyrano[2,3,4-c,d]indol-2-yl]methanol as starting material, the title compound was obtained as a solid; m.p. 218.5°–219° C.

EXAMPLE 23

2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy](N-methylsulfonyl)benzamide Following the procedure described for Example 4 but substituting 2-[2-[1-(4-chlorobenzyl)-4-methyl-6-(5-phenylpyridin-2-ylmethoxy)-4,5-dihydro-1H-thiopyrano[2,3,4-c,d)indol-2-yl]ethoxy]benzoic acid from Example 22 for 2-[1-(4-chlorobenzyl)-4-methyl-6-(5-phenylpyridin-2-ylmethoxy)-4,5-dihydro-1H-thiopyrano[2,3,4-c,d]indol-2-ylmethylthio]benzoic acid as starting material, the title compound was obtained as a solid; m.p. 196°–199° C.

EXAMPLE 24

5-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]phen-2-yl]-1H-tetrazole Step 1:

2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]benzonitrile Following the procedure described in Example 5, Step 1, but substituting 2-hydroxybenzonitrile (Aldrich) for methyl 2-hydroxyphenyl acetate and 2-[1-(4-chlorobenzyl)-4-methyl-6-(5-phenylpyridin-2-ylmethoxy)-4,5-dihydro-1H-thiopyrano[2,3,4-c,d]indol-2-yl]ethanol from Example 20, Step 2, for [1-(4-chlorobenzyl)-4-methyl-6-(5-phenylpyridin-2-ylmethoxy)-4,5-dihydro-1H-thiopyrano[2,3,4-c,d]indol-2-yl]methanol as starting material, the title compound was obtained.

Step 2:

5-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]phen-2-yl]-1H-tetrazole A solution of the nitrile (265 mg) from Step 1 and n-Bu$_3$SnN$_3$ (680 mg) in 1,2-dichlorobenzene (4 mL) was heated at 125° C. for 8 hrs. After cooling to r.t., 2 mL of HOAc was added. The mixture was stirred for 20 minutes, then chromatographed on silica gel using 1:1 EtOAc: hexane as a solvent to start, followed by addition of 5% HOAc to this solvent. The title compound was obtained as a solid; m.p. 256° C.

EXAMPLE 25

2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy](N-acetyl)phenylsulfonamide Step 1: 2-hydroxyphenylsulfonamide To a solution of chlorosulfonylisocyanate (Aldrich; 2 mL) in 76 mL MeNO$_2$ at 0° C. was added phenol (2 g) in 10 mL MeNO$_2$. The solution was heated at 45° C. for 30 minutes then AlCl$_3$ (3.46 g) was added and the temperature raised to 100° C. for 30 minutes. The reaction mixture was poured onto ice/H$_2$O, extracted (2× Et$_2$O), and washed with H$_2$O. The organic layer extracted with K$_2$CO$_3$ (saturated solution) and the aqueous phase then acidified with 1N HCl. Extraction of the aqueous phase with Et$_2$O followed by drying (MgSO$_4$) and evaporation yielded a black oil. Purification of this oil by chromatography (hexane/EtOAc 1:1) gave the title compound as a white solid.

Step 2:

2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]phenylsulfonamide The 2-hydroxyphenylsulfonamide (220 mg) from Step 1 was dissolved in 10 mL THF then Ph$_3$P (333 mg) and 2-[1-(4-chlorobenzyl)-4-methyl-6-(5-phenylpyridin-2-ylmethoxy)-4,5-dihydro-1H-thiopyrano[2,3,4-c,d]indol-2-yl]ethanol (625 mg) from Example 20, Step 2, were added. To this solution was added DEAD (200 μL) and the resulting mixture was stirred at r.t. under nitrogen for 16 hours. After removal of the solvent, the residue was triturated with MeOH/CH$_2$Cl$_2$ to give the title compound as a white solid; m.p. 173°–175° C.

Step 3:

2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy](N-acetyl)phenylsulfonamide The sulfonamide (80 mg) from Step 2 was dissolved in 2 mL THF at r.t. under nitrogen and NaH (4.2 mg) was then added. After stirring for 2 hours, pyridine (excess) and acetyl chloride (24 μL) were added and stirring was continued a further 3 hours at 60° C. The solution was poured onto 1N HCl, extracted twice with EtOAc, washed with brine, dried (MgSO$_4$), and evaporated to give a brown oil. Purification of the oil by chromatography (silica gel; hexane/EtOAc 1:1) provided a yellow solid which was triturated with Et$_2$O to give the title compound as a yellow solid; m.p. 110°–112° C.

EXAMPLE 26

2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy](N-benzoyl)phenylsulfonamide Following the procedure described in Example 25, Steps 1-3, but substituting benzoyl chloride for acetyl chloride in Step 3, the title compound was obtained as a white solid; m.p. 162°-163° C.

EXAMPLE 27

2-[2-[1-(3-Chlorobenzyl)-4-methyl-6-(5-phenylpyridin-2-ylmethoxy)-4,5-dihydro-1H-thiopyrano[2,3,4-c,d]indol-2-yl]ethoxy]benzoic acid Step 1:
2-[1-(3-Chlorobenzyl)-4-methyl-6-hydroxy-4,5-dihydro-1H-thiopyrano[2,3,4-c,d]indol-2-yl]ethanol Following the procedure described in Example 20, Step 1, but substituting Ester 5 for Ester 4 as starting material, the title compound was obtained as a solid.

Step 2:
2-[1-(3-(Chlorobenzyl)-4-methyl-6-(5-phenylpyridin-2-ylmethoxy)-4,5-dihydro-1H-thiopyrano[2,3,4-c,d]indol-2-yl]ethanol Following the procedure described in Example 1, Step 1, but substituting the alcohol from Step 1 for the Ester 1 as starting material, the title compound was obtained.

Step 3:
2-[2-[1-(3-Chlorobenzyl)-4-methyl-6-(5-phenylpyridin-2-ylmethoxy)-4,5-dihydro-1H-thiopyrano[2,3,4-c,d]indol-2-yl]ethoxy]benzoic acid Following the procedure described in Example 5, Steps 1-2, but substituting methyl 2-hydroxybenzoate for methyl 2-hydroxyphenylacetate and the alcohol from Step 2 for [1-(4-chlorobenzyl)-4-methyl-6-(5-phenylpyridin-2-ylmethoxy)-4,5-dihydro-1H-thiopyrano[2,3,4-c,d]indol-2-yl]methanol as starting material, the title compound was obtained as a solid; m.p. 174°-176° C.

EXAMPLE 28

2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethylthio]phenylacetic acid Step 1: Methyl 2-[2-[1-(4-chlorobenzyl)-4-methyl-6-(5-phenylpyridin-2-ylmethoxy)-4,5-dihydro-1H-thiopyrano[2,3,4-c,d]indol-2-yl]ethyl]phenylacetate To a solution of methyl 2-thiophenylacetate (from Example 10, Step 4; 68.6 mg) in 3 mL DMF was added NaH (12.7 mg) followed by 2-[1-(4-chlorobenzyl)-4-methyl-6-(5-phenylpyridin-2-ylmethoxy)-4,5-dihydro-1H-thiopyrano[2,3,4-c,d]indol-2-yl]ethyl bromide (from Example 21, Step 1; 207 mg). The mixture was stirred at r.t. under nitrogen for 16 hours and then poured into H2O. After extraction with EtOAc, the organic layer was washed with brine, dried (MgSO4), and evaporated. The resulting oil was chromatographed on silica gel (hexane/EtOAc 9:1) to afford the title compound as a yellow oil.

Step 2:
2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethylthio]phenylacetic acid Following the procedure of Example 5, Step 2, but substituting the ester from Step 1 for methyl 2-[1-(4-chlorobenzyl)-4-methyl-6-(5-phenylpyridin-2-ylmethoxy)-4,5-dihydro-1H-thiopyrano[2,3,4-c,d]indol-2-ylmethoxy]phenylacetate as starting material, the title compound was obtained as a solid; m.p. 98°-100° C.

EXAMPLE 29

2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]phenylacetic acid Following the procedure described in Example 5, Steps 1-2, but substituting 2-[1-(4-chlorobenzyl)-4-methyl-6-(5-phenylpyridin-2-ylmethoxy)-4,5-dihydro-1H-thiopyrano[2,3,4-c,d]indol-2-yl]ethanol from Example 20, Step 2, for [1-(4-chlorobenzyl)-4-methyl-6-(5-phenylpyridin-2-ylmethoxy)-4,5-dihydro-1H-thiopyrano[2,3,4-c,d]indol-2-yl]methanol as starting material, the title compound was obtained as a solid; m.p. 201°-202.5° C.

EXAMPLE 30

2-[2-[2-(1-(4-Chlorobenzyl)-4-methyl-6-(5-phenylpyridin-2-ylmethoxy)-4,5-dihydro-1H-thiopyrano[2,3,4-c,d]indol-2-yl)ethoxy]phenyl]propanoic acid Following the procedure described in Example 5, Steps 1-2, but substituting methyl 2-(2-hydroxyphenyl)propanoate for methyl 2-hydroxyphenylacetate and 2-[1-(4-chlorobenzyl)-4-methyl-6-(5-phenylpyridin-2-ylmethoxy)-4,5-dihydro-1H-thiopyrano[2,3,4-c,d]indol-2-yl]ethanol from Example 20, Step 2, for [1-(4-chlorobenzyl)-4-methyl-6-(5-phenylpyridin-2-ylmethoxy)-4,5-dihydro-1H-thiopyrano[2,3,4-c,d]indol-2-yl]methanol as starting material, the title compound was obtained as a solid; m.p. 150°-156° C.

EXAMPLE 31

2-[2-[2-(1-(4-Chlorobenzyl)-4-methyl-6-(5-phenylpyridin-2-ylmethoxy)-4,5-dihydro-1H-thiopyrano[2,3,4-c,d]indol-2-yl)ethoxy]phenyl]butanoic acid Following the procedure described in Example 5, Steps 1-2, but substituting methyl 2-(2-hydroxyphenyl)butanoate butanoate for methyl 2-hydroxyphenylacetate and 2-[1-(4-chlorobenzyl)-4-methyl-6-(5-phenylpyridin-2-ylmethoxy)-4,5-dihydro-1H-thiopyrano[2,3,4-c,d]indol-2-yl]ethanol from Example 20, Step 2, for [1-(4-chlorobenzyl)-4-methyl-6-(5-phenylpyridin-2-ylmethoxy)-4,5-dihydro-1H-thiopyrano[2,3,4-c,d]indol-2-yl]methanol as starting material, the title compound was obtained as a solid; m.p. 102°-104° C.

EXAMPLE 32

2-[2-[1-(3-Chlorobenzyl)-4-methyl-6-(5-phenylpyridin-2-ylmethoxy)-4,5-dihydro-1H-thiopyrano[2,3,4-c,d]indol-2-yl]ethoxy]phenylacetic acid Following the procedure described in Example 5, Steps 1-2, but substituting 2-[1-(3-chlorobenzyl)-4-methyl-6-(5-phenylpyridin-2-ylmethoxy)-4,5-dihydro-1H-thiopyrano[2,3,4-c,d]indol-2-yl]ethanol from Example 27, Step 2 for [1-(4-chlorbenzyl)-4-methyl-6-(5- phenylpyridin-2-ylmethoxy)-4,5-dihydro-1H-thiopyrano[2,3,4-c,d]indol-2-yl]methanol as starting material, the title compound was obtained as a solid; m.p. 118°-125° C.

EXAMPLE 33

(−)
2-[2-[1-(3-Chlorobenzyl)-4-methyl-6-(5-phenylpyridin-2-ylmethoxy)-4,5-dihydro-1H-thiopyrano[2,3,4-c,d]indol-2-yl]ethoxy]phenylacetic acid Step 1: (+)
2-[1-(3-Chlorobenzyl)-4-methyl-6-(5-phenylpyridin-2-ylmethoxy)-4,5-dihydro-1H-thiopyrano[2,3,4-c,d]indol-2-yl]ethanol The title compound was obtained by following the procedure described in Example 27, Steps 1-2 but substituting the racemic material in Step 2 by (+) 2-[1-(3-chlorobenzyl)-4-methyl-6-hydroxy-4,5-dihydro-1H-thiopyrano[2,3,4-c,d]indol-2-yl]ethanol. Resolution of the racemate from Example 27, Step 1, was achieved by preparative HPLC using a Chiralpak AS column (50×2 cm I.D.) eluting with hexane/i-PrOH 1:1 at 5 mL/minute. The enantiomer with the shorter retention time was collected to provide (after removal of the solvent) (+) 2-[1-(3-chlorobenzyl)-4-methyl-6-hydroxy-4,5-dihydro-1H-thiopyrano[2,3,4-c,d]indol-2-yl]ethanol.

Step 2: (−)
2-[2-[1-(3-Chlorobenzyl)-4-methyl-6-(5-phenylpyridin-2-ylmethoxy)-4,5-dihydro-1H-thiopyrano[2,3,4-c,d]indol-2-yl]ethoxy]phenylacetic acid Following the procedure described in Example 5, Steps 1-2, but substituting the (+) alcohol from Step 1 for [1-(4-chlorobenzyl)-4-methyl-6-(5-phenylpyridin-2-ylmethoxy)-4,5-dihydro-1H-thiopyrano-[2,3,4-c,d]indol-2-yl]methanol as starting material, the title compound was obtained as a solid; m.p. 146.5°-148° C.
$[\alpha]_D$ −25.5° (c=0.77, CHCl$_3$).

EXAMPLE 34

(+)
2-[2-[1-(3-Chlorobenzyl)-4-methyl-6-(5-phenylpyridin-2-ylmethoxy)-4,5-dihydro-1H-thiopyrano[2,3,4-c,d]indol-2-yl]ethoxy]phenylacetic acid Step 1: (−)
2-[1-(3-Chlorobenzyl)-4-methyl-6-(5-phenylpyridin-2-ylmethoxy)-4,5-dihydro-1H-thiopyrano[2,3,4-c,d]indol-2-yl]ethanol The title compound was obtained by following the procedure described in Example 27, Steps 1-2, but substituting the racemic material in Step 2 by (−) 2-[1-(3-chlorobenzyl)-4-methyl-6-hydroxy-4,5-dihydro-1H-thiopyrano[2,3,4-c,d]indol-2-yl]ethanol. Resolution of the racemate from Example 27, Step 1, was achieved by preparative HPLC using a Chiralpak AS column (50×2 cm I.D.) eluting with hexane/i-PrOH 1:1 at 5 mL/minute. The enantiomer with the longer retention time was collected to provide (after removal of the solvent) (−) 2-[1-(3-chlorobenzyl)-4-methyl-6-hydroxy-4,5-dihydro-1H-thiopyrano[2,3,4c,d]indol-2-yl]ethanol.

Step 2: (+)
2-[2-[1-(3-Chlorobenzyl)-4-methyl-6-(5-phenylpyridin-2-ylmethoxy)-4,5-dihydro-1H-thiopyrano[2,3,4-c,d]indol-2-yl]ethoxy]phenylacetic acid Following the procedure described in Example 5, Steps 1-2, but substituting the (−) alcohol from Step 1 for [1-(4-chlorobenzyl)-4-methyl-6-(5-phenylpyridin-2-ylmethoxy)-4,5-dihydro-1H-thiopyrano[2,3,4-c,d]indol-2-yl]methanol as starting material, the title compound was obtained as a solid; m.p. 148°-149° C.
$[\alpha]_D$ +31.0° (c=0.3, CHCl$_3$).

EXAMPLE 35

2-[2-[1-(4-Fluorobenzyl)-4-methyl-6-(5-phenylpyridin-2-ylmethoxy)-4,5-dihydro-1H-thiopyrano[2,3,4-c,d]indol-2-yl]ethoxy]phenylacetic acid Step 1:
2-[1-(4-Fluorobenzyl)-4-methyl-6-hydroxy-4,5-dihydro-1H-thiopyrano[2,3,4-c,d]indol-2-yl]ethanol Following the procedure described in Example 20, Step 1, but substituting Ester 6 for Ester 4 as starting material, the title compound was obtained as a solid.

Step 2:
2-[1-(4-Fluorobenzyl)-4-methyl-6-(5-phenylpyridin-2-ylmethoxy)-4,5-dihydro-1H-thiopyrano[2,3,4-c,d]indol-2-yl]ethanol Following the procedure described in Example 1, Steps 1, but substituting the alcohol from Step 1 for the Ester 1 as starting material, the title compound was obtained as a solid.

Step 3:
2-[2-[1-(4-Fluorobenzyl-4-methyl-6-(5-phenylpyridin-2-ylmethoxy)-4,5-dihydro-1H-thiopyrano[2,3,4-c,d]indol-2-yl]ethoxy]phenylacetic acid Following the procedure described in Example 5, Steps 1-2, but substituting the alcohol from Step 2 for [1-(4-chlorobenzyl)-4-methyl-6-(5-phenylpyridin-2-ylmethoxy)-4,5-dihydro-1H-thiopyrano[2,3,4-c,d]indol-2-yl]methanol as starting material, the title compound was obtained as a solid; m.p. 196°-198° C.

EXAMPLE 36

(−)
2-[2-[1-(4-Fluorobenzyl)-4-methyl-6-(5-phenylpyridin-2-ylmethoxy-4,5-dihydro-1H-thiopyrano[2,3,4-c,d]indol-2-yl]ethoxy]phenylacetic acid Step 1: (+)
2-[1-(4-Fluorobenzyl)-4-methyl-6-(5-phenylpyridin-2-ylmethoxy)-4,5-dihydro-1H-thiopyrano[2,3,4-c,d]indol-2-yl]ethanol The title compound was obtained by following the procedure described in Example 35, Steps 1-2, but substituting the racemic material in Step 2 by (+) 2-[1-(4-fluorobenzyl)-4-methyl-6-hydroxy-4,5-dihydro-1H-thiopyrano[2,3,4-c,d]indol-2-yl]ethanol. Resolution of the racemate from Example 35, Step 1, was achieved by preparative HPLC using a Chiralpak AS column (50×2 cm I.D.) eluting with hexane/i-PrOH 1:1 at 5 mL/minute. The enantiomer with the shorter retention time was collected to provide (after removal of the solvent) (+) 2-[1-(4-fluorobenzyl)-4-methyl-6-hydroxy-4,5-dihydro-1H-thiopyrano[2,3,4-c,d]indol-2-yl]ethanol.

Step 2: (−)
2-[2-[1-(4-Fluorobenzyl)-4-methyl-6-(5-phenylpyridin-2-ylmethoxy)-4,5-dihydro-1H-thiopyrano[2,3,4-c,d]indol-2-yl]ethoxy]phenylacetic acid Following the procedure described in Example 5, Steps 1-2, but substituting the (+) alcohol from Step 1 for [1-(4-chlorobenzyl)-4-methyl-6-(5-phenylpyridin-2-ylmethoxy)-4,5-dihydro-1H-thiopyrano[2,3,4-c,d]indol-2-yl]methanol as starting material, the title compound was obtained as a solid; m.p. 181.3°-183.0° C.
[α]$_D$−3.7° (c=0.84, THF).

EXAMPLE 37

(+) 2-[2-[1-(4-Fluorobenzyl)-4-methyl-6-(5-phenylpyridin-2-ylmethoxy-4,5-dihydro-1H-thiopyrano[2,3,4c,d]indol-2-yl]ethoxy]phenylacetic acid

Step 1: (−)
2-[1-(4-Fluorobenzyl)-4-methyl-6-(5-phenylpyridin-2-ylmethoxy)-4,5-dihydro-1H-thiopyrano[2,3,4c,d]indol-2-yl]ethanol The title compound was obtained by following the procedure described in Example 35, Steps 1-2, but substituting the racemic material in Step 2 by (−) 2-[1-(4-fluorobenzyl)-4-methyl-6-hydroxy-4,5-dihydro-1H-thiopyrano[2,3,4-c,d]indol-2-yl]ethanol. Resolution of the racemate from Example 35, Step 1, was achieved by preparative HPLC using a Chiralpak AS column (50×2 cm I.D.) eluting with hexane/i-PrOH 1:1 at 5 mL/minute. The enantiomer with the longer retention time was collected to provide (after removal of the solvent) (−) 2-[1-(4-fluorobenzyl)-4-methyl-6-hydroxy-4,5-dihydro-1H-thiopyrano[2,3,4-c, d]indol-2-yl]ethanol.

Step 2: (30) 2-[2-[1-(4-Fluorobenzyl)-methyl-6-(5-phenylpyridin-2-ylmethoxy)-4,5-dihydro-1H-thiopyrano[2,3,4-c,d]indol-2-yl]ethoxy]phenylacetic acid Following the procedure described in Example 5, Steps 1-2, but substituting the (−) alcohol from Step 1 for [1-(4-chlorobenzyl)-4-methyl-6-(5-phenylpyridin-2-ylmethoxy)-4,5-dihydro-1H-thiopyrano[2,3,4-c,d]indol-2-yl]methanol as starting material, the title compound was obtained as a solid; m.p. 181.3°-183.0° C.
[α]$_D$+3.5+ (c=0.92, THF).

EXAMPLE 38

2-[2-[2[-1-(4-Fluorobenzyl)-4-methyl-6-(5-phenylpyridin-2-ylmethoxy)-4,5-dihydro-1H-thiopyrano[2,3,4-c,d]indol-2-yl]ethoxy]phenyl]propanoic acid Following the procedure described in Example 5, Steps 1-2, but substituting methyl 2-(2-hydroxyphenyl)-propanoate for methyl 2-hydroxyphenylacetate and 2-[1-(4-fluorobenzyl)-4-methyl-6-(5-phenylpyridin-2-ylmethoxy)-4,5-dihydro-1H-thiopyrano[2,3,4-c,d]indol-2-yl]ethanol from Example 35, Step 2, for [1-(4-chlorobenzyl)-4-methyl-6-(5-phenylpyridin-2-ylmethoxy)-4,5-dihydro-1H-thiopyrano[2,3,4-c,d]indol-2-yl]methanol as starting material; the title compound was obtained as a solid; m.p. 157°-160° C.

EXAMPLE 39

2-[2-[1-(3-Fluorobenzyl)-4-methyl-6-(5-phenylpyridin-2-ylmethoxy)-4,5-dihydro-1H-thiopyrano[2,3,4-c,d]indol-2-yl]ethoxy]phenylacetic acid

Step 1:
2-[1-(3-Fluorobenzyl)-4-methyl-6-hydroxy-4,5-dihydro-1H-thiopyrano[2,3,4-c,d]indol-2-yl]ethanol Following the procedure described in Example 20, Step 1, but substituting Ester 7 for Ester 4 as starting material, the title compound was obtained as a solid.

Step 2:
2-[1-(3-Fluorobenzyl)-4-methyl-6-(5-phenylpyridin-2-ylmethoxy)-4,5-dihydro-1H-thiopyrano[2,3,4-c,d]indol-2-yl]ethanol Following the procedure described in Example 1, Step 1, but substituting the alcohol from Step 1 for the Ester 1 as starting material, the title compound was obtained as a solid.

Step 3:
2-[2-[1-(3-Fluorobenzyl)-4-methyl-6-(5-phenylpyridin-2-ylmethoxy)-4,5-dihydro-1H-thiopyrano[2,3,4-c,d]indol-2-yl]ethoxy]phenylacetic acid Following the procedure described in Example 5, Steps 1-2, but substituting the alcohol from Step 2 for [1-(4-chlorobenzyl)-4-methyl-6-(5-phenylpyridin-2-ylmethoxy)-4,5-dihydro-1H-thiopyrano[2,3,4-c,d]indol-2yl]methanol as starting material. The title compound was obtained as a solid; m.p. 171.5°-173.5° C.

EXAMPLE 40

2-[1-(4-Chlorobenzyl)-4-methyl-6-(5-phenylpyridin-2-ylmethoxy)-4,5-dihydro-1H-thiopyrano[2,3,4-c,d]indol-2-ylthio]benzoic acid

Step 1:
[1-(4-Chlorobenzyl)-6-hydroxy-4-methyl-4,5-dihydro-1H-thiopyrano[2,3,4-c,d]indol-2-yl]carboxylic acid To a solution of Ester 1 (4.7 g) in THF (60 mL) and MeOH (60 mL) there was added 2.5N NaOH (50 mL) and the mixture was refluxed for 2.5 hours. The organic solvents were evaporated and the residue was diluted with H$_2$O and acidified with 1N HCl. Filtration of the precipitate afforded the product as a tan-colored solid.

Step 2:
1-(4-Chlorobenzyl)-6-hydroxy-4-methyl-4,5-dihydro-1H-thiopyrano[2,3,4-c,d]indole A mixture of the acid from Step 1 (4.1 g) and p-TSA (200 mg) in toluene (200 mL) was refluxed for 1.5 hour. The solvent was evaporated and the residue chromatographed on silica gel, eluting with a 1:3 mixture of EtOAc and hexane to afford the product as a yellow solid.

Step 3: Bis (2-carbomethoxyphenyl)disulfide

To a solution of thiosalicylic acid (9.24 g, 60 mmol) in EtOH (100 mL) and aq 1N NaOH (150 mL) at r.t., there was added slowly a solution of I$_2$ (15.2 g, 60 mmol) in EtOH (200 mL). The mixture was stirred for 15 minutes, then concentrated to one-half of its volume, diluted with H$_2$O, acidified with 2N HCl and the resulting diacid disulfide filtered (6.8 g). This was suspended in MeOH (200 mL), there was slowly added H$_2$SO$_4$ (2.7 mL) and the mixture was refluxed for two days. After cooling the insoluble product was filtered to afford the title diester as a cream-colored solid.

Step 4: Methyl 2-[1-(4-chlorobenzyl)-6-hydroxy-4-methyl-4,5-dihydro-1H-thiopyrano[2,3,4-c,d]indol-2-ylthio]benzoate To a solution of bis (2-carbomethoxyphenyl)disulfide, from Step 3, (301 mg, 0.9 mmol) in 1,2-dichloroethane (8 mL) at r.t. there was added SO$_2$Cl$_2$ (108 mg, 0.8 mmol) and the resulting solution was stirred for a further 20 minutes. This solution of 2-carbomethoxyphenylsulfenyl chloride was added slowly to a solution of the indole from Step 2 (460 mg, 1.4 mmol) in DMF (8 mL). The resulting mixture was stirred a further 30 minutes, then diluted with H₂O (100 mL), and extracted twice with Et₂O. These extracts were washed 3 times with H₂O, dried over MgSO₄, and evaporated to dryness. The residue was chromatographed on silica gel, eluting with a 1:3 mixture of EtOAc and hexane, to afford the product as a yellow oil which solidified. After trituration with hexane the product was obtained as a yellow solid.

Step 5: Methyl 2-[1-(4-chlorobenzyl)-4-methyl-6-(5-phenylpyridin-2-yl)methoxy-4,5-dihydro-1H-thiopyrano[2,3,4-c,d]indol-2-ylthio]benzoate To a solution of compound from Step 3 (550 mg, 1.11 mmol) in DMF (12 mL) at r.t. there was added NaH (30 mg, 1.25 mmol) and the resulting mixture was stirred for 30 minutes. There was added 5-phenyl-2-picolylchloride (285 mg, 1.4 mmol) and the mixture was stirred a further 4 hours. After addition of H₂O and excess 1N HCl, the mixture was extracted twice with EtOAc, these extracts were washed 3 times with H₂O, dried, and evaporated to dryness. The residue was chromatographed on silica gel, eluting with a 1:3 mixture of EtOAc and hexane, to afford the product as a yellow solid; m.p. 170°–172° C.

Step 6: 2-[1-(4-Chlorobenzyl)-4-methyl-6-(5-phenylpyridin-2-yl)methoxy-4,5-dihydro-1H-thiopyrano[2,3,4-c,d]indol-2-ylthio]benzoic acid To a solution of the ester from Step 4 (580 mg) in THF (12 mL) and MeOH (12 mL) there was added 2.5N NaOH (8 mL) and the mixture was refluxed for 30 minutes. The organic solvents were evaporated and the residue was diluted with H₂O water, acidified with 1N HCl, and filtered to afford the title compound as a cream-colored solid.

Anal. Calc'd for $C_{37}H_{29}ClN_2O_3S_2$: C, 68.15; H, 4.51; N, 4.32; S, 9.87; Cl, 5.40 Found: C, 68.00; H, 4.69; N, 4.26; S, 9.73; Cl, 5.65.

EXAMPLE 41

2-[1-(4-Chlorobenzyl)-4-methyl-6-(5-phenylpyridin-2-yl)methoxy-4,5-dihydro-1H-thiopyrano[2,3,4-c,d]indol-2-ylthio]phenylacetic acid

Step 1: Methyl 2-[1-(4-chlorobenzyl)-4-methyl-6-(5-phenylpyridin-2-yl)methoxy-4,5-dihydro-1H-thiopyrano[2,3,4-c,d]indol-2-ylthio]phenylacetate To a solution of 2-[1-(4-chlorobenzyl)-4-methyl-6-(5-phenylpyridin-2-yl)methoxy-4,5-dihydro-1H-thiopyrano[2,3,4-c,d]indol-2-ylthio]benzoic acid from Example 40, Step 5 (260 mg, 0.4 mmol) in CH₂Cl₂ (6 mL), there was added at room temperature oxalyl chloride (76 mg, 0.6 mmol) and DMF (0.02 mL). The mixture was stirred for 1 hour, then there was added excess ethereal diazomethane and stirring was continued for 2.5 hours. To this solution of diazoketone there was added MeOH (6 mL), silver benzoate (115 mg, 0.5 mmol), and Et₃N (0.5 mL). Stirring was continued for 2 hours. The MeOH and CH₂Cl₂ were evaporated, the residue was stirred with EtOAc (30 mL) and 1N HCl (15 mL) for 1 hour, and then filtered. Chromatography of the filtrate material on silica gel, eluting with a 1:2 mixture of EtOAc and hexane, afforded the product as a foamy solid.

Step 2: Methyl 2-[1-(4-chlorobenzyl)-4-methyl-6-(5-phenylpyridin-2-yl)methoxy-4,5-dihydro-1H-thiopyrano[2,3,4-c,d]indol-2-ylthio]phenylacetate A mixture of the ester from Step 1 (125 mg), THF (2 mL), EtOH (2 mL) and aq. 2.5N NaOH (2 mL) was stirred at r.t. for 1 hour. The organic solvents were evaporated. The residue was diluted with H₂O, acidified with 1N HCl and, after stirring for 20 minutes, was filtered. The solid was crystallized from THF-Et₂O to afford the title compound as yellow micro-crystals; m.p. 222°–224° C.

EXAMPLE 42

5-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethenylphen-2-yl]-1H-tetrazole

Step 1: [1-(4-Chlorobenzyl)-4-methyl-6-(5-phenylpyridin-2-ylmethoxy)-4,5-dihydro-1H-thiopyrano[2,3,4-c,d]indol-2-yl]carboxaldehyde A solution of [1-(4-chlorobenzyl)-4-methyl-6-(5-phenylpyridin-2-ylmethoxy)-4,5-dihydro-1H-thiopyrano[2,3,4-c,d]indol-2-yl]methanol (1.25 g), from Example 1, Step 2, in 100 mL THF at room temperature under nitrogen was treated with 4×1 g portions of MnO₂. After 2.5 hours, the mixture was filtered through a bed of celite and the solvent removed to give the title compound as a yellow solid.

Step 2: 2-[2-[4-Chlorobenzyl)-4-methyl-6-(5-phenylpyridin-2-ylmethoxy)-4,5-dihydro-1H-thiopyrano[2,3,4-c,d]indol-2-yl]ethenyl]benzonitrile A mixture of 2-cyanobenzyl bromide (Aldrich; 2.0 g) and Ph₃P (3.2 g) in 30 mL CH₃CN were stirred for 3 days under nitrogen. The solution was concentrated to 15 mL, Et₂O added, and the precipitate collected to provide 2-cyanobenzyltriphenylphosphonium bromide as a white solid.

To a suspension of 2-cyanobenzyltriphenylphosphonium bromide (926 mg) in 20 mL THF at −78° C. under nitrogen was added 4 mL of a 0.5M solution in toluene of KHMDS. After 45 minutes, the aldehyde from Step 1 (500 mg in 12 mL THF) was added and the solution warmed to r.t. Stirring was continued for 16 hours then the solution was poured into 1N HCl and extracted (3×EtOAc). The organic layers were dried (MgSO₄), evaporated, and the residue purified by chromatography (silica gel; hexane/EtOAc 3:2) to afford the title compound (a yellow solid) as a 1:1 mixture of E and Z isomers.

Step 3: 5-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethenylphen-2-yl]-1H-tetrazole Following the procedure described for Example 19 but substituting the nitrile from Step 2 for 2-[[1-(4-chlorobenzyl)-4-methyl-6-(5-phenylpyridin-2-ylmethoxy)-4,5-dihydro-1H-thiopyrano[2,3,4-c,d]indol-2-yl]indol-2-yl]methoxymethyl]benzonitrile as starting material, the title compound was obtained as a mixture of E and Z isomers; m.p. 190°–200° C. (dec).

EXAMPLE 43

2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethyl]benzoic acid Step 1:
2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethyl]benzonitrile A solution of 2-[2-[1-(4-chlorobenzyl)-4-methyl-6-(5-phenylpyridin-2-ylmethoxy)-4,5-dihydro-1H-thiopyrano[2,3,4-c,d]indol-2-yl]ethenyl]benzonitrile (1.28 g) from Example 42, Step 1, and triethylsilane (5 mL) in 40 mL $CH_2Cl_2$ was treated with 2.5 mL $BF_3.OEt_2$ at r.t. The reaction was stirred for 15 minutes then poured into IN HCl, extracted (3×EtOAc), washed (2×brine), dried ($MgSO_4$), and the solvent removed. The product was swished with $Et_2O$ and filtered to give the title compound as a solid.

Step 2:
2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethyl]benzoic acid Following the procedure described in Example 18, Step 2 but substituting the nitrile from Step 1 for 2-[[1-(4-chlorobenzyl)-4-methyl-6-(5-phenylpyridin-2-ylmethoxy)-4,5-dihydro-1H-thiopyrano[2,3,4-c,d]indol-2-yl]methoxymethyl]benzonitrile as starting material, the title compound was obtained as a solid; m.p. 209°–211° C.

EXAMPLE 44

5-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethylphen-2-yl]-1H-tetrazole Following the procedure described for Example 19 but substituting 2-[2-[1-(4-chlorobenzyl)-4-methyl-6-(5-phenylpyridin-2-ylmethoxy)-4,5-dihydro-1H-thiopyrano[2,3,4-c,d]indol-2-yl]ethyl]benzonitrile for 2-[[1-(4-chlorobenzyl)-4-methyl-6-(5-phenylpyridin-2-ylmethoxy)-4,5-dihydro-1H-thiopyrano[2,3,4-c,d]indol-2-yl]methoxymethyl]benzonitrile as starting material, the title compound was obtained as a solid; m.p. 209°–213° C.

EXAMPLE 45

3-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethyl]benzoic acid Following the procedures described in Example 42, Step 2 then Example 43, Steps 1-2, but substituting 3-cyanobenzyl bromide (Aldrich) for 2-cyanobenzyl bromide as starting material, the title compound was obtained as a solid; m.p. 211°–213° C.

EXAMPLE 46

3-[1-(4-Chlorobenzyl)-4-methyl-6-(5-phenylpyridin-2-ylmethoxy)-4,5-dihydro-1H-thiopyrano[2,3,4-c,d]indol-2-yl]methoxymethyl]benzoic acid Following the procedure described in Example 18, Steps 1-2, but substituting 3-cyanobenzyl bromide (Aldrich) for 2-cyanobenzyl bromide as starting material, the title compound was obtained as a solid; m.p. 163°–167° C. (dec).

EXAMPLE 47

5-[[1-(4-Chlorobenzyl)-4-methyl-6-(5-phenylpyridin-2-ylmethoxy)-4,5-dihydro-1H-thiopyrano[2,3,4-c,d]indol-2-yl]methoxymethylphen-3-yl]-1H-tetrazole Following the procedures described in Example 18, Step 1 then Example 19 but substituting 3-cyanobenzyl bromide (Aldrich) for 2-cyanobenzyl bromide as starting material, the title compound was obtained as a solid; m.p. 166°–167° C.

EXAMPLE 48

3-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxymethyl]benzoic acid Following the procedure described in Example 18, Steps 1-2, but substituting 3-cyanobenzyl bromide (Aldrich) for 2-cyanobenzyl bromide and [1-(4-chlorobenzyl)-4-methyl-6-(5-phenylpyridin-2-ylmethoxy)-4,5-dihydro-1H-thiopyrano[2,3,4-c,d]indol-2-yl]ethanol for [1-(4-chlorobenzyl)-4-methyl-6-(5-phenylpyridin-2-ylmethoxy)-4,5-dihydro-1H-thiopyrano[2,3,4-c,d]indol-2-yl]methanol as starting materials, the title compound was obtained as a solid; m.p. 171°–173° C.

EXAMPLE 49

5-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxymethylphen-3-yl]-1H-tetrazole Following the procedures described in Example 18, Step 1 and then Example 19 but substituting 3-cyanobenzyl bromide (Aldrich) for 2-cyanobenzyl bromide and [1-(4-chlorobenzyl)-4-methyl-6-(5-phenylpyridin-2-ylmethoxy)-4,5-dihydro-[2,3,4-c,d]indol-2-yl]ethanol for [1-(4-chlorobenzyl)-4-methyl-6-(5-phenylpyridin-2-ylmethoxy)-4,5-dihydro-1H-thiopyrano[2,3,3-c,d]indol-2-yl]methanol as starting materials, the title compound was obtained as a solid; m.p. 115° C. (dec).

EXAMPLE 50

3-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]benzoic acid Following the procedure described in Example 5, Steps 1-2, but substituting methyl 3-hydroxybenzoate (Aldrich) for methyl 2-hydroxyphenylacetate and 2-[1-(4-chlorobenzyl)-4-methyl-6-(5-phenylpyridin-2-ylmethoxy)-4,5-dihydro-1H-thiopyrano[2,3,4-c,d]indol-2-yl]ethanol from Example 20, Step 2, for [1-(4-chlorobenzyl)-4-methyl-6-(5-phenylpyridin-2-ylmethoxy)-4,5-dihydro-1H-thiopyrano]2,3,4-c,d]indol-2-yl]methanol as starting material, the title compound was obtained as a solid; m.p. 195°–198° C.

EXAMPLE 51

5-[[1-(4-Chlorobenzyl)-4-methyl-6-(5-phenylpyridin-2-ylmethoxy-4,5-dihydro-1H-thiopyrano[2,3,4-c,d]indol-2-yl](hydroxy)methyl]furan-2-carboxylic acid

Step 1: Methyl 5-[[1-(4-chlorobenzyl)-4-methyl-6-(5-phenylpyridin-2-ylmethoxy)-4,5-dihydro-1H-thiopyrano[2,3,4-c,d]indol-2-yl](hydroxy)methyl]furan-2-carboxylate To a solution of diisopropylamine (1.1 mL, 7.6 mmol) in dry THF (3 mL) at 0° C. was added n-BuLi 1.25M in hexane (6 mL, 7.6 mmol), then cooled to −70° C. To this LDA solution was added 2-furoic acid (Aldrich; 385 mg, 3.4 mmol) in dry THF (5 mL), stirred 30 minutes followed by dropwise addition of [1-(4-chlorobenzyl)-4-methyl-6-(5-phenylpyridin-2-ylmethoxy)-4,5-dihydro-1H-thiopyrano[2,3,4-c,d]indol-2-yl]carboxyaldehyde from Example 42, Step 1 (1.2 g, 2.3 mmol) in dry THF (20 mL). The temperature was raised to −50° C., quenched with NH$_4$OAc, and warmed to r.t. Extraction with EtOAc and treatment of the resulting oil with excess of a solution of diazomethane in Et$_2$O followed by evaporation and chromatography (silica gel, EtOAc/hexane 4:6) afforded the title compound.

Step 2: 5-[[1-(4-Chlorobenzyl)-4-methyl-6-(5-phenylpyridin-2-ylmethoxy)-4,5-dihydro-1H-thiopyrano[2,3,4-c,d]indol-2-yl](hydroxy)methyl]furan-2-carboxylic acid Following the procedure described in Example 5, Step 2, but substituting the product from Step 1 for methyl 2-[1-(4-chlorobenzyl)-4-methyl-6-(5-phenylpyridin-2-ylmethoxy)-4,5-dihydro-1H-thiopyrano[2,3,4-c,d]indol-2-ylmethoxy]phenylacetate, there was obtained the title product as a solid; m.p. 140°–145° C. (dec).

EXAMPLE 52

5-[[1-(4-Chlorobenzyl)-4-methyl-6-(5-phenylpyridin-2-ylmethoxy)-4,5-dihydro-1H-thiopyrano[2,3,4-c,d]indol-2-yl]methyl]furan-2-carboxylic acid

Step 1: Methyl 5-[[1-(4-chlorobenzyl)-4-methyl-6-(5-phenylpyridin-2-ylmethoxy)-4,5-dihydro-1H-thiopyrano[2,3,4-c,d]indol-2-yl]methyl]furan-2-carboxylate To a solution of methyl 5-[[1-(4-chlorobenzyl)-4-methyl-6-(5-phenylpyridin-2-ylmethoxy)-4,5-dihydro-1H-thiopyrano[2,3,4-c,d]indol-2-yl](hydroxy)methyl]furan-2-carboxylate from Example 51, Step 1 (900 mg, 1.4 mmol) in CH$_2$Cl$_2$ (20 mL) at 0° C. was added triethylsilane (0.33 mL, 2.1 mmol) followed by TFA (1.1 mL, 13.8 mmol). The resulting solution was stirred at 0° C. for 20 minutes, diluted with CH$_2$Cl$_2$ (200 mL), washed with aqueous saturated NaHCO$_3$, brine, dried, and evaporated to afford the title compound.

Step 2: 5-[[1-(4-Chlorobenzyl)-4-methyl-6-(5-phenylpyridin-2-ylmethoxy)-4,5-dihydro-1H-thiopyrano[2,3,4-c,d]indol-2yl]methyl]furan-2carboxylic acid Following the procedure described in Example 5, Step 2, but substituting the product from Step 1 for methyl 2-[1-(4-chlorobenzyl)-4-methyl-6-(5-phenylpyridin-2-ylmethoxy)-4,5-dihydro-1H-thiopyrano[2,3,4-c,d]indol-2-ylmethoxy]phenylacetate, there was obtained the title product as a solid; m.p. >210° C.

Anal. Calc'd for C$_{36}$H$_{29}$O$_4$N$_2$ClS: C, 69.66; H, 4.70; N, 4.52. Found: C, 69.78; H, 4.66; N, 3.91.

EXAMPLE 53

5-[[1-(4-Chlorobenzyl)-4-methyl-6-(5-phenylpyridin-2-ylmethoxy)-4,5-dihydro-1H-thiopyrano[2,3,4-c,d]indol-2-yl](methoxy)methyl]furan-2-carboxylic acid

Step 1: Methyl 5-[1-(4-chlorobenzyl)-4-methyl-6-(5-phenylpyridin-2-ylmethoxy)-4,5-dihydro-1H-thiopyrano[2,3,4-c,d]indol-2-yl](methoxy)methyl]furan-2-carboxylate To a solution of methyl 5-[[1-(4-chlorobenzyl)-4-methyl-6-(5-phenylpyridin-2-ylmethoxy)-4,5-dihydro-1H-thiopyrano[2,3,4-c,d]indol-2-yl](hydroxy)methyl]furan-2-carboxylate from Example 51 (360 mg, 0.55 mmol) in dry DMF (10 mL) was added NaH (40 mg, 1.7 mmol) in portions. The resulting solution was stirred 30 minutes, and MeI (0.34 mL, 5.5 mmol) was added. The resulting black solution was stirred for 3 hours, then added slowly to a saturated aqueous NaHCO$_3$ solution, extracted with EtOAc, dried, and evaporated. Purification by chromatography on silica gel, eluting with a 3:7 mixture of EtOAc in hexane, afforded the title compound.

Step 2: 5-[[1-(4-Chlorobenzyl)-4-methyl-6-(5-phenylpyridin-2-ylmethoxy)-4,5-dihydro-1H-thiopyrano[2,3,4-c,d]indol-2-yl](methoxy)methyl]furan-2-carboxylic acid Following the procedure described in Example 5, Step 2, but substituting the product from Step 1 for methyl 2-[1-(4-chlorobenzyl)-4-methyl-6-(5-phenylpyridin-2-ylmethoxy)-4,5-dihydro-1H-thiopyrano[2,3,4-c,d]indol-2-ylmethoxy]phenylacetate, there was obtained the title compound as a solid; m.p. 100°–110° C.

EXAMPLE 54

5-[[1-(4-Chlorobenzyl)-4-methyl-6-(5-phenylpydridin-2-ylmethoxy)-4,5-dihydro-1H-thiopyrano[2,3,4-c,d]indol-2-yl]methyl]furan-2-acetic acid

Step 1: Methyl 5-[[1-(4-chlorobenzyl)-4-methyl-6-(5-phenylpyridin-2-ylmethoxy)-4,5-dihydro-1H-thiopyrano[2,3,4-c,d]indol-2yl]methyl]furan-2-acetate To a solution of 5-[[1-(4-chlorobenzyl)-4-methyl-6-(5-phenylpyridin-2-ylmethoxy)-4,5-dihydro-1H-thiopyrano[2,3,4-c,d]indol-2-yl]methyl]furan-2-carboxylic acid from Example 52 (200 mg, 0.32 mmol) in CH$_2$Cl$_2$ (5 mL) at 0° C. was added oxalyl chloride (56 μL, 0.65 mmol) followed by two drops of DMF and the resulting solution was stirred for 20 min. The solvent was evaporated and Et$_2$O (5 mL) was added followed by an excess of an etheral solution of diazomethane. After 1.5 hours the solvent was evaporated and the resulting oil was dissolved in MeOH (4 mL), Et$_3$N (0.5 mL), and then silver benzoate (36 mg, 0.16 mmol) was added. The resulting heterogenous mixture was stirred at room temperature for 2 hours, diluted with EtOAc (100 mL), washed with 1N HCl, brine, dried, and evaporated. Purification on silical gel, eluting with a mixture of 3:7 EtOAc in hexane, gave the title compound.

Step 2:
5-[[1-(4-Chlorobenzyl)-4-methyl-6-(5-phenylpyridin-2-ylmethoxy-4,5-dihydro-1H-thiopyrano[2,3,4-c,d,]indol-2-yl]methyl]furan-2-acetic acid Following the procedure described in Example 5, Step 2, but substituting the product from Step 1 for methyl 2-[1-(4-chlorobenzyl)-4-methyl-6-(5-phenylpyridin-2-ylmethoxy)-4,5-dihydro-1H-thiopyrano[2,3,4-c,d]indol-2-ylmethoxy]phenylacetate, there was obtained the title compound as a solid; m.p. 164°–167° C.

EXAMPLE 55

5-[[1-(4-Chlorobenzyl)-4-methyl-6-(5-phenylpyridin-2-ylmethoxy)-4,5-dihydro-1H-thiopyrano[2,3,4-c,d]indol-2-yl]methyl](N-methylsulfonyl)furan-2-carboxamide Following the procedure described in Example 4 but substituting 5-[[1-(4-chlorobenzyl)-4-methyl-6-(5-phenylpyridin-2-ylmethoxy)-4,5-dihydro-1H-thiopyrano[2,3,4-c,d]indol-2-yl]methyl]furan-2-carboxylic acid from Example 52, Step 2, for 2-[1-(4-chlorobenzyl)-4-methyl-6-(5-phenylpyridin-2-ylmethoxy)-4,5-dihydro-1H-thiopyrano[2,3,4-c,d]indol-2-ylmethylthio]benzoic acid as starting material, the title compound was obtained as a solid; m.p. 132°–134° C.

EXAMPLE 56

5-[[1-(4-Chlorobenzyl)-4-methyl-6-(5-phenylpyridin-2-ylmethoxy)-4,5-dihydro-1H-thiopyrano[2,3,4-c,d]indol-2-yl]methyl](N-phenylsulfonyl)furan-2-carboxamide Following the procedure described in Example 4, but substituting benzenesulfonamide (Aldrich) for methanesulfonamide and 5-[[1-(4-chlorobenzyl)-4-methyl-6-(5-phenylpyridin-2-ylmethoxy)-4,5-dihydro-1H-thiopyrano[2,3,4-c,d]indol-2-yl]methyl]furan-2-carboxylic acid (from Example 52, Step 2) for 2-[1-(4-chlorobenzyl)-4-methyl-6-(5-phenylpyridin-2-ylmethoxy)-4,5-dihydro-1H-thiopyrano[2,3,4-c,d]indol-2-ylmethylthio]benzoic acid as starting materials, the title compound was obtained as a solid; m.p. 214°–216° C.

EXAMPLE 57

5-Chloro-2-[[1-(4-chlorobenzyl)-4-methyl-6-(5-phenylpyridin-2-ylmethoxy)-4,5-dihydro-1H-thiopyrano[2,3,4-c,d]indol-2-yl]ethoxy]benzoic acid Following the procedure described in Example 5, Steps 1–2, but substituting methyl 5-chloro-2-hydroxybenzoate (prepared by treating 5-chloro-2-hydroxybenzoic acid (Aldrich) with ethereal diazomethane) for methyl 2-hydroxyphenylacetate and 2-[1-(4-chlorobenzyl)-4-methyl-6-(5-phenylpyridin-2-ylmethoxy)-4,5-dihydro-1H-thiopyrano[2,3,4-c,d]indol-2-yl]ethanol from Example 20, Step 2, for [1-(4-chlorobenzyl)-4-methyl-6-(5-phenylpyridin-2-ylmethoxy)-4,5-dihydro-1H-thiopyrano[2,3,4-c,d]indol-2-yl]methanol as starting material, the title compound was obtained as a solid; m.p. 170°–173° C.

EXAMPLE 58

(+) 2-[1-(4-Chlorobenzyl)-4-methyl-6-(5-phenylpyridin-2-ylmethoxy)-4,5-dihydro-1H-thiopyrano[2,3,4-c,d]indol-2-ylmethoxy]phenylacetic acid Step 1: (+) [1-(4-Chlorobenzyl)-4-methyl-6-hydroxy-2-ylmethoxy)-4,5-dihydro-1H-thiopyrano[2,3,4-c,d]indol-2-yl]methanol Following the procedure described in Example 20, Step 1, but replacing Ester 4 with Ester 1, the title compound was obtained in racemic form. Resolution of the racemate was achieved by preparative HPLC using a Chiralpak AS column (50×2 cm I.D.) eluting with hexane/i-PrOH 3:2 at 5 mL/minute. The enantiomer with the shorter retention time was collected to provide (after removal of the solvent) the title compound.

Step 2: (+) [1-(4-Chlorobenzyl)-4-methyl-6-(5-phenylpyridin-2-ylmethoxy)-4,5-dihydro-1H-thiopyrano[2,3,4-c,d]indol-2-yl]methanol Following the procedure described in Example 1, Step 1, but replacing Ester 1 with the alcohol from Step 1, the title compound was obtained as a solid.

Step 3: (+) 2-[1-(4-Chlorobenzyl)-4-methyl-6-(5-phenylpyridin-2-ylmethoxy)-4,5-dihydro-1H-thiopyrano[2,3,4-c,d]indol-2-ylmethoxy]-phenylacetic acid Following the procedure described in Example 5, Steps 1–2, but substituting the alcohol from Step 2 for [1-(4-chlorobenzyl)-4-methyl-6-(5-phenylpyridin-2-ylmethoxy)-4,5-dihydro-1H-thiopyrano[2,3,4-c,d]indol-2-yl]methanol in Step 1, the title compound was obtained as a solid; m.p. 117°–120° C. (dec).

$[\alpha]_D + 8.1°$ (c=0.23, CHCl$_3$).

EXAMPLE 59

(−) 2-[1-(4-Chlorobenzyl)-4-methyl-6-(5-phenylpyridin-2-ylmethoxy)-4,5-dihydro-1H-thiopyrano[2,3,4-c,d]indol-2-ylmethoxy]phenylacetic acid Step 1: (−) [1-(4-Chlorobenzyl)-4-methyl-6-hydroxy-2-ylmethoxy)-4,5-dihydro-1H-thiopyrano[2,3,4-c,d]indol-2-yl]methanol Following the procedure described in Example 20, Step 1, but replacing Ester 4 with Ester 1, the title compound was obtained in racemic form. Resolution of the racemate was achieved by preparative HPLC using a Chiralpak AS column (50×2 cm I.D.) eluting with hexane/i-PrOH 3:2 at 5 mL/minute. The enantiomer with the longer retention time was collected to provide (after removal of the solvent) the title compound.

Step 2: (−) [1-(4-Chlorobenzyl)-4-methyl-6-(5-phenylpyridin-2-ylmethoxy)-4,5-dihydro-1H-thiopyrano[2,3,4-c,d]indol-2-yl]methanol Following the procedure described in Example 1, Step 1, but replacing Ester 1 with the alcohol from Step 1, the title compound was obtained as a solid.

Step 3: (−)
2-[1-(4-Chlorobenzyl)-4-methyl-6-(5-phenylpyridin-2-ylmethoxy)-4,5-dihydro-1H-thiopyrano[2,3,4-c,d]indol-2-ylmethoxy]phenylacetic acid Following the procedure described in Example 5, Steps 1-2, but substituting the alcohol from Step 2 for [1-(4-chlorobenzyl)-4-methyl-6-(5-phenylpyridin-2-ylmethoxy)-4,5-dihydro-1H-thiopyrano[2,3,4-c,d]indol-2-yl]methanol in Step 1, the title compound was obtained as a solid; m.p. 117°-120° C. (dec).
$[\alpha]_D$−10.0° (c=0.26, CHCl$_3$).

EXAMPLE 60

(−)
2-[2-[1-(4-Chlorobenzyl)-4-methyl-6-(5-phenylpyridin-2-ylmethoxy)-4,5-dihydro-1H-thiopyrano[2,3,4-c,d]indol-2-ylmethoxy]phenyl]propanoic acid Following the procedure described in Example 5, Steps 1-2, but substituting (−) [1-(4-chlorobenzyl)-4-methyl-6-(5-phenylpyridin-2-ylmethoxy)-4,5-dihydro-1H-thiopyrano[2,3,4-c,d]indol-2-yl]methanol from Example 59, Step 1, for [1-(4-chlorobenzyl)-4-methyl-6-(5-phenylpyridin-2-ylmethoxy)-4,5-dihydro-1H-thiopyrano[2,3,4-c,d]indol-2-yl]methanol and methyl 2-(2-hydroxyphenyl)propanoate for methyl 2-hydroxyphenyl acetate as starting materials in Step 1, the title compound was obtained as a solid; m.p. 118°-121° C.
$[\alpha]_D$−13.7° (c=0.26, CHCl$_3$).

EXAMPLE 61

(+)
2-[2-[1-(4-Fluorobenzyl)-4-methyl-6-(5-phenylpyridin-2-ylmethoxy)-4,5-dihydro-1H-thiopyrano[2,3,4-c,d]indol-2-ylmethoxy]phenyl]propanoic acid

Step 1: (+)
[1-(4-Fluorobenzyl)-4-methyl-6-(5-phenylpyridin-2-ylmethoxy)-4,5-dihydro-1H-thiopyrano[2,3,4-c,d]indol-2-yl]methanol Following the procedure described for Example 58, Steps 1-2, but substituting Ester 4 with Ester 3 as starting material in Step 1, the title compound was obtained as a solid.

Step 2: (+)
2-[2-[1-(4-Fluorobenzyl)-4-methyl-6-(5-phenylpyridin-2-ylmethoxy)-4,5-dihydro-1H-thiopyrano[2,3,4-c,d]indol-2-ylmethoxy]phenyl]propanoic acid Following the procedure described in Example 14, but substituting the (+) alcohol from Step 1, for the racemate as starting material in Step 1, the title compound was obtained as a solid; m.p. 120°-124° C.
$[\alpha]_D$8.7° (c=0.26, CHCl$_3$).

EXAMPLE 62

(−)
2-[2-[1-(4-Fluorobenzyl)-4-methyl-6-(5-phenylpyridin-2-ylmethoxy)-4,5-dihydro-1H-thiopyrano[2,3,4-c,d]indol-2-ylmethoxy]phenyl]propanoic acid

Step 1: (−)
[1-(4-Fluorobenzyl)-4-methyl-6-(5-phenylpyridin-2-ylmethoxy)-4,5-dihydro-1H-thiopyrano[2,3,4-c,d]indol-2-yl]methanol Following the procedure described for Example 59, Steps 1-2, but substituting Ester 4 with Ester 3 as starting material in Step 1, the title compound was obtained as a solid.

Step 2: (−)
2-[2-[1-(4-Fluorobenzyl)-4-methyl-6-(5-phenylpyridin-2-ylmethoxy)-4,5-dihydro-1H-thiopyrano[2,3,4-c,d]indol-2-ylmethoxy]phenyl]propanoic acid Following the procedure described in Example 14, but substituting the (−) alcohol from Step 1, for the racemate and as starting material in Step 1, the title compound was obtained as a solid; m.p. 121°-124° C.
$[\alpha]_D$−12.3° (c=0.26, CHCl$_3$).

EXAMPLE 63

2-[1-(4-Azido-3-iodophenylsulfonyl)-4-methyl-6-(5-phenylpyridin-2-ylmethoxy)-4,5-dihydro-1H-thiopyrano[2,3,4-c,d]indol-2-ylmethylthio]benzoic acid

Step 1:
2-[4-Methyl-6-(5phenylpyridin-2-ylmethoxy)-4,5-dihydro-1H-thiopyrano[2,3,4-c,d]indol-2-ylmethylthio]benzoic acid Following the procedure described in Example 1, Steps 2 and 3 but substituting ethyl [4-methyl-6-(5-phenylpyridin-2-ylmethoxy)-4,5-dihydro-1H-thiopyrano[2,3,4-c,d]indol-2-yl]carboxylate from Example 15, Step 2 for ethyl [1-(4-chlorobenzyl)-4-methyl-6-(5-phenylpyridin-2-ylmethoxy)-4,5-dihydro-1H-thiopyrano[2,3,4-c,d]indol-2-yl]carboxylate as starting material, the title compound was obtained as a solid.

Step 2:
2-[1-(4-Azido-3-iodophenylsulfonyl)-4-methyl-6-(5-phenylpyridin-2-ylmethoxy)-4,5-dihydro-1H-thiopyrano[2,3,4-c,d]indol-2-ylmethyl]benzoic acid To a suspension of the indole from Step 1 (100 mg) in THF (7 mL) at −78° C. under nitrogen was added KHMDS (0.5M in toluene, 0.80 mL). After stirring for 5 minutes at −78° C. the temperature was raised to 0° C. while stirring for 1 hour. The solution was then cooled to −78° C. and 4-azido-3-iodophenylsulfonyl chloride (J. Med. Chem., 1991, 34, 1511) (69 mg) in THF (1.0 mL) was added. Following stirring at −78° C. for a further 30 minutes, the reaction was quenched with NH$_4$Cl (saturated) and partitioned between EtOAc and dilute HCl (aq). The organic layer was washed with H$_2$O and brine, dried over MgSO$_4$, and evaporated. Purification on flash chromatography (silica gel; CH$_2$Cl$_2$/MeOH/NH$_4$OH, 60:10:1) followed by an Et$_2$O swish gave the title compound as a solid; m.p. 170°-180° C. (dec).

EXAMPLE 64

(−)
2-[1-(3-Chlorobenzyl)-4-methyl-6-(5-phenylpyridin-2-ylmethoxy)-4,5-dihydro-1H-thiopyrano[2,3,4-c,d]indol-2-ylmethoxy]phenylacetic acid

Step 1: (−)
[1-(3-Chlorobenzyl)-4-methyl-6-(5-phenylpyridin-2-ylmethoxy)-4,5-dihydro-1H-thiopyrano[2,3,4-c,d]indol-2-yl]methanol Following the procedure described for Example 59, Steps 1-2, but substituting Ester 4 with Ester 2 as starting material in Step 1, the title compound was obtained as a solid.

Step 2: (−)
2-[1-(3-Chlorobenzyl)-4-methyl-6-(5-phenylpyridin-2-ylmethoxy)-4,5-dihydro-1H-thiopyrano[2,3,4-c,d]indol-2-ylmethoxy]phenylacetic acid Following the procedure described in Example 11, but substituting the (−) alcohol from Step 1 for the racemate, the title compound was obtained as a solid; m.p. 153.5°–154° C.

$[\alpha]_D$ −16.1° (c=0.52, CHCl$_3$).

EXAMPLE 65

(+)
2-[1-(3-Chlorobenzyl)-4-methyl-6-(5-phenylpyridin-2-ylmethoxy)-4,5-dihydro-1H-thiopyrano[2,3,4-c,d]indol-2-ylmethoxy]phenylacetic acid Step 1: (+)
[1-(3-Chlorobenzyl)-4-methyl-6-(5-phenylpyridin-2-ylmethoxy)-4,5-dihydro-1H-thiopyrano[2,3,4-c,d]indol-2-yl]methanol Following the procedure described for Example 58, Steps 1–2, but substituting Ester 4 with Ester 2 as starting material in Step 1, the title compound was obtained as a solid.

Step 2: (+)
2-[1-(3-Chlorobenzyl)-4-methyl-6-(5-phenylpyridin-2-ylmethoxy)-4,5-dihydro-1H-thiopyrano[2,3,4-c,d]indol-2-ylmethoxy]phenylacetic acid Following the procedure described in Example 11, but substituting the (+) alcohol from Step 1 for the racemate, the title compound was obtained as a solid; m.p. 153°–155° C.

$[\alpha]_D$ +12.1° (c=0.34, CHCl$_3$).

EXAMPLE 66

2-[1-(4-Chlorobenzyl)-4-methlyl-6-(quinolin-2-ylmethoxy)-4,5-dihydro-1H-thiopyrano[2,3,4-c,d]indol-2-ylmethylthio]benzoic acid Step 1:
[1-(4-Chlorobenzyl)-4-methyl-6-(quinolin-2-ylmethoxy)-4,5-dihydro-1H-thiopyrano[2,3,4-c,d]indol-2-yl]methanol Following the procedure described in Example 1, Step 1, but substituting 2-chloromomethylquinoline (Aldrich) for 5-phenyl-2-picolyl chloride and racemic [1-(4-chlorobenzyl)-4-methyl-6-hydroxy-4,5-dihydro-1H-thiopyrano[2,3,4-c,d]indol-2-yl]methanol from Example 58, Step 1, for Ester 1, the title compound was obtained as a solid.

Step 2:
2-[1-(4-Chlorobenzyl)-4-methyl-6-(quinolin-2-ylmethoxy)-4,5-dihydro-1H-thiopyrano[2,3,4-c,d]indol-2-ylmethylthio]benzoic acid Following the procedure described for Example 1, Step 3, but substituting the alcohol from Step 1 for 2-[1-(4-chlorobenzyl)-4-methyl-6-(5-phenylpyridin-2-ylmethoxy)-4,5-dihydro-1H-thiopyrano[2,3,4-c,d]indol-2-yl]methanol as starting material, the title compound was obtained as a solid; m.p. 218.5°–220° C.

EXAMPLE 67

2-[1-(4-Chlorobenzyl)-4-methyl-6-(quinolin-2-ylmethoxy)-4,5-dihydro-1H-thiopyrano[2,3,4-c,d]indol-2-ylmethoxy]phenylacetic acid Following the procedure described for Example 5, Steps 1–2, but substituting 2-[1-(4-chlorobenzyl)-4-methyl-6-(quinolin-2-ylmethoxy)-4,5-dihydro-1H-thiopyrano[2,3,4-c,d]indol-2-yl]methanol from Example 66, Step 1 for 2-[1-(4-chlorobenzyl)-4-methyl-6-(5-phenylpyridin-2-ylmethoxy)-4,5-dihydro-1H-thiopyrano[2,3,4-c,d]indol-2-yl]methanol as starting material, the title compound was obtained as a solid; m.p. 128°–130° C.

EXAMPLE 68

2-[1-(4-Chlorobenzyl)-4-methyl-6-(isoquinolin-3-ylmethoxy)-4,5-dihydro-1H-thiopyrano[2,3,4-c,d]indol-2-ylmethylthio]benzoic acid Following the procedure described in Example 66, Steps 1–2, but substituting 3-chloromethyl isoquinoline (Chem. Abst.: 94, 121512t(1981)) for 2-chloromethylquinoline as starting material, the title compound was obtained as a solid; m.p. 220° C. (dec).

EXAMPLE 69

2-[1-(4-Chlorobenzyl)-4-methyl-6-(pyridin-2-ylmethoxy)-4,5-dihydro-1H-thiopyrano[2,3,4-c,d]indol-2-ylmethylthio]benzoic acid Following the procedure described in Example 66, Steps 1–2, but substituting 2-picolyl chloride (Aldrich) for 2-chloromethylquinoline as starting material, the title compound was obtained as a solid; m.p. 137° C. (dec).

EXAMPLE 70

2-[1-(4-Chlorobenzyl)-4-methyl-6-(5-methoxypyridin-2-ylmethoxy)-4,5-dihydro-1H-thiopyrano[2,3,4-c,d]indol-2-ylmethylthio]benzoic acid Following the procedure described in Example 66, Steps 1–2, but substituting 5-methoxy-2-picolyl chloride (U.S. Pat. No. 4,230,714 Oct. 28, 1980)) for 2-chloromethylquinoline as starting material, the title compound was obtained as a solid; m.p. 206°–207° C. (dec).

EXAMPLE 71

2-[1-(4-Chlorobenzyl)-4-methyl-6-(2-methylthiazol-4-ylmethoxy)-4,5-dihydro-1H-thiopyrano[2,3,4-c,d]indol-2-ylmethoxy]phenylacetic acid Step 1:
[1-(4-Chlorobenzyl)-4-methyl-6-(2-methylthiazol-4-ylmethoxy)-4,5-dihydro-1H-thiopyrano-[2,3,4-c,d]indol-2-yl]methanol Following the procedure described in Example 1, Step 1, but substituting 4-chloromethyl-2-methylthiazole (Maybridge) for 5-phenyl-2-picolyl chloride and racemic [1-(4-chlorobenzyl)-4-methyl-6-hydroxy-4,5-dihydro-1H-thiopyrano[2,3,4-c,d]indol-2-yl]methanol from Example 58, Step 1, for Ester 1, the title compound was obtained as a solid.

Step 2:
2-[1-(4-Chlorobenzyl)-4-methyl-6-(2-methylthiazol-4-ylmethoxy)-4,5-dihydro-1H-thiopyrano[2,3,4-c,d]indol-2-ylmethoxy]phenylacetic acid Following the procedure described for Example 5, Steps 1-2, but substituting the alcohol from Step 1 for 2-[1-(4-chlorobenzyl)4-methyl-6-(5-phenylpyridin-2-ylmethoxy)-4,5-dihydro-1H-thiopyrano[2,3,4-c,d]indol-2-yl]methanol as starting material, the title compound was obtained as a solid; m.p. 117°-119° C.

EXAMPLE 72

3-[1-(4-Chlorobenzyl)-4-methyl-6-(5-phenylpyridin-2-ylmethoxy)-4,5-dihydro-1H-thiopyrano[2,3,4-c,d]indol-2-ylmethoxy]-2-naphthoic acid Following the procedure described in Example 5, Steps 1-2, but substituting methyl 3-hydroxy-2-naphthoate (prepared by treating 3-hydroxy-2-naphthoic acid (Aldrich) with ethereal diazomethane) for methyl 2-hydroxyphenylacetate as starting material in Step 1, the title compound was obtained as a solid; m.p. 170°-174° C.

What is claimed is:
1. A compound of the formula:

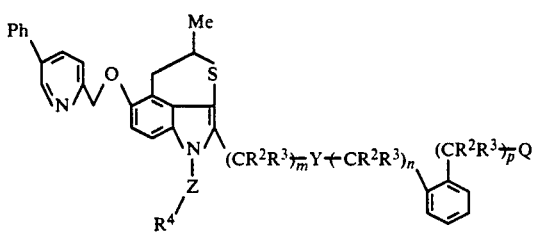

Ib wherein the substituents are as follows:

| EX. NO. | $R^4Z$ | $(CR^2R^3)_mY(CR^2R^3)_n$ |
|---|---|---|
| 1 | 4-ClC$_6$H$_4$CH$_2$ | CH$_2$S |
| 2 | 3-ClC$_6$H$_4$CH$_2$ | CH$_2$S |
| 3 | 4-FC$_6$H$_4$CH$_2$ | CH$_2$S |
| 4 | 4-ClC$_6$H$_4$CH$_2$ | CH$_2$S |
| 5 | 4-ClC$_6$H$_4$CH$_2$ | CH$_2$O |
| 6 | 4-ClC$_6$H$_4$CH$_2$ | CH$_2$O |
| 7 | 4-ClC$_6$H$_4$CH$_2$ | CH$_2$O |
| 8 | 4-ClC$_6$H$_4$CH$_2$ | CH$_2$O |
| 9 | 4-ClC$_6$H$_4$CH$_2$ | CH$_2$O |
| 10 | 4-ClC$_6$H$_4$CH$_2$ | CH$_2$S |
| 11 | 3-ClC$_6$H$_4$CH$_2$ | CH$_2$O |
| 12 | 3-ClC$_6$H$_4$CH$_2$ | CH$_2$O |
| 13 | 4-FC$_6$H$_4$CH$_2$ | CH$_2$O |
| 14 | 4-FC$_6$H$_4$CH$_2$ | CH$_2$O |
| 15 | 3-Cl-4-FC$_6$H$_3$CH$_2$ | CH$_2$O |
| 16 | C$_6$H$_5$ | CH$_2$O |
| 17* | 3-(C$_5$H$_7$O)C$_6$H$_4$CH$_2$ | CH$_2$O |
| 18 | 4-ClC$_6$H$_4$CH$_2$ | CH$_2$OCH$_2$ |
| 19 | 4-ClC$_6$H$_4$CH$_2$ | CH$_2$OCH$_2$ |
| 20 | 4-ClC$_6$H$_4$CH$_2$ | (CH$_2$)$_2$OCH$_2$ |
| 21 | 4-ClC$_6$H$_4$CH$_2$ | (CH$_2$)$_2$S |
| 22 | 4-ClC$_6$H$_4$CH$_2$ | (CH$_2$)$_2$O |
| 23 | 4-ClC$_6$H$_4$CH$_2$ | (CH$_2$)$_2$O |
| 24 | 4-ClC$_6$H$_4$CH$_2$ | (CH$_2$)$_2$O |
| 25 | 4-ClC$_6$H$_4$CH$_2$ | (CH$_2$)$_2$O |
| 26 | 4-ClC$_6$H$_4$CH$_2$ | (CH$_2$)$_2$O |
| 27 | 3-ClC$_6$H$_4$CH$_2$ | (CH$_2$)$_2$O |
| 28 | 4-ClC$_6$H$_4$CH$_2$ | (CH$_2$)$_2$S |
| 29 | 4-ClC$_6$H$_4$CH$_2$ | (CH$_2$)$_2$O |
| 30 | 4-ClC$_6$H$_4$CH$_2$ | (CH$_2$)$_2$O |
| 31 | 4-ClC$_6$H$_4$CH$_2$ | (CH$_2$)$_2$O |
| 32 | 3-ClC$_6$H$_4$CH$_2$ | (CH$_2$)$_2$O |
| 33 | 3-ClC$_6$H$_4$CH$_2$ | (CH$_2$)$_2$O |
| (−)-enantiomer | | |
| 34 | 3-ClC$_6$H$_4$CH$_2$ | (CH$_2$)$_2$O |
| (+)-enantiomer | | |
| 35 | 4-FC$_6$H$_4$CH$_2$ | (CH$_2$)$_2$O |
| 36 | 4-FC$_6$H$_4$CH$_2$ | (CH$_2$)$_2$O |
| (−)-enantiomer | | |
| 37 | 4-FC$_6$H$_4$CH$_2$ | (CH$_2$)$_2$O |
| (+)-enantiomer | | |
| 38 | 4-FC$_6$H$_4$CH$_2$ | (CH$_2$)$_2$O |
| 39 | 3-FC$_6$H$_4$CH$_2$ | (CH$_2$)$_2$O |
| 40 | 4-ClC$_6$H$_4$CH$_2$ | S |
| 41 | 4-ClC$_6$H$_4$CH$_2$ | S |
| 42 | 4-ClC$_6$H$_4$CH$_2$ | CH=CH (E&Z isomers) |
| 43 | 4-ClC$_6$H$_4$CH$_2$ | (CH$_2$)$_2$ |
| 44 | 4-ClC$_6$H$_4$CH$_2$ | (CH$_2$)$_2$ |
| 58 | 4-ClC$_6$H$_4$CH$_2$ | CH$_2$O |
| (+)-enantiomer | | |
| 59 | 4-ClC$_6$H$_4$CH$_2$ | CH$_2$O |
| (−)enantiomer | | |
| 60 | 4-ClC$_6$H$_4$CH$_2$ | CH$_2$O |
| (−)enantiomer | | |
| 61 | 4-FC$_6$H$_4$CH$_2$ | CH$_2$O |
| (+)enantiomer | | |
| 62 | 4-FC$_6$H$_4$CH$_2$ | CH$_2$O |
| (−)enantiomer | | |
| 63 | 3-I-4-N$_3$C$_6$H$_3$S(O)$_2$ | CH$_2$S |
| 64 | 3-ClC$_6$H$_4$CH$_2$ | CH$_2$O |
| (−)enantiomer | | |
| 65 | 3-ClC$_6$H$_4$CH$_2$ | CH$_2$O |
| (+)enantiomer | | |

| EX. NO. | $(CR^2R^3)_p$ | Q |
|---|---|---|
| 1 | — | CO$_2$H, |
| 2 | — | CO$_2$H, |
| 3 | — | CO$_2$H. |
| 4 | — | CONHS(O)$_2$Me, |
| 5 | CH$_2$ | CO$_2$H. |
| 6 | CH$_2$ | CONHS(O)$_2$Me. |
| 7 | CH(Me) | CO$_2$H, |
| 8 | CH(Me) | CONHS(O)$_2$Me, |
| 9 | CH(Et) | CO$_2$H, |
| 10 | CH$_2$ | CO$_2$H, |
| 11 | CH$_2$ | CO$_2$H, |
| 12 | CH(Me) | CO$_2$H, |
| 13 | CH$_2$ | CO$_2$H, |
| 14 | CH(Me) | CO$_2$H, |
| 15 | CH$_2$ | CO$_2$H. |
| 16 | CH$_2$ | CO$_2$H, |
| 17* | CH$_2$ | CO$_2$H, |
| 18 | — | CO$_2$H, |
| 19 | — | CN$_4$H, |
| 20 | — | CN$_4$H, |
| 21 | — | CO$_2$H, |
| 22 | — | CO$_2$H, |
| 23 | — | CONHS(O)$_2$Me, |
| 24 | — | CN$_4$H, |
| 25 | — | S(O)$_2$NHCOMe, |
| 26 | — | S(O)$_2$NHCOPh, |
| 27 | — | CO$_2$H, |
| 28 | CH$_2$ | CO$_2$H, |
| 29 | CH$_2$ | CO$_2$H, |
| 30 | CH(Me) | CO$_2$H, |
| 31 | CH(Et) | CO$_2$H, |
| 32 | CH$_2$ | CO$_2$H, |
| 33 | CH$_2$ | CO$_2$H, |
| (−)enantiomer | | |
| 34 | CH$_2$ | CO$_2$H, |
| (+)enantiomer | | |
| 35 | CH$_2$ | CO$_2$H, |
| 36 | CH$_2$ | CO$_2$H, |
| (−)enantiomer | | |
| 37 | CH$_2$ | CO$_2$H, |
| (+)enantiomer | | |
| 38 | CH(Me) | CO$_2$H. |
| 39 | CH$_2$ | CO$_2$H. |
| 40 | — | CO$_2$H. |
| 41 | CH$_2$ | CO$_2$H, |
| 42 | — | CN$_4$H, |
| 43 | — | CO$_2$H, |
| 44 | — | CN$_4$H, |
| 58 | CH$_2$ | CO$_2$H, |
| (+)enantiomer | | |

| | | |
|---|---|---|
| 59 (−)enantiomer | CH₂ | CO₂H, |
| 60 (−)enantiomer | CH(Me) | CO₂H, |
| 61 (+)enantiomer | CH(Me) | CO₂H, |
| 62 (−)enantiomer | CH(Me) | CO₂H, |
| 63 | — | CO₂H, |
| 64 (−)enantiomer | CH₂ | CO₂H, or |
| 65 (+)enantiomer | CH₂ | CO₂H, |

*EX 17: C₅H₇O is 2H-5,6-dihydropyran-4-yl

2. A compound of the formula:

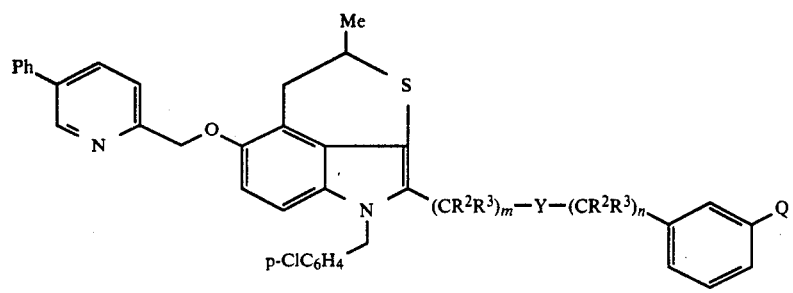

wherein the substituents are as follows:

| EX. NO. | (CR²R³)ₘY(CR²R³)ₙ | Q |
|---|---|---|
| 45 | (CH₂)₂ | CO₂H, |
| 46 | CH₂OCH₂ | CO₂H, |
| 47 | CH₂OCH₂ | CN₄H, |
| 48 | (CH₂)₂OCH₂ | CO₂H, |
| 49 | (CH₂)₂OCH₂ | CN₄H or |
| 50 | (CH₂)₂O | CO₂H |

3. A compound of the formula:

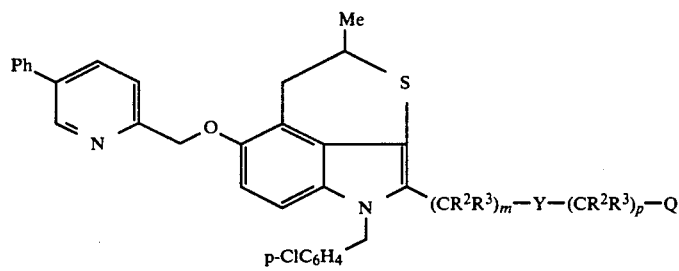

wherein the substituents are as follows:

| EX. NO. | (CR²R³)ₘY | Ar | (CR²R³)ₚ | Q |
|---|---|---|---|---|
| 51 | CH(OH) | 2,5-furandiyl | — | CO₂H, |
| 52 | CH₂ | 2,5-furandiyl | — | CO₂H, |
| 53 | CH(OMe) | 2,5-furandiyl | — | CO₂H, |
| 54 | CH₂ | 2,5-furandiyl | CH₂ | CO₂H, |
| 55 | CH₂ | 2,5-furandiyl | — | CONHS(O)₂Me, |
| 56 | CH₂ | 2,5-furandiyl | — | CONHS(O)₂Ph, |
| 57 | (CH₂)₂O | C₆H₃Cl | — | CO₂H or |
| 72 | CH₂O | C₁₀H₆ | — | CO₂H |

4. A pharmaceutical composition comprising a therapeutically effective amount of a compound of claims 1 or 3 and a pharmaceutically acceptable carrier.

5. A method of preventing the synthesis, the action,

Ic

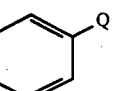

or the release of SRS-A or leukotrienes in a mammal which comprises administering to said mammal an effective amount of a compound of claims 1, 2 or 3.

6. A method of claim 5 wherein the mammal is man.

7. A method of treating asthma in a mammal comprising administering to a mammal in need of said treatment a therapeutically effective amount of a compound of claims 1, 2 or 3.

8. A method of treating inflammatory diseases of the eye in a mammal which comprises administering to a mammal in need of such treatment a therapeutically Id effective amount of a compound of claims 1, 2 or 3.

9. The method of claim 8 wherein the mammal is man.

* * * * *